US008911973B2

(12) United States Patent
Hall et al.

(10) Patent No.: US 8,911,973 B2
(45) Date of Patent: Dec. 16, 2014

(54) SNAP-BACK PRIMERS AND DETECTABLE HAIRPIN STRUCTURES

(71) Applicant: Third Wave Technologies, Inc., Madison, WI (US)

(72) Inventors: Jeff G. Hall, Waunakee, WI (US); Andrew A. Lukowiak, Stoughton, WI (US); Patrick Peterson, Madison, WI (US)

(73) Assignee: Third Wave Technologies, Inc., Madison, WI (US)

( * ) Notice: Subject to any disclaimer, the term of this patent is extended or adjusted under 35 U.S.C. 154(b) by 0 days.

(21) Appl. No.: 13/899,230

(22) Filed: May 21, 2013

(65) Prior Publication Data

US 2014/0004514 A1 Jan. 2, 2014

Related U.S. Application Data

(62) Division of application No. 11/866,663, filed on Oct. 3, 2007, now Pat. No. 8,445,238.

(60) Provisional application No. 60/849,280, filed on Oct. 4, 2006.

(51) Int. Cl.
*C12P 19/34* (2006.01)
*C12Q 1/68* (2006.01)

(52) U.S. Cl.
CPC ............ *C12Q 1/6858* (2013.01); *C12Q 1/6813* (2013.01); *C12Q 1/6827* (2013.01)
USPC ........................................ 435/91.2; 435/6.12

(58) Field of Classification Search
USPC ............................................... 435/91.2, 6.12
See application file for complete search history.

(56) References Cited

U.S. PATENT DOCUMENTS

| 5,001,050 | A | 3/1991 | Blanco |
| 5,198,543 | A | 3/1993 | Blanco |
| 5,424,186 | A | 6/1995 | Fodor |
| 5,472,881 | A | 12/1995 | Beebe |
| 5,538,848 | A | 7/1996 | Livak |
| 5,587,128 | A | 12/1996 | Wilding |
| 5,614,402 | A | 3/1997 | Dahlberg |
| 5,744,305 | A | 4/1998 | Fodor |
| 5,795,763 | A | 8/1998 | Dahlberg |
| 5,843,669 | A | 12/1998 | Kaiser |
| 5,846,717 | A | 12/1998 | Brow |
| 5,985,557 | A | 11/1999 | Prudent |
| 5,994,069 | A | 11/1999 | Hall |
| 6,001,567 | A | 12/1999 | Brow |
| 6,001,983 | A | 12/1999 | Benner |
| 6,090,543 | A | 7/2000 | Prudent |
| 6,090,606 | A | 7/2000 | Kaiser |
| 6,117,634 | A | 9/2000 | Langmore |
| 6,126,899 | A | 10/2000 | Woudenberg |
| 6,183,960 | B1 | 2/2001 | Lizardi |
| 6,194,149 | B1 | 2/2001 | Neri |
| 6,197,557 | B1 | 3/2001 | Makarov |
| 6,210,884 | B1 | 4/2001 | Lizardi |
| 6,235,502 | B1 | 5/2001 | Weissman |
| 6,291,187 | B1 | 9/2001 | Kingsmore |
| 6,319,469 | B1 | 11/2001 | Mian |
| 6,323,009 | B1 | 11/2001 | Lasken |
| 6,375,903 | B1 | 4/2002 | Cerrina |
| 6,399,397 | B1 | 6/2002 | Zarling et al. |
| 6,410,278 | B1 | 6/2002 | Notomi |
| 6,448,010 | B1 | 9/2002 | Zhao |
| 6,548,250 | B1 | 4/2003 | Sorge |
| 6,627,159 | B1 | 9/2003 | Bedingham |
| 6,660,517 | B1 | 12/2003 | Wilding |
| 6,709,869 | B2 | 3/2004 | Mian |
| 6,720,187 | B2 | 4/2004 | Bedingham |
| 6,734,401 | B2 | 5/2004 | Bedingham |
| 6,913,881 | B1 | 7/2005 | Aizenstein et al. |
| 7,011,944 | B2 | 3/2006 | Prudent et al. |
| 2004/0014067 | A1 | 1/2004 | Lyamichev |
| 2005/0186588 | A1 | 8/2005 | Lyamichev |
| 2006/0147955 | A1 | 7/2006 | Allawi |
| 2010/0143898 | A1 | 6/2010 | Kutyavin |

FOREIGN PATENT DOCUMENTS

| WO | WO95/11995 | 5/1995 |
| WO | WO97/27214 | 7/1997 |
| WO | WO98/23774 | 6/1998 |
| WO | WO98/39485 | 9/1998 |
| WO | WO98/42873 | 10/1998 |
| WO | WO98/50403 | 11/1998 |
| WO | WO99/42813 | 8/1999 |
| WO | WO01/88190 | 11/2001 |
| WO | WO01/90337 | 11/2001 |
| WO | WO01/98537 | 12/2001 |
| WO | WO02/00934 | 1/2002 |

(Continued)

OTHER PUBLICATIONS

Notomi et al., "Loop-mediated isothermal amplification of DNA," Nucleic Acids Research, 2000, vol. 28, No. 12, e63 i-vii.

(Continued)

*Primary Examiner* — Cynthia B Wilder

(74) *Attorney, Agent, or Firm* — Casimir Jones S.C.

(57) ABSTRACT

The present invention provides methods, compositions, and kits comprising snap-back primers used for forming 3' hairpin structures, 5' hairpin structures, and double hairpin structures. The hairpin structures may be used for detecting target sequences (e.g., such as small RNA target sequence), for detecting polymorphisms in target sequences (e.g., such as polymorphisms located near the 5' or 3' ends of the target sequence), or other nucleic acid characterization methods. In certain embodiments, the hairpin structures form invasive cleavage structures (e.g., in combination with a probe or upstream oligonucleotide) which may be cleaved by structure-specific enzymes in order to detect the presence or absence of a particular nucleotide or nucleotide sequence.

21 Claims, 12 Drawing Sheets

(56) References Cited

FOREIGN PATENT DOCUMENTS

| WO | WO02/04597 | 1/2002 |
|----|------------|--------|
| WO | WO02/070755 | 9/2002 |
| WO | WO03/073067 | 9/2003 |
| WO | WO2004/057017 | 7/2004 |
| WO | WO2005/010199 | 2/2005 |

OTHER PUBLICATIONS

Lyamichev et al., "Polymorphism identification and quantitative detection of genomic DNA invasive cleavage of oligonucleotide probes," Nature Biotech., 1999, vol. 17, pp. 292-296.

Tani et al., "Technique for Quantitative Detection of Specific DNA Sequences Using Alternately Binding Quenching Probe Competitive Assay Combined wlh Loop-Mediated Isothermal Amplification," Anal. Chern., Aug. 2007, vol. 79, No. 15, pp. 5608-5613.

Kao et al., "Cleavage Specificity of *Saccharomyces cerevisiae* Flap Enconuclease 1 Suggests a Double-Flap Structure as the Cellular Substrate," The Journal of Biological Chemistry, 2002, pp. 14379-14389, volume-issue number(s), publisher, city and/or country where published.

Liu et al., "*Saccharomyces cerevisiae* Flap Enconuclease 1 Use Flap Equilibration to Maintain Triplet Repeat Stability," Molecular and Cellular Biology, 2004, pp. 4049-4064, vol. 24.

Myers et al., "Reverse Transcription and DNA Amplification by a Thermus thermophilus DNA Polymerase," Biochemistry, 1991, pp. 7661-7666, vol. 30.

Solinas et al., "Intramolecular TaqMan probes for genetic analysis," Chemical Communications, 2002, pp. 2272-2273, vol. 19.

Wang et al., "Human Bloom Protein Stimulates Flap Enconuclease 1 Activity by Resolving DNA Secondary Structure," The Journal of Biological Chemistry, 2005, pp. 5391-5399, vol. 280.

Kutyavin et al., 2000, "3'—Minor groove binder-DNA probes increase sequence specificity at PCR extension temperatures," Nucleic Acids Research, pp. 655-661, vol. 28.

Allawi et al. "Quantitation of microRNAs using a modified Invader assay" RNA, Cold Spring Harbor Lab Press, vol. 10, No. 7, pp. 1153-1163 (2004).

Kwiatkowski, et al. "Clinical, Genetic, and Pharmacogenetic Applications of the Invader Assay" Molecular Diagnosis, vol. 4, No. 4, pp. 353-64 (1999).

Allawi, et al. "Thermodynamics and NMR of internal G.T mismatches in DNA" Biochemistry 36, 10581-94 (1997).

Anderson, et al. "Quantitative Filter Hybridization" Nucleic Acid Hybridization (1985) pp. 73-111.

Bauer, et al. "Paternity testing after pregnancy termination using laser microdissection of chorionic villi" Int. J. Legal Med. 116: 39-42 (2002).

Bilkova, et al. "Oriented immobilization of chymotrypsin by use of suitable antibodies coupled to a nonporous solid support" J. Chromatogr. A, 852:141-9 [1999].

Cargill, et al. "Characterization of single-nucleotide polymorphisms in coding regions of human genes" Nature Genetics, 22: 231-8 (1999).

Chamberlain, et al. "Deletion screening of the Duchenne muscular dystrophy locus via multiplex DNA amplification" Nucleic Acids Res., 16:11141-56 (1988).

Chernukhin, et al. "A method of immobilization on the solid support of complex and simple enzymes retaining their activity" Anal. Biochem. 280:178-81 [2000].

Corstjens, et al. "Infrared up-converting phosphors for bioassays" IEE Proc. Nanobiotechnol. 152(2):64-72 [2005].

Doty, et al. "Strand Separation and Specific Recombination in Deoxyribonucleic Acids: Physical Chemical Studies" Proc. Natl. Acad. Sci. USA 46:461-76 (1960).

Elnifro, et al. "Multiplex PCR: optimization and application in diagnostic virology" Clinical Microbiology Reviews, 13: 559-70 (2000).

Frey, et al. "Covalent Attachment and Derivatization of Poly(L-lysine) Monolayers on Gold Surfaces As Characterized by Polarization—Modulation FT-IR Spectroscopy" Analytical Chem, 68:3187 [1996].

Frutos, et al. "Demonstration of a word design strategy for DNA computing on surfaces" Nucl. Acid. Res., 25:4748-57 [1997].

Guo, et al. "Direct fluorescence analysis of genetic polymorphisms by hybridization with oligonucleotide arrays on glass supports" Nucleic Acids Res., 22:5456-62 [1994].

Hagmann, "Human genome. A good SNP may be hard to find" Science, 285: 21-2 (1999).

Hall, et al. "Sensitive detection of DNA polymorphisms by the serial invasive signal amplification reaction" PNAS, USA, 97:8272-7 (2000).

Halushka, et al., "Patterns of single-nucleotide polymorphisms in candidate genes for blood-pressure homeostasis" Nature Genetics, 22: 239-47 (1999).

Hidding, et al. "Haplotype frequencies and population data of nine Y-chromosomal STR polymorphisms in a German and a Chinese population" Forensic Sci. Int., 113: 47-53 (2000).

Jordan, et al. "Surface Plasmon Resonance Imaging Measurements of DNA Hybridization Adsorption and Streptavidin/DNA Multilayer Formation at Chemically Modified Gold Surfaces" Analytical Chem, vol. 69, pp. 4939-4947 [1997].

Kong, et al. "Synthesis of oligodeoxyribonucleotides containing degenerate bases and their use as primers in the polymerase chain reaction" Nucleic Acids Res., 1992, 20, 5149-5152.

Kong, et al. "Synthesis and duplex stability of oligonucleotides containing cytosine-thymine analogues" Nucleic Acids Res., 1989, 17, 10373-10383.

Kwok, et al. "Single nucleotide polymorphism libraries: why and how are we building them?" Molecular Medicine Today, 5: 538-543 (1999).

Kwok "Approaches to allele frequency determination" Pharmacogenomics, 1: 231-5 (2000).

Lindblad-Toh, et al. "Large-scale discovery and genotyping of single-nucleotide polymorphisms in the mouse" Nature Genet. 4: 381-6 (2000).

Marmur, et al. "Strand Separation and Specific Recombination in Deoxyribonucleic Acids: Biological Studies" Proc. Natl. Acad. Sci. USA 46:453-61 (1960).

Maskos, et al. "Oligonucleotide hybridisations on glass supports: a novel linker for oligonucleotide synthesis and hybridisation properties of oligonucleotides synthesised in situ" Nucleic Acids Res., 20:1679 [1992].

Mathews, et al. "Predicting Oligonucleotide affinity to nucleic acid targets" RNA 5:1458-69 [1999].

Nuzzo, et al. "Adsorption of Bifunctional Organic Disulfides on Gold Surfaces" JACS, 105:4481-3 [1983].

O'Donnelly-Maloney, et al. "Microfabrication and array technologies for DNA sequencing and diagnostics" Genetic Analysis: Biomolecular Engineering, 13:151-7 [1996].

Ostermayer "Preparation and properties of infrared-to-visible conversion phosphors" Metall. Trans. 752, 747-755 [1971].

Ouhibi, et al. "Preimplantation Genetic Diagnosis" Curr Womens Health Rep. 1: 138-42 (2001).

Risch, et al. "The Future of Genetic Studies of Complex Human Diseases" Science, 273: 1516-7 (1996).

Rudi, et al. "Development and application of new nucleic acid-based thechnologies for microbial community analyses in foods" Int'l J Food Microbiology, 78: 171-80 (2002).

Rychlik, et al. "A computer program for choosing optimal oligonucleotides for filter hybridization, sequencing and in vitro amplification of DNA" Nucleic Acids Res, 17: 8543-51 [1989].

Santalucia "A unified view of polymer, dumbbell, and oligonucleotide DNA nearest-neighbor thermodynamics" Proc Natl Acad Sci U S A, 95:1460-5 [1998].

Schweitzer, et al. "Hydrophobic, Non-Hydrogen-Bonding Bases and Base Pairs in DNA" J. Am. Chem. Soc., 1995, 117, 1863-1872.

Schweitzer, et al. "Aromatic Nonpolar Nucleosides as Hydrophobic Isosteres of Pyrimidine and Purine Nucleosides" J. Org. Chem., 1994, 59, 7238-7242.

Selvin "Fluorescence Resonance Energy Transfer" 1995, Methods Enzymol., 246:300-34.

Shalon "A DNA Microarray System for Analyzing Complex DNA Samples Using Two-color Fluorescent Probe Hybridization" Genome Methods, 6:639-45 [1996].

(56) References Cited

OTHER PUBLICATIONS

Shchepinov, et al. "Steric factors influencing hybridisation of nucleic acids to oligonucleotide arrays" Nucleic Acids Research, vol. 25, pp. 1155-61 [1997].

Stryer, et al. "Fluorescence Energy Transfer As a Spectroscopic Ruler" 1978, Ann. Rev. Biochem., 47:819-46.

Suter, et al. "The Immunochemistry of Sandwich Elisas. II. A Novel System Prevents the Denaturation of Capture Antibodies" Immunol. Lett. 13:313 [1986].

Tyagi, et al. "Wavelength-shifting molecular beacons" Nature Biotechnology 18:1191-6 (2000).

Van De Rijke, et al. "Up-converting phosphor reporters for nucleic acid microarrays" Nature Biotechnol. 19(3):273-6 [2001].

Walsh, et al. "Preferential PCR Amplification of Alleles: Mechanisms and Solutions" PCR Methods and Applications, 1: 241-50 (1992).

Zarlenga, et al. "PCR as a disgnostic and quantitative technique in veterinary parasitology" Vet Parasitol. 101: 215-30 (2001).

Zuker "On Finding All Suboptimal Foldings of an RNA Molecule" Science, 244: 48-52 [1989].

FOZ / Ratio
Het Sample

| | FAM | Red | Ratio |
|---|---|---|---|
| 1717-1G>A, 2 Primer | 6.15 | 4.70 | 1.39 |
| 1717-1G>A, 4 Primer | 7.36 | 4.62 | 1.76 |
| | | | |
| G542X, 2 Primer | 3.72 | 6.67 | 2.08 |
| G542X, 4 Primer | 2.88 | 4.47 | 1.84 |
| | | | |
| G551D, 2 Primer | 2.16 | 12.46 | 9.91 |
| G551D, 4 Primer | 2.57 | 13.94 | 8.23 |
| | | | |
| R560T, 2 Primer | 1.88 | 12.16 | 12.63 |
| R560T, 4 Primer | 1.32 | 11.18 | 31.71 |

WT Sample

| | FAM | Red | Ratio |
|---|---|---|---|
| 1717-1G>A, 2 Primer | 5.79 | 0.53 | 479.03 |
| 1717-1G>A, 4 Primer | 7.49 | 0.57 | 649.16 |
| G542X, 2 Primer | 1.73 | 6.67 | 7.73 |
| G542X, 4 Primer | 0.66 | 5.56 | 455.72 |
| G551D, 2 Primer | 0.79 | 12.41 | 1141.08 |
| G551D, 4 Primer | 0.87 | 13.96 | 1295.58 |
| R560T, 2 Primer | 1.94 | 6.08 | 5.42 |
| R560T, 4 Primer | 1.35 | 3.08 | 5.93 |

SEQUENCE LISTING

```
<160> NUMBER OF SEQ ID NOS: 40

<210> SEQ ID NO 1
<211> LENGTH: 33
<212> TYPE: DNA
<213> ORGANISM: Artificial
<220> FEATURE:
<223> OTHER INFORMATION: Synthetic

<400> SEQUENCE: 1
gtgaataact aattattggt ctagcaagca ttt                            33

<210> SEQ ID NO 2
<211> LENGTH: 31
<212> TYPE: DNA
<213> ORGANISM: Artificial
<220> FEATURE:
<223> OTHER INFORMATION: Synthetic

<400> SEQUENCE: 2
cacttattga ttaataacca gatcgaagtg a                              31

<210> SEQ ID NO 3
<211> LENGTH: 34
<212> TYPE: DNA
<213> ORGANISM: Artificial
<220> FEATURE:
<223> OTHER INFORMATION: Synthetic
```

-continued

<400> SEQUENCE: 3
gattacgact ctctaattt ctatttttgg taat                                34

<210> SEQ ID NO 4
<211> LENGTH: 28
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (28)..(28)
<223> OTHER INFORMATION: The residue at this position is linked to
      hexanediol

<400> SEQUENCE: 4
cgcgccgagg aggacatctc caagtttg                                      28

<210> SEQ ID NO 5
<211> LENGTH: 30
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (30)..(30)
<223> OTHER INFORMATION: The residue at this position is linked to
      hexanediol

<400> SEQUENCE: 5
acggacgcgg agaagacatc tccaagtttg                                    30

<210> SEQ ID NO 6
<211> LENGTH: 34
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a dye
      moiety
<220> FEATURE:
<221> NAME/KEY: misc_feature
<222> LOCATION: (4)..(4)
<223> OTHER INFORMATION: The residue at this position is linked to a
      quencher moiety
<220> FEATURE:
<221> NAME/KEY: misc_feature
<222> LOCATION: (34)..(34)
<223> OTHER INFORMATION: The residue at this position is linked to
      hexanediol

<400> SEQUENCE: 6
tctaagccgg ttttccggct gagacctcgg cgcg                               34

<210> SEQ ID NO 7
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a dye
      moiety
<220> FEATURE:
<221> NAME/KEY: misc_feature

```
<222> LOCATION: (4)..(4)
<223> OTHER INFORMATION: The residue at this position is linked to a
      quencher moiety
<220> FEATURE:
<221> NAME/KEY: misc_feature
<222> LOCATION: (36)..(36)
<223> OTHER INFORMATION: The residue at this position is linked to
      hexanediol

<400> SEQUENCE: 7
tctttcggcc ttttggccga gagactccgc gtccgt                              36

<210> SEQ ID NO 8
<211> LENGTH: 29
<212> TYPE: DNA
<213> ORGANISM: Artificial
<220> FEATURE:
<223> OTHER INFORMATION: Synthetic

<400> SEQUENCE: 8
caagaagcag agaaagacaa tatagttct                                     29

<210> SEQ ID NO 9
<211> LENGTH: 29
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (29)..(29)
<223> OTHER INFORMATION: The residue at this position is linked to
      hexanediol

<400> SEQUENCE: 9
aggccacgga cgggagaagg tggaatcac                                     29

<210> SEQ ID NO 10
<211> LENGTH: 28
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (28)..(28)
<223> OTHER INFORMATION: The residue at this position is linked to
      hexanediol

<400> SEQUENCE: 10
cgcgccgagg tgagaaggtg gaatcaca                                      28

<210> SEQ ID NO 11
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a dye
      moiety
<220> FEATURE:
<221> NAME/KEY: misc_feature
<222> LOCATION: (4)..(4)
<223> OTHER INFORMATION: The residue at this position is linked to a
      quencher moiety
<220> FEATURE:
<221> NAME/KEY: misc_feature
<222> LOCATION: (36)..(36)
```

```
<223> OTHER INFORMATION: The residue at this position is linked to
      hexanediol

<400> SEQUENCE: 11
tctttcggcc ttttggccga gagacgtccg tggcct                              36

<210> SEQ ID NO 12
<211> LENGTH: 23
<212> TYPE: DNA
<213> ORGANISM: Artificial
<220> FEATURE:
<223> OTHER INFORMATION: Synthetic

<400> SEQUENCE: 12
tctccgaagg tggaatcaca ctg                                            23

<210> SEQ ID NO 13
<211> LENGTH: 28
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (28)..(28)
<223> OTHER INFORMATION: The residue at this position is linked to
      hexanediol

<400> SEQUENCE: 13
cgcgccgagg gtcaacgagc aagaattt                                       28

<210> SEQ ID NO 14
<211> LENGTH: 31
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (31)..(31)
<223> OTHER INFORMATION: The residue at this position is linked to
      hexanediol

<400> SEQUENCE: 14
aggccacgga cgatcaacga gcaagaattt c                                   31

<210> SEQ ID NO 15
<211> LENGTH: 34
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a dye
      moiety
<220> FEATURE:
<221> NAME/KEY: misc_feature
<222> LOCATION: (4)..(4)
<223> OTHER INFORMATION: The residue at this position is linked to a
      quencher moiety
<220> FEATURE:
<221> NAME/KEY: misc_feature
<222> LOCATION: (34)..(34)
<223> OTHER INFORMATION: The residue at this position is linked to
      hexanediol

<400> SEQUENCE: 15
tctttcggcc ttttggccga gagacctcgg cgcg                                34
```

```
<210> SEQ ID NO 16
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a dye
      moiety
<220> FEATURE:
<221> NAME/KEY: misc_feature
<222> LOCATION: (4)..(4)
<223> OTHER INFORMATION: The residue at this position is linked to a
      quencher moiety
<220> FEATURE:
<221> NAME/KEY: misc_feature
<222> LOCATION: (36)..(36)
<223> OTHER INFORMATION: The residue at this position is linked to
      hexanediol

<400> SEQUENCE: 16
tctaagccgg ttttccggct gagacgtccg tggcct                                    36

<210> SEQ ID NO 17
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (33)..(33)
<223> OTHER INFORMATION: The residue at this position is linked to
      hexanediol

<400> SEQUENCE: 17
acggacgcgg agcttgctaa agaaattctt gct                                       33

<210> SEQ ID NO 18
<211> LENGTH: 31
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (31)..(31)
<223> OTHER INFORMATION: The residue at this position is linked to
      hexanediol

<400> SEQUENCE: 18
cgcgccgagg gttgctaaag aaattcttgc t                                         31

<210> SEQ ID NO 19
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: The residue at this position is linked to a dye
      moiety
<220> FEATURE:
<221> NAME/KEY: misc_feature
<222> LOCATION: (4)..(4)
<223> OTHER INFORMATION: The residue at this position is linked to a
      quencher moiety
```

```
<220> FEATURE:
<221> NAME/KEY: misc_feature
<222> LOCATION: (36)..(36)
<223> OTHER INFORMATION: The residue at this position is linked to
      hexanediol

<400> SEQUENCE: 19
tctaagccgg ttttccggct gagactccgc gtccgt                                    36

<210> SEQ ID NO 20
<211> LENGTH: 55
<212> TYPE: DNA
<213> ORGANISM: Artificial
<220> FEATURE:
<223> OTHER INFORMATION: Synthetic

<400> SEQUENCE: 20
atgacgtggc agacctgagg ctttcctgat gactataaaa atagacttac cttcc              55

<210> SEQ ID NO 21
<211> LENGTH: 51
<212> TYPE: DNA
<213> ORGANISM: Artificial
<220> FEATURE:
<223> OTHER INFORMATION: Synthetic

<400> SEQUENCE: 21
cgcgccgagg ttgaggcttt cctgatgact ataaaaatag acttaccttc c                  51

<210> SEQ ID NO 22
<211> LENGTH: 51
<212> TYPE: DNA
<213> ORGANISM: Artificial
<220> FEATURE:
<223> OTHER INFORMATION: Synthetic

<400> SEQUENCE: 22
tgtgtgcaaa tkagccatcc ttccagaggg tcgtgggata attctaagaa a                  51

<210> SEQ ID NO 23
<211> LENGTH: 30
<212> TYPE: DNA
<213> ORGANISM: Artificial
<220> FEATURE:
<223> OTHER INFORMATION: Synthetic

<400> SEQUENCE: 23
tgtgtgcaat cgtgggataa ttctaagaaa                                          30

<210> SEQ ID NO 24
<211> LENGTH: 30
<212> TYPE: DNA
<213> ORGANISM: Artificial
<220> FEATURE:
<223> OTHER INFORMATION: Synthetic

<400> SEQUENCE: 24
cgcgccgagg tgagcaagaa tttctttagc                                          30

<210> SEQ ID NO 25
<211> LENGTH: 32
<212> TYPE: DNA
<213> ORGANISM: Artificial
<220> FEATURE:
<223> OTHER INFORMATION: Synthetic

<400> SEQUENCE: 25
```

-continued aggccacgga cgcgagcaag aatttcttta gc                    32

<210> SEQ ID NO 26
<211> LENGTH: 24
<212> TYPE: DNA
<213> ORGANISM: Artificial
<220> FEATURE:
<223> OTHER INFORMATION: Synthetic

<400> SEQUENCE: 26
attgacgaag gtggaatcac actg                              24

<210> SEQ ID NO 27
<211> LENGTH: 27
<212> TYPE: DNA
<213> ORGANISM: Artificial
<220> FEATURE:
<223> OTHER INFORMATION: Synthetic

<400> SEQUENCE: 27
aggccacgga cgtggaggtc aacgagc                           27

<210> SEQ ID NO 28
<211> LENGTH: 25
<212> TYPE: DNA
<213> ORGANISM: Artificial
<220> FEATURE:
<223> OTHER INFORMATION: Synthetic

<400> SEQUENCE: 28
cgcgccgagg gggaggtcaa cgagc                             25

<210> SEQ ID NO 29
<211> LENGTH: 23
<212> TYPE: DNA
<213> ORGANISM: Artificial
<220> FEATURE:
<223> OTHER INFORMATION: Synthetic

<400> SEQUENCE: 29
gctcagaagg tggaatcaca ctg                               23

<210> SEQ ID NO 30
<211> LENGTH: 27
<212> TYPE: DNA
<213> ORGANISM: Artificial
<220> FEATURE:
<223> OTHER INFORMATION: Synthetic

<400> SEQUENCE: 30
acggacgcgg aggtggaggt caacgag                           27

<210> SEQ ID NO 31
<211> LENGTH: 26
<212> TYPE: DNA
<213> ORGANISM: Artificial
<220> FEATURE:
<223> OTHER INFORMATION: Synthetic

<400> SEQUENCE: 31
cgcgccgagg atggaggtca acgagc                            26

<210> SEQ ID NO 32
<211> LENGTH: 23
<212> TYPE: DNA

```
<213> ORGANISM: Artificial
<220> FEATURE:
<223> OTHER INFORMATION: Synthetic

<400> SEQUENCE: 32
ctcaggaagg tggaatcaca ctg                                              23

<210> SEQ ID NO 33
<211> LENGTH: 25
<212> TYPE: DNA
<213> ORGANISM: Artificial
<220> FEATURE:
<223> OTHER INFORMATION: Synthetic

<400> SEQUENCE: 33
cgcgccgagg agtggaggtc aacga                                            25

<210> SEQ ID NO 34
<211> LENGTH: 26
<212> TYPE: DNA
<213> ORGANISM: Artificial
<220> FEATURE:
<223> OTHER INFORMATION: Synthetic

<400> SEQUENCE: 34
ggccacggac gcgtggaggt caacga                                           26

<210> SEQ ID NO 35
<211> LENGTH: 23
<212> TYPE: DNA
<213> ORGANISM: Artificial
<220> FEATURE:
<223> OTHER INFORMATION: Synthetic

<400> SEQUENCE: 35
tcagtgaagg tggaatcaca ctg                                              23

<210> SEQ ID NO 36
<211> LENGTH: 10
<212> TYPE: DNA
<213> ORGANISM: Artificial
<220> FEATURE:
<223> OTHER INFORMATION: Synthetic

<400> SEQUENCE: 36
cgcgccgagg                                                             10

<210> SEQ ID NO 37
<211> LENGTH: 14
<212> TYPE: DNA
<213> ORGANISM: Artificial
<220> FEATURE:
<223> OTHER INFORMATION: Synthetic

<400> SEQUENCE: 37
atgacgtggc agac                                                        14

<210> SEQ ID NO 38
<211> LENGTH: 12
<212> TYPE: DNA
<213> ORGANISM: Artificial
<220> FEATURE:
<223> OTHER INFORMATION: Synthetic

<400> SEQUENCE: 38
acggacgcgg ag                                                          12
```

```
<210> SEQ ID NO 39
<211> LENGTH: 11
<212> TYPE: DNA
<213> ORGANISM: Artificial
<220> FEATURE:
<223> OTHER INFORMATION: Synthetic

<400> SEQUENCE: 39
tccgcgcgtc c                                                         11

<210> SEQ ID NO 40
<211> LENGTH: 31
<212> TYPE: DNA
<213> ORGANISM: Artificial
<220> FEATURE:
<223> OTHER INFORMATION: Synthetic

<400> SEQUENCE: 40
agtgaagcta gaccaataat tagttcttca c                                   31
```

US 8,911,973 B2

SNAP-BACK PRIMERS AND DETECTABLE HAIRPIN STRUCTURES

The present application is a divisional of U.S. patent application Ser. No. 11/866,663, filed Oct. 3, 2007, which claims priority to U.S. Provisional Patent Application 60/849,280, filed Oct. 4, 2006, each of which is incorporated herein by reference.

FIELD OF THE INVENTION

The present invention provides methods, compositions, and kits comprising snap-back primers used for forming 3' hairpin structures, 5' hairpin structures, and double hairpin structures. The hairpin structures may be used for detecting target sequences (e.g., such as small RNA target sequence), for detecting polymorphisms in target sequences (e.g., such as polymorphisms located near the 5' or 3' ends of the target sequence), or other nucleic acid characterization methods. In certain embodiments, the hairpin structures form invasive cleavage structures (e.g., in combination with a probe or upstream oligonucleotide) which may be cleaved by structure-specific enzymes in order to detect the presence or absence of a particular nucleotide or nucleotide sequence.

BACKGROUND

Interest in the identification and detection of small RNAs has expanded rapidly in the last few years, particularly with the recent discoveries related to microRNAs and small interfering RNAs (siRNA), both of which have a powerful affect on the expression of genes. siRNA molecules, which are generally short, double stranded RNA, are used to silence the expression of specific genes at the post-transcriptional level by a pathway known as RNA interference (RNAi). microRNAs, small regulatory RNA molecules, have been shown to regulate target gene expression in various organisms. siRNA and microRNA molecules generally range between about 15 and 30 nucleotides in length. Other types of small RNAs include small nuclear RNAs (snRNAs) and small nucleolar RNAs (snoRNAs), both of which are involved in mRNA and rRNA processing, as well as tRNAs (about 70-90 bases), and 5S rRNA (about 120 bases), which are both involved in protein translation.

A number of nucleic acid detection technologies, such as INVADER assays and TAQMAN assays, generally require a certain "footprint" for various probes and primers to sit down onto a target nucleic acid in order to detect the target nucleic acid or a specific target nucleotide in the target nucleic acid. This can be problematic if the target nucleic acid itself if very short (e.g., small RNAs), or if the nucleotide to be detected is close to the 5' or 3' end of the target nucleic acid.

What is needed, therefore, are methods, compositions, and kits that allow nucleic acid assays that generally require a "footprint," to be used for detecting targets and target nucleotides when the required footprint is not present in the original target sequence.

SUMMARY OF THE INVENTION

The present invention provides methods, compositions, and kits comprising snap-back primers used for forming 3' hairpin structures, 5' hairpin structures, and double hairpin structures. The present invention also provides methods, kits, and compositions comprising the hairpin structures. The hairpin structures may be used, for example, for detecting target sequences (e.g., such as small RNA target sequence), for detecting polymorphisms in target sequences (e.g., such as polymorphisms located near the 5' or 3' ends of the target sequence), or other nucleic acid characterization methods. In certain embodiments, the hairpin structures form invasive cleavage structures (e.g., in combination with a probe or upstream oligonucleotide) which may be cleaved by structure specific enzymes in order to detect the presence or absence of a particular nucleotide or nucleotide sequence.

In some embodiments, the present invention provides methods for forming a 3' hairpin structure, comprising; a) contacting a sample suspected of containing a target nucleic acid with a snap-back primer and a reverse primer, wherein the snap-back primer comprises: i) a 3' region configured to hybridize to the target nucleic acid such that it can be extended by a polymerase, and ii) a 5' region that is configured to not hybridize to the target nucleic when the 3' region of the snap-back primer is hybridized to the target nucleic acid; and wherein the contacting is under conditions such that: i) the 3' region of the snap-back primer hybridizes to the target nucleic acid and is extended to generate a first amplification product, and ii) the reverse primer hybridizes to the first amplification product and is extended to generate a second amplification product, wherein the second amplification product comprises a 3' snap-back portion capable of hybridizing to a non-adjacent portion of the second amplification product, and b) treating the sample under conditions such that the second amplification product is separated from the first amplification product, and the second amplification product forms a 3' hairpin structure, wherein the 3' hairpin structure comprises: i) the 3' snap-back portion hybridized to the non-adjacent portion; and ii) a 3' terminal portion not hybridized to the second amplification product. In particular embodiments, the 3' snap-back portion is partially complementary to said non-adjacent portion.

In certain embodiments, the 3' hairpin structure comprises a first nucleotide located immediately 5' of the non-adjacent portion, wherein the first nucleotide corresponds to a second nucleotide at a polymorphic position (or other sequence to be interrogated) in the target nucleic acid (e.g., both the first nucleotide in the 3' hairpin structure and the second nucleotide in the target nucleic acid are both "A" as shown in FIG. 1). In other embodiments, the polymorphic position (or other sequence to be interrogated) in the target nucleic acid is located less than 15 bases (e.g., 14, 13, 12, 11, 10, 9, 8, 7, 6, 5, 4, 3, or 2 bases) from the 3' end of the target nucleic acid (e.g., PCR amplicon, siRNA sequence micro RNA sequence, or other relatively short target sequence). In certain embodiments, the target nucleic acid is less than 500 bases in length (e.g., 390 . . . 350 . . . 200 . . . 100 . . . 50 . . . 25 . . . 14), or between 500 and 14 bases in length. In further embodiments, the polymorphic position (or other sequence to be interrogated) in the target nucleic acid (e.g., PCR amplicon, siRNA sequence micro RNA sequence, or other relatively short target sequence) is located between 2 and 5 bases (i.e., 2, 3, 4, or 5) from the 3' end of the target nucleic acid. In certain embodiments, the method further comprises detecting the identity of the first nucleotide, thereby detecting the identity of the second nucleotide at the polymorphic position in the target nucleic acid.

In some embodiments, the target nucleic acid is a small RNA sequence, wherein said small RNA sequence is between 13 and 120 bases in length (e.g., 13 . . . 17 . . . 21 . . . 24 . . . 28 . . . 32 . . . 35 . . . 60 . . . 80 . . . 95 . . . or 120 bases in length). In other embodiments, the target nucleic acid is an miRNA sequence. In other embodiments, the target nucleic acid is selected from the group consisting of: an siRNA sequence, a small nuclear RNA (snRNA), a small nucleolar RNA (snoRNA), a tRNA, and 5S rRNA. In particular embodiments, the target nucleic acid is from a pathogen (e.g., hepatitis C virus). In additional embodiments, the target nucleic acid is part of a cystic fibrosis or cyctochrome p450 gene. In other embodiments, the target nucleotide to be detected in the target sequence is part of a genetic identity repeat sequence. In particular embodiments, the 3' hairpin structures is between 30 and 300 nucleotides in length (e.g., 30 . . . 80 . . . 150 . . . 200 . . . 250 . . . or 300).

In other embodiments, the identity of the first nucleotide is detected using a downstream probe comprising a 3' region configured to hybridize to the 3' hairpin structure and a 5' region configured to not hybridize to the 3' hairpin structure. In particular embodiments, the downstream probe hybridizes to the 3' hairpin structure immediately 5' of the non-adjacent portion thereby forming an invasive cleavage structure. In some embodiments, the invasive cleavage structure is cleaved with a structure specific enzyme (e.g., a FEN-1 enzyme). In some embodiments, the downstream probe comprises a label.

The present invention is not limited by the particular temperature employed during assays of the present invention. In certain embodiments, the invasive cleavage structures is formed between 10 and 95 degrees Celsius (e.g., 10 . . . 20 . . . 30 . . . 40 . . . 50 . . . 60 . . . 70 . . . 80 . . . 90 . . . 95). In other embodiments, the invasive cleavage structure is formed at a temperature between 70 degrees Celsius and 95 degrees Celsius (e.g., 70 . . . 80 . . . 90 . . . or 95 degrees Celsius). In certain embodiments, the invasive cleavage structure formed between 70 and 95 degrees Celsius is cleaved by a thermostable structure specific enzyme (e.g., *Methanocaldococcus jannaschii* FEN1).

In other embodiments, the 3' region of the snap-back primer comprises a sequence capable of hybridizing to the non-adjacent portion of the second amplification product. In particular embodiments, such hybridizing involves complete complementarity between the 3' region of the snap-back primer and the non-adjacent portion of the second amplification product. In other embodiments, such hybridizing involves partial complementarity between the 3' region of the snap-back primer and the non-adjacent portion of the second amplification product (e.g., if the 3' region of the snap-back primer and the non-adjacent portion of the second amplification product are each 10 bases in length, there may be 1, 2, 3, 4, 5, 6, 7, 8, or 9 mis-matched bases). In further embodiments, the 3' region of the snap-back primer is not capable of hybridizing to the non-adjacent portion of the second amplification product.

In certain embodiments, the 3' terminal portion of the 3' hairpin structure is less than 10 nucleotides in length (e.g., 9, 8, 7, 6, 5, 4, 3, 2, or 1). In particular embodiments, the 3' terminal portion of the 3' hairpin structure is 1 nucleotide in length.

In additional embodiments, the 3' snap-back portion of the second amplification product is between 2 and 10 bases in length (e.g., 2, 3, 4, 5, 6, 7, 8, 9, or 10 nucleotides in length). In further embodiments, the 3' snap-back portion of the second amplification product is 3, 4, 5 or 6 bases in length.

In further embodiments, the sample comprises a biological sample from a subject (e.g., blood sample, urine sample, semen sample, stool sample, tissue, amniotic fluid, saliva, etc.). In other embodiments, the sample is from a patient suspected of having a disease. In particular embodiments, the sample is a pooled sample of biological material from a plurality of patients (e.g., 2 . . . 10 . . . 100 . . . or 1000 patients).

In particular embodiments, the non-adjacent region is separated from the snap-back portion by one nucleotide, two nucleotides, three nucleotide or more. In further embodiments, the non-adjacent region is separated from the snap-back portion by at least 10 nucleotides (e.g., 10, 11, 12, 13, 14, 15, 16, 17, 18, 19, 20, or more). In certain embodiments, the non-adjacent region is separated from the snap-back portion by at least 25 nucleotides (e.g., 25 . . . 30 . . . 35 . . . 40 . . . 45 . . . 50 . . . 100 . . . 150 . . . 200 or more). In some embodiments, the region between the snap-back portion and the non-adjacent portion contains sequence that would interfere with a desired detection assay (e.g., contains secondary structure that makes the region inaccessible or contains a multiple polymorphic positions to be detected that would cause prior art assays components to interfere with each other). In particular embodiments, the region between the snap-back portion and the non-adjacent portion contains a base or stretch of bases that would interfere with hybridization of a nucleic acid sequence (e.g., upstream oligonucleotide or downstream probe) if no hairpin were formed.

In some embodiments, the present invention provides methods for forming a 5' hairpin structure, comprising; a) contacting a sample suspected of containing a target nucleic acid with a snap-back primer comprising: i) a 3' region configured to hybridize to the target nucleic acid such that it can be extended by a polymerase, and ii) a 5' region that is configured to not hybridize to the target nucleic acid when the 3' region of the snap-back primer is hybridized to the target nucleic acid; and wherein the contacting is under conditions such that the 3' region of the snap-back primer hybridizes to the target nucleic acid and is extended to generate an amplification product, wherein the amplification product comprises a 5' snap-back portion capable of hybridizing to a non-adjacent portion of the amplification product, and b) treating the sample under conditions such that the amplification product is separated from the target nucleic acid, and the amplification product forms a 5' hairpin structure, wherein the 5' hairpin structure comprises: i) the 5' snap-back portion hybridized to the non-adjacent portion, and ii) a 5' terminal portion that is not hybridized to the amplification product. In particular embodiments, the 5' snap-back portion is partially complementary to said non-adjacent portion.

In particular embodiments, the 3' terminal nucleotide of the non-adjacent portion of the amplification product corresponds to, and is complementary to, a target nucleotide at a polymorphic position in the target nucleic acid (e.g., the 3' terminal nucleotide of the non-adjacent portion is a "G" and the target nucleotide in the target nucleic acid is a "C" as shown in bold and underline in FIG. 3). In further embodiments, the polymorphic position (or other sequence to be interrogated) in the target nucleic acid (e.g., PCR amplicon, siRNA sequence micro RNA sequence, or other relatively short target sequence) is located less than 15 bases from the 3' end of the target nucleic acid (e.g., 14, 13, 12, 11, 10, 9, 8, 7, 6, 5, 4, 3, or 2). In particular embodiments, the target nucleic acid is less than 500 bases in length (e.g., 490 . . . 350 . . . 200 . . . 100 . . . 50 . . . 25 . . . 14), or between 500 and 14 bases in length. In certain embodiments, the polymorphic position (or other sequence to be interrogated) in the target nucleic acid (e.g., PCR amplicon, siRNA sequence micro RNA sequence, or other relatively short target sequence) is located between 2 and 5 bases (i.e., 2, 3, 4, or 5) from the 3' end of the target nucleic acid. In additional embodiments, the methods further comprise detecting the identity of the 3' terminal nucleotide of the non-adjacent portion, thereby detecting the identity of the target nucleotide at the polymorphic position in the target nucleic acid.

In some embodiments, the target nucleic acid is a small RNA sequence, wherein the small RNA sequence is between 13 and 35 bases in length (e.g., 13, 14, 15, 16, 17, 18, 19, 20, 21, 22, 23, 24, 25, 26, 27, 28, 29, 30, 31, 32, 33, 34, or 35 bases in length). In other embodiments, the target nucleic acid is an miRNA sequence. In other embodiments, the target nucleic acid is selected from the group consisting of: an siRNA sequence, a small nuclear RNA (snRNA), a small nucleolar RNA (snoRNA), a tRNA, and 5S rRNA. In particular embodiments, the 5' hairpin structures is between 30 and 300 nucleotides in length (e.g., 30 . . . 80 . . . 150 . . . 200 . . . 250 . . . or 300).

In some embodiments, the identity of the 3' terminal nucleotide is detected using an upstream probe comprising a 5' region configured to hybridize to the amplification product and a 3' region configured to not hybridize to the amplification product. In other embodiments, the upstream probe hybridizes to the amplification product immediately 3' of the non-adjacent portion thereby forming an invasive cleavage structure. In some embodiments, the invasive cleavage structure is cleaved with a structure specific enzyme (e.g., a FEN-1 enzyme). In other embodiments, the upstream probe comprises a label. In particular embodiments, the invasive cleavage structure is formed at a temperature between 70 degrees Celsius and 95 degrees Celsius (e.g., 70 . . . 75 . . . 80 . . . 85 . . . 90 . . . or 95 degrees Celsius). In certain embodiments, the invasive cleavage structure formed between 70 and 95 degrees Celsius is cleaved by a thermostable structure specific enzyme (e.g., *Methanocaldococcus jannaschii* FEN1).

In some embodiments, the 3' region of the snap-back primer comprises a sequence capable of hybridizing to the complement of the non-adjacent portion of the amplification product. In particular embodiments, such hybridizing involves complete complementarity between the 3' region of the snap-back primer and the complement of the non-adjacent portion. In other embodiments, such hybridizing involves partial complementarity between the 3' region of the snap-back primer and the complement of the non-adjacent portion (e.g., if the 3' region of the snap-back primer and the complement of the non-adjacent portion are each 10 bases in length, there may be 1, 2, 3, 4, 5, 6, 7, 8, or 9 mis-matched bases). In other embodiments, the 3' region of the snap-back primer is not capable of hybridizing to the complement of the non-adjacent portion of the amplification product.

In additional embodiments, the 5' terminal portion of the 5' hairpin structure is between 10 and 30 bases in length (e.g., 10, 11, 12, 13, 14, 15, 16, 17, 18, 19, 20, 21, 22, 23, 24, 25, 26, 27, 28, 29, or 30 bases in length). In other embodiments, the 5' terminal portion of the 5' hairpin structure is between 15 and 25 bases in length. In some embodiments, the 5' region of the snap-back primer is between 8 and 15 nucleotides in length (e.g., 8, 9, 10, 11, 12, 13, 14, or 15 nucleotides). In other embodiments, the 5' snap-back portion of the amplification product is between 2 and 15 nucleotides in length (e.g., 2, 3, 4, 5, 6, 7, 8, 9, 10, 11, 12, 13, 14, or 15 nucleotides). In further embodiments, the 5' snap-back portion of the amplification product is between 10 and 12 nucleotides in length.

In further embodiments, the sample comprises a biological sample from a subject (e.g., blood sample, urine sample, semen sample, stool sample, etc.). In other embodiments, the sample is from a patient suspected of having a disease. In particular embodiments, the sample is a pooled sample of biological material from a plurality of patients (e.g., 2 . . . 10 . . . 100 . . . or 1000 patients).

In certain embodiments, the target nucleic acid comprises un-amplified genomic nucleic acid. In additional embodiments, the target nucleic acid is the product of amplification (e.g., by PCR) of an original sequence using, for example, the snap-back primer and one additional primer prior to step a). In particular embodiments, the hairpin structures are formed during PCR amplification of the original target sequence (e.g., the methods are carried out simultaneously with on-going PCR or other amplification). In additional embodiments, such simultaneous methods are carried out in isothermal conditions (e.g., at 72 degrees Celsius).

In some embodiments, the present invention provides methods for forming a double hairpin structure, comprising; a) contacting a sample suspected of containing a target nucleic acid with a forward snap-back primer and a reverse snap-back primer, wherein the forward snap-back primer comprises: i) a 3' region configured to hybridize to the target nucleic acid such that it can be extended by a polymerase to generate a first amplification product, and ii) a 5' region that is configured to not hybridize to the target nucleic acid when the 3' region of the forward snap-back primer is hybridized to the target nucleic acid; wherein the reverse snap-back primer comprises: i) a 3' region configured to hybridize to the first amplification product such that it can be extended by a polymerase, and ii) a 5' region that is configured to not hybridize to the first amplification product when the 3' region of the reverse snap-back primer is hybridized to the first amplification product; and wherein the contacting is under conditions such that: i) the 3' region of the forward snap-back primer hybridizes to the target nucleic acid and is extended to generate a first amplification product, and ii) the 3' region of the reverse snap-back primer hybridizes to the first amplification product and is extended to generate a second amplification product, wherein the second amplification product comprises: A) a 3' snap-back portion capable of hybridizing to a first non-adjacent portion of the second amplification product; and B) a 5' snap-back portion capable of hybridizing to a second non-adjacent portion of the second amplification product, wherein the second non-adjacent portion is 5' of the first non-adjacent portion, and b) treating the sample under conditions such that the second amplification product is separated from the first amplification product, and the second amplification product forms a double hairpin structure, wherein the double hairpin structure comprises: i) the 3' snap-back portion hybridized to the first non-adjacent portion, ii) the 5' snap-back portion hybridized to the second non-adjacent portion, and iii) a 5' terminal portion that is not hybridized to the second amplification product.

In other embodiments, the double hairpin structure further comprises: iv) a 3' terminal portion not hybridized to the second amplification product. In additional embodiments, the second non-adjacent portion is immediately 5' of the first non-adjacent portion. In some embodiments, the 3' terminal nucleotide of the second non-adjacent portion corresponds to a target nucleotide at a polymorphic position (or other sequence to be interrogated) in the target nucleic acid (e.g., the 3' terminal nucleotide of the second non-adjacent portion and the target nucleotide in the target nucleic acid are both "A" as shown in FIG. 5). In further embodiments, the polymorphic position (or other sequence to be interrogated) in the target nucleic acid (e.g., PCR amplicon, siRNA sequence micro RNA sequence, or other relatively short target sequence) is located less than 15 bases from the 3' end of the target nucleic acid (e.g., 14, 13, 12, 11, 10, 9, 8, 7, 6, 5, 4, 3, or 2 bases). In certain embodiments, the target nucleic acid is less than 500 bases in length (e.g., 490 . . . 350 . . . 200 . . . 100 . . . 50 . . . 25 . . . 14), or between 500 and 14 bases in length. In other embodiments, the polymorphic position (or other sequence to be interrogated) in the target nucleic acid (e.g., PCR amplicon, siRNA sequence micro RNA sequence, or other relatively short target sequence) is located between 2 and 5 bases (i.e., 2, 3, 4, or 5 bases) from the 3' end of the target nucleic acid.

In some embodiments, the methods further comprise detecting the identity of the 3' terminal nucleotide of the second non-adjacent portion, thereby detecting the identity of the target nucleotide at the polymorphic position in the target nucleic acid. In further embodiments, the identity of the 3' terminal nucleotide of the second non-adjacent portion is detected using a downstream probe comprising a 3' region configured to hybridize to the double hairpin structure and a 5' region configured to not hybridize to the double hairpin structure. In particular embodiments, the downstream probe hybridizes to the double hairpin structure immediately 5' of the first non-adjacent portion thereby forming an invasive cleavage structure. In some embodiments, the invasive cleavage structure is cleaved with a structure specific enzyme (e.g., a FEN-1 enzyme). In particular embodiments, the invasive cleavage structure is formed at a temperature between 70 degrees Celsius and 95 degrees Celsius (e.g., 70 . . . 75 . . . 80 . . . 85 . . . 90 . . . or 95 degrees Celsius). In certain embodiments, the invasive cleavage structure formed between 70 and 95 degrees Celsius is cleaved by a thermostable structure specific enzyme (e.g., *Methanocaldococcus jannaschii* FEN1). In particular embodiments, the double hairpin structures is between 30 and 300 nucleotides in length (e.g., 30 . . . 80 . . . 150 . . . 200 . . . 250 . . . or 300).

In other embodiments, the identity of the 3' terminal nucleotide of the second non-adjacent region is detected using an upstream probe comprising a 5' region configured to hybridize to the double hairpin structure and a 3' region configured to not hybridize to the double hairpin structure. In additional embodiments, the upstream probe hybridizes to the double hairpin structure immediately 3' of the second non-adjacent portion thereby forming an invasive cleavage structure. In further embodiments, the second non-adjacent portion is immediately 5' of the first non-adjacent portion, and wherein the double hairpin structure further comprises a 3' terminal portion that is not hybridized to the second amplification product and that overlaps with the 5' terminal portion of the double hairpin structure thereby forming an invasive cleavage structure.

In certain embodiments, the 3' region of the forward snap-back primer comprises a sequence capable of hybridizing to the first non-adjacent portion of the second amplification product. In other embodiments, the 3' region of the forward snap-back primer is not capable of hybridizing to the first non-adjacent portion of the second amplification product. In some embodiments, the 3' terminal portion of the double hairpin structure is less than 10 nucleotides in length (e.g., 9, 8, 7, 6, 5, 4, 3, 2, or 1 nucleotide in length). In further embodiments, the 3' terminal portion of the double hairpin structure is 1 nucleotide in length. In other embodiments, the 3' snap-back portion of the second amplification product is between 5 and 10 bases in length. In additional embodiments, the 3' snap-back portion of the second amplification product is between 5 and 6 bases in length. In certain embodiments, the 5' region of the reverse snap-back primer is between 8 and 15 nucleotides in length. In other embodiments, the 5' snap-back portion of the second amplification product is between 8 and 15 nucleotides in length. In particular embodiments, the 5' snap-back portion of the second amplification product is between 10 and 12 nucleotides in length.

In further embodiments, the target nucleic acid comprises un-amplified genomic nucleic acid. In other embodiments, the target nucleic acid is the product of amplification of an original sequence using the forward snap-back and the reverse snap-back primers prior to step a). In particular embodiments, the hairpin structures are formed during PCR amplification of the original target sequence (e.g., the methods are carried out simultaneously with on-going PCR or other amplification). In additional embodiments, such simultaneous methods are carried out in isothermal conditions.

In some embodiments, the present invention provides compositions for generating a 3' hairpin structure from a target nucleic acid comprising: a snap-back primer and a reverse primer, wherein the snap-back primer comprises: i) a 3' region configured to hybridize to the target nucleic acid such that it can be extended by a polymerase to generate a first amplification product, and ii) a 5' region that is configured to not hybridize to the target nucleic when the 3' region of the snap-back primer is hybridized to the target nucleic acid; and wherein the reverse primer comprises a 3' region configured to hybridize to the first amplification product such that it can be extended by a polymerase to generate a second amplification product comprising a 3' snap-back portion capable of hybridizing to a non-adjacent portion of the second amplification product to form a 3' hairpin structure, wherein the 3' hairpin structure comprises a 3' terminal portion configured to not hybridize to the second amplification product.

In particular embodiments, the compositions further comprise the 3' hairpin structure. In other embodiments, the compositions further comprise the target nucleic acid. In some embodiments, the first amplification product is 500 nucleotides in length or less (e.g., 500 . . . 400 . . . 300 . . . 200 . . . 150 . . . 100 . . . 80 . . . 50 . . . or 40 nucleotides in length). In other embodiments, the compositions further comprise a structure specific enzyme.

In additional embodiments, the 3' hairpin structure comprises a first nucleotide located immediately 5' of the non-adjacent portion, wherein the first nucleotide corresponds to a second nucleotide at a polymorphic position (or other sequence to be interrogated) in the target nucleic acid. In further embodiments, the polymorphic position (or other sequence to be interrogated) in the target nucleic acid (e.g., PCR amplicon, siRNA sequence micro RNA sequence, or other relatively short target sequence) is located less than 15 bases from the 3' end of the target nucleic acid. In certain embodiments, the target nucleic acid is less than 500 bases in length (e.g., 490 . . . 350 . . . 200 . . . 100 . . . 50 . . . 25 . . . 14), or between 500 and 14 bases in length. In some embodiments, the polymorphic position in the target nucleic acid is located between 2 and 5 bases (i.e., 2, 3, 4, or 5 bases) from the 3' end of the target nucleic acid. In certain embodiments, the 3' terminal portion of the 3' hairpin structure is less than 10 nucleotides in length (e.g., 9, 8, 7, 6, 5, 4, 3, 2, or 1 bases). In other embodiments, the 3' terminal portion of the 3' hairpin structure is 1 nucleotide in length. In particular embodiments, the 3' snap-back portion of the second amplification product is between 2 and 10 bases in length (e.g., 2, 3, 4, 5, 6, 7, 8, 9, or 10 bases). In other embodiments, the 3' snap-back portion of the second amplification product is 5 or 6 bases in length.

In particular embodiments, the target nucleic acid comprises genomic nucleic acid. In certain embodiments, the target nucleic acid comprises human genomic nucleic acid. In further embodiments, the target nucleic acid comprises amplified nucleic acid. In additional embodiments, the target nucleic acid is the product of amplification of an original sequence using the forward snap-back primer and the reverse snap-back primer prior to step a). In particular embodiments, the compositions further comprise a polymerase.

In some embodiments, the present invention provides compositions for generating a 5' hairpin structure from a target nucleic acid comprising: a snap-back primer, wherein the snap-back primer comprises: i) a 3' region configured to hybridize to the target nucleic acid such that it can be extended by a polymerase to generate a first amplification product, and ii) a 5' region that is configured to not hybridize to the target nucleic when the 3' region of the snap-back primer is hybridized to the target nucleic acid; and wherein the amplification product comprises a 5' snap-back portion capable of hybridizing to a non-adjacent portion of the second amplification product to form a 5' hairpin structure, wherein the 5' hairpin structure comprises a 5' terminal portion not hybridized to the amplification product.

In particular embodiments, the compositions further comprise the 5' hairpin structure. In other embodiments, the compositions further comprise the target nucleic acid. In some embodiments, the amplification product is 500 nucleotides in length of less (e.g., 500 . . . 300 . . . 100 . . . or 50 nucleotides in length). In additional embodiments, the compositions further comprise a structure specific enzyme.

In other embodiments, the 3' terminal nucleotide of the non-adjacent portion of the amplification product corresponds to a target nucleotide at a polymorphic position in the target nucleic acid. In further embodiments, the polymorphic position in the target nucleic acid (e.g., PCR amplicon, siRNA sequence micro RNA sequence, or other relatively short target sequence) is located less than 15 bases from the 3' end of the target nucleic acid. In certain embodiments, the target nucleic acid is less than 500 bases in length (e.g., 490 . . . 350 . . . 200 . . . 100 . . . 50 . . . 25 . . . 14), or between 500 and 14 bases in length. In other embodiments, the polymorphic position in the target nucleic acid is located between 2 and 5 bases from the 3' end of the target nucleic acid. In additional embodiments, the 5' terminal portion of the 5' hairpin structure is between 10 and 30 bases in length. In other embodiments, the 5' terminal portion of the 5' hairpin structure is between 15 and 25 bases in length. In some embodiments, the 5' snap-back portion of the amplification product is between 5 and 10 bases in length. In particular embodiments, the 5' snap-back portion of the amplification product is 5 or 6 bases in length. In other embodiments, the target nucleic acid comprises genomic nucleic acid. In further embodiments, the target nucleic acid comprises human genomic nucleic acid.

In additional embodiments, the target nucleic acid comprises amplified nucleic acid. In certain embodiments, the compositions further comprise a polymerase. In some embodiments, the target nucleic acid is a small RNA sequence, wherein said small RNA sequence is between 13 and 35 bases in length (e.g., 13 . . . 17 . . . 21 . . . 24 . . . 28 . . . 32 . . . or 35 bases in length). In other embodiments, the target nucleic acid is an miRNA sequence. In further embodiments, the target nucleic acid is selected from the group consisting of: an siRNA sequence, a small nuclear RNA (snRNA), a small nucleolar RNA (snoRNA), a tRNA, and 5S rRNA.

In other embodiments, the present invention provides compositions for generating a double hairpin structure from a target nucleic acid comprising: a forward snap-back primer and a reverse snap-back primer, wherein the forward snap-back primer comprises: i) a 3' region configured to hybridize to a target nucleic acid such that it can be extended by a polymerase to generate a first amplification product, and ii) a 5' region that is configured to not hybridize to the target nucleic when the 3' region of the forward snap-back primer is hybridized to the target nucleic acid; and wherein the reverse snap-back primer comprises: i) a 3' region configured to hybridize to the first amplification product such that it can be extended by a polymerase to generate a second amplification product, and ii) a 5' region that is configured to not hybridize to the first amplification product when the 3' region of the reverse snap-back primer is hybridized to the first amplification product; wherein the second amplification product is configured to form the double hairpin structure and comprises: i) a 3' snap-back portion capable of hybridizing to a non-adjacent portion of the second amplification product, and ii) a 5' snap-back portion capable of hybridizing to a second non-adjacent portion of the second amplification product, wherein the second non-adjacent portion is 5' of the first non-adjacent portion.

In some embodiments, the present invention provides methods for detecting the presence or absence of a specific nucleotide at two closely spaced polymorphic positions in a target nucleic acid, comprising; a) providing a sample containing a target nucleic acid comprising: i) a first target nucleotide at a first polymorphic position, and ii) a second target nucleotide at a second polymorphic position, wherein the first and second polymorphic positions are within six bases of each other (e.g., within 6, 5, 4, 3, 2, or immediately adjacent to each other); b) contacting the sample with: i) a first snap-back primer comprising a first primer nucleotide, i) a second snap-back primer comprising a second primer nucleotide, ii) a polymerase, iii) first and second upstream oligonucleotides, and iv) a structure specific cleavage enzyme; wherein the contacting is under conditions such that: i) first and second 5' hairpin structures are generated, ii) the first 5' hairpin structure and the first upstream oligonucleotide form a first invasive cleavage structure that is cleaved by the structure specific enzyme if the first target nucleotide hybridizes to the first primer nucleotide, and iii) the second 5' hairpin structure and the second upstream oligonucleotide form a second invasive cleavage structure that is cleaved by the structure specific enzyme if the second target nucleotide hybridizes to the second primer nucleotide.

In particular embodiments, the first and second polymorphic positions are within three bases of each other. In other embodiments, the first and second polymorphic positions are adjacent to each other. In some embodiments, the target nucleic acid further comprises a third target nucleotide at a third polymorphic position, wherein the third polymorphic position is within four bases of the first polymorphic position, and wherein the sample is further contacted with: a third snap-back primer comprising a third primer nucleotide, and ii) a third upstream oligonucleotide, and wherein the contacting is further under conditions such that: i) a third 5' hairpin structure is generated, and ii) the third 5' hairpin structure and the third upstream oligonucleotide form a third invasive cleavage structure that is cleaved by the structure specific enzyme if the third target nucleotide hybridizes to the third primer nucleotide.

In some embodiments, the present invention provides compositions (e.g., kits, reaction mixtures, etc.) comprising: a) first snap-back primer configured to form a first 5' hairpin structure when extended by a polymerase on a target nucleic acid, wherein the first 5' hairpin structure is configured for detecting a first target nucleotide at a first polymorphic position in the target nucleic acid; and b) a second snap-back primer configured to form a second 5' hairpin structure when extended by a polymerase on the target nucleic acid, wherein the second 5' hairpin structure is configured for detecting a second target nucleotide at a second polymorphic position in the target nucleic acid. In particular embodiments, the second polymorphic position is within 10 bases of the first polymorphic position (e.g., within 10, 9, 8, 7, 6, 5, 4, 3, 2, or adjacent to each other).

In other embodiments, the present invention provides compositions further comprising: c) a third snap-back primer configured to form a third 5' hairpin structure when extended by a polymerase on the target nucleic acid, wherein the third 5' hairpin structure is configured for detecting a third target nucleotide at a third polymorphic position in the target nucleic acid. In particular embodiments, the third polymorphic position is within 10 bases of the first polymorphic position.

In other embodiments, the present invention provides methods further comprising: d) a fourth snap-back primer configured to form a fourth 5' hairpin structure when extended by a polymerase on the target nucleic acid, wherein the fourth 5' hairpin structure is configured for detecting a fourth target nucleotide at a fourth polymorphic position in the target nucleic acid. In additional embodiments, the fourth polymorphic position is within 10 bases of the first polymorphic position. In other embodiments, the second polymorphic position is within 10 bases of the first polymorphic position (e.g., within 10, 9, 8, 7, 6, 5, 4, 3, 2, or adjacent to each other).

In some embodiments, the present invention provides compositions comprising a double hairpin structure, wherein the double hairpin structure comprises: i) a first non-adjacent portion, ii) a second non-adjacent portion that is 5' of the first non-adjacent portion, iii) a 3' snap-back portion hybridized to the first non-adjacent portion, iv) a 5' snap-back portion hybridized to the second non-adjacent portion, v) a 5' terminal portion that is not hybridized to the double hairpin structure, and iv) a 3' terminal portion that is not hybridized to the double hairpin structure.

In further embodiments, the double hairpin structure is cleavable by a structure specific enzyme. In particular embodiments, the compositions further comprise a structure specific enzyme. In some embodiments, the first non-adjacent portion is between 4 and 6 bases in length. In other embodiments, the second non-adjacent portion is between 9 and 13 bases in length. In additional embodiments, the second non-adjacent portion is immediately 5' of the first non-adjacent portion. In other embodiments, the 3' terminal nucleotide of the second non-adjacent portion corresponds to a polymorphic position in a target nucleic acid. In some embodiments, the polymorphic position in the target nucleic acid (e.g., PCR amplicon, siRNA sequence micro RNA sequence, or other relatively short target sequence) is located less than 15 bases from the 3' end of the target nucleic acid. In certain embodiments, the target nucleic acid is less than 500 bases in length (e.g., 490 . . . 350 . . . 200 . . . 100 . . . 50 . . . 25 . . . 14), or between 500 and 14 bases in length. In additional embodiments, the polymorphic position in the target nucleic acid is located between 2 and 5 bases from the 3' end of the target nucleic acid.

In certain embodiments, the double hairpin structure comprises an invasive cleavage structure. In other embodiments, the double hairpin structure comprises an invasive cleavage structure when at a temperature between 70 degrees Celsius and 95 degrees Celsius. In some embodiments, the 3' terminal portion of the double hairpin structure is less than 10 nucleotides in length. In certain embodiments, the 3' terminal portion of the double hairpin structure is 1 nucleotide in length. In other embodiments, the length of the double hairpin structure is 200 bases or less (e.g., 200 . . . 150 . . . 100 . . . 80 . . . 70 . . . 60 . . . 50 . . . or 40).

In some embodiments, the present invention provides compositions comprising a 3' hairpin structure, wherein the 3' hairpin structure comprises: a) a non-adjacent portion, b) a 3' snap-back portion hybridized to the non-adjacent portion, wherein the 3' snap-back portion is between 4 and 8 bases in length, c) a 3' terminal portion that is not hybridized to the 3' hairpin structure, and d) a first nucleotide immediately 5' of the non-adjacent portion, wherein the nucleotide corresponds to a second nucleotide at a polymorphic position in a target nucleic acid.

In certain embodiments, the 3' terminal portion of the 3' hairpin structure is less than 10 nucleotides in length. In other embodiments, the compositions further comprise a structure specific enzyme. In particular embodiments, the 3' terminal portion of the 3' hairpin structure is 1 nucleotide in length. In further embodiments, the length of the 3' hairpin structure is 150 bases or less (e.g., 150 . . . 125 . . . 100 . . . 75 . . . 50 . . . or 40 bases).

In some embodiments, the compositions further comprise a downstream probe, wherein the downstream probe comprises: i) a 3' region configured to hybridize to the 3' hairpin structure immediately 5' of the non-adjacent portion, and ii) a 5' region configured to not hybridize to the 3' hairpin structure. In other embodiments, the compositions further comprise a 5' hairpin structure, wherein the 5' hairpin structure comprises: a) a non-adjacent portion, wherein the 3' terminal nucleotide of the non-adjacent portion corresponds to a polymorphic position in a target nucleic acid, b) a 5' snap-back portion hybridized to the non-adjacent portion, wherein the 5' snap-back portion is between 8 and 14 bases in length, and c) a 5' terminal portion that is not hybridized to the 5' hairpin structure. In additional embodiments, the compositions further comprise a structure specific enzyme.

In certain embodiments, the length of the 5' hairpin structure is 150 bases or less (e.g., 150 . . . 125 . . . 100 . . . 75 . . . or 40 bases). In other embodiments, the compositions further comprise an upstream oligonucleotide, wherein the upstream oligonucleotide comprises: i) a 5' region configured to hybridize to the 5' hairpin structure immediately 3' of the non-adjacent portion, and ii) a 3' region configured to not hybridize to the 5' hairpin structure.

In other embodiments, the present invention provides kits for forming an invasive cleavage structure, comprising: a) a snap-back primer and a reverse primer configured to amplify a target sequence in order to generate a 3' hairpin structure, and b) a downstream probe configured to form an invasive cleavage structure with the 3' hairpin structure, wherein the downstream probe comprises: i) a 3' region configured to hybridize to the 3' hairpin structure, and ii) a 5' region configured to not hybridize to the 5' hairpin structure. In further embodiments, the invasive cleavage structure may be cleaved by a structure specific enzyme in order to detect a target nucleotide at a polymorphic position in the target nucleic acid. In some embodiments, the 3' hairpin structure comprises a first nucleotide that corresponds to the target nucleotide in the target nucleic acid. In particular embodiments, the downstream probe is configured to hybridize to the 3' hairpin structure such that the 5' terminal base of the 3' region of the downstream probe is hybridized to the first nucleotide. In other embodiments, the compositions further comprise a structure specific enzyme. The some embodiments, the structure specific enzyme is thermostable. In certain embodiments, the structure specific enzyme is a 5' nuclease. In additional embodiments, the structure specific enzyme does, or does not, have polymerase activity. In further embodiments, the structure specific enzyme is a FEN-1 (e.g., thermostable FEN-1). In particular embodiments, the kits further comprise at least one additional reagent selected from: a ligase, a control reagent; a dye; or other reagent generally included in kits for running biological reactions (e.g., buffers, salts, etc.).

In some embodiments, the present invention provides kits for forming an invasive cleavage structure, comprising: a) a snap-back primer configured to form a 5' hairpin structure when extended by a polymerase on a target nucleic acid, and b) an upstream oligonucleotide configured to form an invasive cleavage structure with the 5' hairpin structure, wherein the upstream oligonucleotide comprises: i) a 5' region configured to hybridize to the 5' hairpin structure, and ii) 3' region configured to not hybridize to the 5' hairpin structure. In certain embodiments, the invasive cleavage structure may be cleaved by a structure specific enzyme in order to detect a target nucleotide at a polymorphic position in the target nucleic acid. In other embodiments, the 5' hairpin structure comprises a first nucleotide that corresponds to the target nucleotide at the polymorphic position in the target nucleic acid. In additional embodiments, the upstream oligonucleotide is configured to hybridize to the 5' hairpin structure immediately 3' of the first nucleotide. In some embodiments, the kits further comprise a structure specific enzyme.

In certain embodiments, the present invention provides kits comprising: a) a structure specific enzyme, and b) a snap-back primer and a reverse primer configured to amplify a target sequence in order to generate a 3' hairpin structure. In some embodiments, the structure specific enzyme comprises a FEN-1.

In particular embodiments, the present invention provides kits comprising: a) a structure specific enzyme, and b) a snap-back primer configured to form a 5' hairpin structure when extended by a polymerase on a target nucleic acid.

In some embodiments, the present invention provides kits comprising; a) a first snap-back primer configured to form a first 5' hairpin structure when extended by a polymerase on a target nucleic acid, wherein the first 5' hairpin structure is configured for detecting a first target nucleotide at a first polymorphic position in the target nucleic acid; and b) a second snap-back primer configured to form a second 5' hairpin structure when extended by a polymerase on the target nucleic acid, wherein the second 5' hairpin structure is configured for detecting a second target nucleotide at a second polymorphic position in the target nucleic acid. In particular embodiments, the second polymorphic position is within 5 bases of the first polymorphic position. In other embodiments, the kits further comprise: c) a third snap-back primer configured to form a third 5' hairpin structure when extended by a polymerase on the target nucleic acid, wherein the third 5' hairpin structure is configured for detecting a third target nucleotide at a third polymorphic position in the target nucleic acid. In additional embodiments, the third polymorphic position is within 5 bases of the first polymorphic position. In some embodiments, the kits further comprise: d) a fourth snap-back primer configured to form a fourth 5' hairpin structure when extended by a polymerase on the target nucleic acid, wherein the fourth 5' hairpin structure is configured for detecting a fourth target nucleotide at a fourth polymorphic position in the target nucleic acid. In other embodiments, the fourth polymorphic position is within 8 bases of the first polymorphic position. In particular embodiments, the kits further comprise a polymerase. In other embodiments, the kits further comprise first and second upstream oligonucleotides. In additional embodiments, the kits further comprise a structure specific cleavage enzyme.

In some embodiments, the present invention provides kits comprising: a) a forward snap-back primer configured to amplify a target sequence in order to generate a first amplification product, b) a reverse snap-back primer configured to form a second amplification product when extended by a polymerase on the first amplification product, wherein the second amplification product comprises: A) a 3' snap-back portion capable of hybridizing to a first non-adjacent portion of the second amplification product; and B) a 5' snap-back portion capable of hybridizing to a second non-adjacent portion of the second amplification product, wherein the second non-adjacent portion is 5' of the first non-adjacent portion, and wherein the second amplification product is configured to form a double hairpin structure, wherein the double hairpin structure comprises: i) the 3' snap-back portion hybridized to the first non-adjacent portion, ii) the 5' snap-back portion hybridized to the second non-adjacent portion, and iii) a 5' terminal portion that is not hybridized to the second amplification product.

In certain embodiments, the present invention provides kits comprising: a) a reverse primer, b) a first snap-back primer configured to amplify a target sequence in conjunction with the reverse primer in order to generate a first 3' hairpin structure; and c) a second snap-back primer configured to amplify the target sequence in conjunction with the reverse primer in order to generate a second 3' hairpin structure. In other embodiments, the first 3' hairpin structure is configured for detecting a first target nucleotide at a first polymorphic position in the target nucleic acid, and the second 3' hairpin structure is configured for detecting a second target nucleotide at a second polymorphic position in the target nucleic acid.

In some embodiments, the target nucleic acid is a small RNA sequence, wherein said small RNA sequence is between 13 and 35 bases in length (e.g., 13 ... 17 ... 21 ... 24 ... 28 ... 32 ... or 35 bases in length). In other embodiments, the target nucleic acid is an miRNA sequence. In other embodiments, the target nucleic acid is selected from the group consisting of: an siRNA sequence, a small nuclear RNA (snRNA), a small nucleolar RNA (snoRNA), a tRNA, and 5S rRNA.

In certain embodiments, the present invention provides methods for forming a cleavage structure, comprising; a) contacting a sample suspected of containing a target nucleic acid with a forward primer and a reverse primer in order to generate an amplification product, wherein the amplification product comprises a first portion capable of hybridizing to a second portion of the amplification product; and b) treating the sample under conditions such that the first portion hybridizes to the second portion to generate an invasive cleavage structure. In particular embodiments, the methods further comprise adding a probe that participates in the formation of the cleavage structure. In other embodiments, the first portion is at or near the 3' end of the target nucleic acid. In certain embodiments, the first portion is at or near the 5' end of the target nucleic acid. In some embodiments, the amplification product comprises a third portion capable of hybridizing to a fourth portion of the amplification product. In additional embodiments, the second portion and the forth portion are adjacent to each other.

In certain embodiments, the present invention provides methods for forming a 3' hairpin structure, comprising; a) contacting a sample suspected of containing a target nucleic acid with a oligonucleotide comprising a 3' snap-back portion capable of hybridizing to a non-adjacent portion of the target nucleic acid, b) ligating the oligonucleotide to the 3' end of the target nucleic acid to generate an extended target sequence, and c) treating the sample under conditions such that the extended target sequence forms a 3' hairpin structure, wherein the 3' hairpin structure comprises: i) the 3' snap-back portion hybridized to the non-adjacent portion; and ii) a 3' terminal portion not hybridized to the extended target sequence. Such methods may be used, for example, in any of the kits, compositions, or methods described above (e.g., rather than primer extension) to generate hairpin structures. In certain embodiments, the ligation is accomplished with a ligase enzyme or a non-template dependent polymerase.

In some embodiments, the present invention provides methods for forming a 5' hairpin structure, comprising; a) contacting a sample suspected of containing a target nucleic acid with a oligonucleotide comprising: i) a 3' portion capable of hybridizing to a non-adjacent portion of the target nucleic acid, and ii) a 5' portion that is configured to not hybridize to the target nucleic acid when the 3' region is hybridized to the target nucleic acid, b) ligating the oligonucleotide to the 5' end of the target nucleic acid to generate an extended target sequence, and c) treating the sample under conditions such that the extended target sequence forms a 5' hairpin structure, wherein the 5' hairpin structure comprises: i) the 3' portion hybridized to the non-adjacent portion; and ii) the 5' portion not hybridized to the extended target sequence. Such methods may be used, for example, in any of the kits, compositions, or methods described above (e.g., rather than primer extension) to generate hairpin structures. In certain embodiments, the ligation is accomplished with a ligase enzyme or a non-template dependent polymerase.

DEFINITIONS

To facilitate an understanding of the present invention, a number of terms and phrases are defined below:

As used herein, the terms "subject" and "patient" refer to any organisms including plants, microorganisms and animals (e.g., mammals such as dogs, cats, livestock, and humans).

The term "label" as used herein refers to any atom or molecule that can be used to provide a detectable (preferably quantifiable) effect, and that can be attached to a nucleic acid or protein. Labels include but are not limited to dyes; radiolabels such as $^{32}$P; binding moieties such as biotin; haptens such as digoxygenin; luminogenic, phosphorescent or fluorogenic moieties; mass tags; and fluorescent dyes alone or in combination with moieties that can suppress ("quench") or shift emission spectra by fluorescence resonance energy transfer (FRET). FRET is a distance-dependent interaction between the electronic excited states of two molecules (e.g., two dye molecules, or a dye molecule and a non-fluorescing quencher molecule) in which excitation is transferred from a donor molecule to an acceptor molecule without emission of a photon. (Stryer et al., 1978, Ann. Rev. Biochem., 47:819; Selvin, 1995, Methods Enzymol., 246:300, each incorporated herein by reference). As used herein, the term "donor" refers to a fluorophore that absorbs at a first wavelength and emits at a second, longer wavelength. The term "acceptor" refers to a moiety such as a fluorophore, chromophore, or quencher that has an absorption spectrum that overlaps the donor's emission spectrum, and that is able to absorb some or most of the emitted energy from the donor when it is near the donor group (typically between 1-100 nm). If the acceptor is a fluorophore, it generally then re-emits at a third, still longer wavelength; if it is a chromophore or quencher, it then releases the energy absorbed from the donor without emitting a photon. In some embodiments, changes in detectable emission from a donor dye (e.g. when an acceptor moiety is near or distant) are detected. In some embodiments, changes in detectable emission from an acceptor dye are detected. In preferred embodiments, the emission spectrum of the acceptor dye is distinct from the emission spectrum of the donor dye such that emissions from the dyes can be differentiated (e.g., spectrally resolved) from each other.

In some embodiments, a donor dye is used in combination with multiple acceptor moieties. In a preferred embodiment, a donor dye is used in combination with a non-fluorescing quencher and with an acceptor dye, such that when the donor dye is close to the quencher, its excitation is transferred to the quencher rather than the acceptor dye, and when the quencher is removed (e.g., by cleavage of a probe), donor dye excitation is transferred to an acceptor dye. In particularly preferred embodiments, emission from the acceptor dye is detected. See, e.g., Tyagi, et al., Nature Biotechnology 18:1191 (2000), which is incorporated herein by reference.

Labels may provide signals detectable by fluorescence (e.g., simple fluorescence, FRET, time-resolved fluorescence, fluorescence polarization, etc.), radioactivity, colorimetry, gravimetry, X-ray diffraction or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral. Labels can include or consist of nucleic acid or protein sequence, so long as the sequence comprising the label is detectable.

In some embodiments a label comprises a particle for detection. In preferred embodiments, the particle is a phosphor particle. In particularly preferred embodiments, the phosphor particle is an up-converting phosphor particle (see, e.g., Ostermayer, F. W. Preparation and properties of infrared-to-visible conversion phosphors. Metall. Trans. 752, 747-755 [1971]). In some embodiments, rare earth-doped ceramic particles are used as phosphor particles. Phosphor particles may be detected by any suitable method, including but not limited to up-converting phosphor technology (UPT), in which up-converting phosphors transfer low energy infrared (IR) radiation to high-energy visible light. While the present invention is not limited to any particular mechanism, in some embodiments the UPT up-converts infrared light to visible light by multi-photon absorption and subsequent emission of dopant-dependant phosphorescence. See, e.g., U.S. Pat. No. 6,399,397, Issued Jun. 4, 2002 to Zarling, et al.; van De Rijke, et al., Nature Biotechnol. 19(3):273-6 [2001]; Corstjens, et al., IEE Proc. Nanobiotechnol. 152(2):64 [2005], each incorporated by reference herein in its entirety.

As used herein, the term "distinct" in reference to signals refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the terms "complementary" or "complementarity" are used in reference to polynucleotides (i.e., a sequence of nucleotides such as an oligonucleotide or a target nucleic acid) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "homology" and "homologous" refers to a degree of identity. There may be partial homology or complete homology. A partially homologous sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr. Thermodynamics and NMR of internal G.T mismatches in DNA. Biochemistry 36, 10581-94 (1997) include more sophisticated computations which take structural and environmental, as well as sequence characteristics into account for the calculation of $T_m$.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified," "mutant" or "polymorphic" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprising two or more deoxyribonucleotides or ribonucleotides, preferably at least 5 nucleotides, more preferably at least about 10-15 nucleotides and more preferably at least about 15 to 30 nucleotides or longer. The exact size will depend on many factors, which in turn depend on the ultimate function or use of the oligonucleotide. The oligonucleotide may be generated in any manner, including chemical synthesis, DNA replication, reverse transcription, PCR, or a combination thereof. In some embodiments, oligonucleotides that form invasive cleavage structures are generated in a reaction (e.g., by extension of a primer in an enzymatic extension reaction).

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "cleavage structure" as used herein, refers to a structure that is formed by the interaction of 1) at least one probe oligonucleotide and a target nucleic acid, or 2) formed by a single nucleic acid sequence when a 5' snap-back portion hybridizes to a non-adjacent portion of the nucleic acid sequence; forming a structure comprising a duplex, the resulting structure being cleavable by a cleavage agent, including but not limited to an enzyme. The cleavage structure is a substrate for specific cleavage by the cleavage agent in contrast to a nucleic acid molecule that is a substrate for non-specific cleavage by agents such as phosphodiesterases which cleave nucleic acid molecules without regard to secondary structure (i.e., no formation of a duplexed structure is required).

The term "invasive cleavage structure" as used herein refers to a cleavage structure comprising i) a target nucleic acid, ii) an upstream nucleic acid (e.g., an INVADER oligonucleotide, or a 3' snap-back portion hybridized to a non-adjacent portion of an amplification product), and iii) a downstream nucleic acid (e.g., a probe, or a 5' snap-back portion hybridized to a non-adjacent portion of an amplification product), where the upstream and downstream nucleic acids anneal to contiguous regions of the target nucleic acid, and where an overlap forms between the upstream nucleic acid and duplex formed between the downstream nucleic acid and the target nucleic acid. An invasive cleavage structure can be formed by a single nucleic acid molecule (e.g., double hairpin), two nucleic acid molecules (e.g., 5' hairpin structure with an upstream oligonucleotide), or three nucleic acid molecules (e.g., target sequence, probe oligonucleotide, and an upstream oligonucleotide). An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain).

The term "cleavage means" or "cleavage agent" as used herein refers to any agent that is capable of cleaving a cleavage structure, including but not limited to enzymes. "Structure-specific nucleases" or "structure-specific enzymes" are enzymes that recognize specific secondary structures in a nucleic acid molecule and cleave these structures. The cleavage agents of the invention cleave a nucleic acid molecule in response to the formation of cleavage structures; it is not necessary that the cleavage agents cleave the cleavage structure at any particular location within the cleavage structure.

The cleavage agent may include nuclease activity provided from a variety of sources including the CLEAVASE enzymes (Third Wave Technologies, Madison, Wis.), the FEN-1 endonucleases (including RAD2 and XPG proteins), Taq DNA polymerase and E. coli DNA polymerase I. The cleavage means may include enzymes having 5' nuclease activity (e.g., Taq DNA polymerase (DNAP), E. coli DNA polymerase I). The cleavage means may also include modified DNA polymerases having 5' nuclease activity but lacking synthetic activity. Examples of cleavage means suitable for use in the method and kits of the present invention are provided in U.S. Pat. Nos. 5,614,402; 5,795,763; 5,843,669; 6,090,606; PCT Appln. Nos WO 98/23774; WO 02/070755A2; WO01/90337A2; and WO03/073067A2, each of which is herein incorporated by reference it its entirety.

The term "thermostable" when used in reference to an enzyme, such as a 5' nuclease, indicates that the enzyme is functional or active (i.e., can perform catalysis) at an elevated temperature, i.e., at about 55° C. or higher.

The term "cleavage products" as used herein, refers to products generated by the reaction of a cleavage means with a cleavage structure (i.e., the treatment of a cleavage structure with a cleavage agent).

The term "probe oligonucleotide," when used in reference to an invasive cleavage reaction, refers to an oligonucleotide that interacts with a target nucleic acid to form a cleavage structure in the presence or absence of an INVADER oligonucleotide. When annealed to the target nucleic acid, the probe oligonucleotide and target form a cleavage structure and cleavage occurs within the probe oligonucleotide.

The term "INVADER oligonucleotide" refers to an oligonucleotide that hybridizes to a target nucleic acid at a location near the region of hybridization between a probe and the target nucleic acid, wherein the INVADER oligonucleotide comprises a portion (e.g., a chemical moiety, or nucleotide—whether complementary to that target or not) that overlaps with the region of hybridization between the probe and target. In some embodiments, the INVADER oligonucleotide contains sequences at its 3' end that are substantially the same as sequences located at the 5' end of a probe oligonucleotide.

The term "cassette," when used in reference to an invasive cleavage reaction, as used herein refers to an oligonucleotide or combination of oligonucleotides configured to generate a detectable signal in response to cleavage of a probe oligonucleotide in an INVADER assay. In preferred embodiments, the cassette hybridizes to a non-target cleavage product from cleavage of the probe oligonucleotide to form a second invasive cleavage structure, such that the cassette can then be cleaved.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label. In particularly preferred embodiments, cassette comprises labeled moieties that produce a fluorescence resonance energy transfer (FRET) effect.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "nucleotide analog" as used herein refers to modified or non-naturally occurring nucleotides including but not limited to analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include comprise modified forms of deoxyribonucleotides as well as ribonucleotides.

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid, solid (e.g., blood sample, urine sample, semen sample, stool sample, tissue, amniotic fluid, saliva, etc) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

An oligonucleotide is said to be present in "excess" relative to another oligonucleotide (or target nucleic acid sequence) if that oligonucleotide is present at a higher molar concentration that the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present at least a 100-fold molar excess; typically at least 1 pmole of each probe oligonucleotide would be used when the target nucleic acid sequence was present at about 10 fmoles or less.

The term "nucleic acid sequence" as used herein refers to an oligonucleotide, nucleotide or polynucleotide, and fragments or portions thereof, and to DNA or RNA of genomic or synthetic origin that may be single or double stranded, and represent the sense or antisense strand. Similarly, "amino acid sequence" as used herein refers to peptide or protein sequence.

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

DESCRIPTION OF THE DRAWINGS

FIG. 4A also shows the use of both low annealing and high annealing PCR to amplify the target sequence.

FIG. 7A shows these results for detecting the wild-type allele, and FIG. 7B show these results for detecting the heterozygous allele.

FIG. 8A shows the results of detecting the heterozygous allele, and FIG. 8B shows the results of detecting the wild-type allele.

DESCRIPTION OF THE INVENTION

The present invention provides methods, compositions, and kits comprising snap-back primers used for forming 3' hairpin structures, 5' hairpin structures, and double hairpin structures. The hairpin structures may be used for detecting target sequences (e.g., such as small RNA target sequence), for detecting polymorphisms in target sequences (e.g., such as polymorphisms located near the 5' or 3' ends of the target sequence), or other nucleic acid characterization methods. In certain embodiments, the hairpin structures form invasive cleavage structures (e.g., in combination with a probe or upstream oligonucleotide) which may be cleaved by structure-specific enzymes in order to detect the presence or absence of a particular target nucleotide or nucleotide sequence.

The following sections of the Description of the Invention describe certain preferred embodiments of the present invention. The present invention is not limited to these exemplary embodiments.

Figure 1:
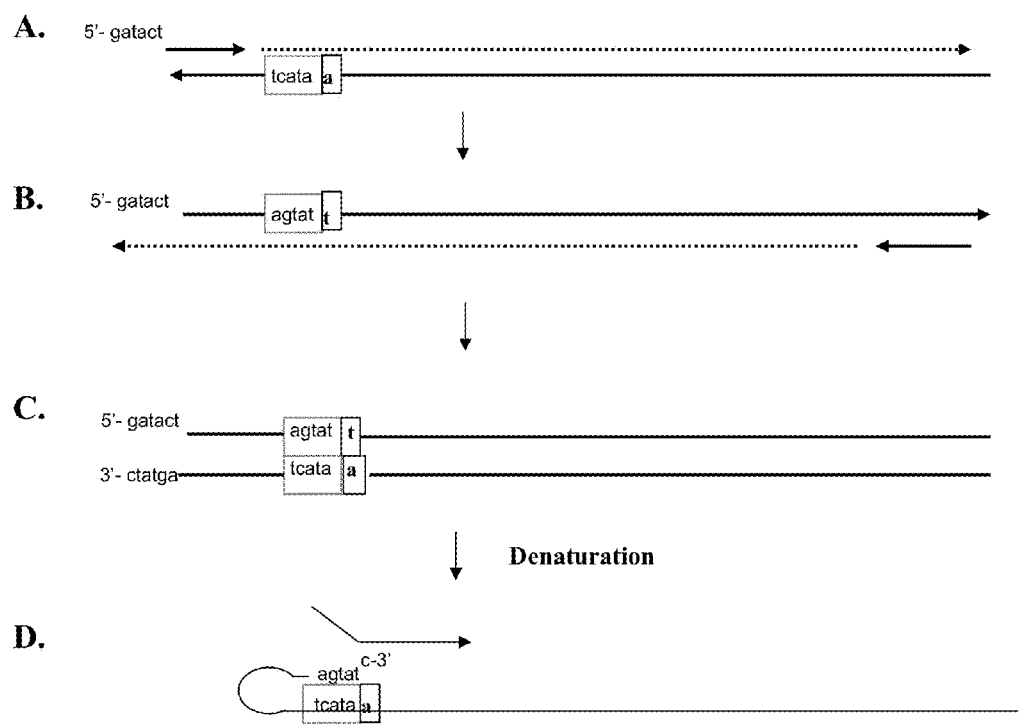
FIGS. 1A-D show an exemplary method for using a snap-back primer and a reverse primer to generate a 3' hairpin structure, which may be combined with a downstream probe to generate a cleavable invasive cleavage structure.
Figure 3:
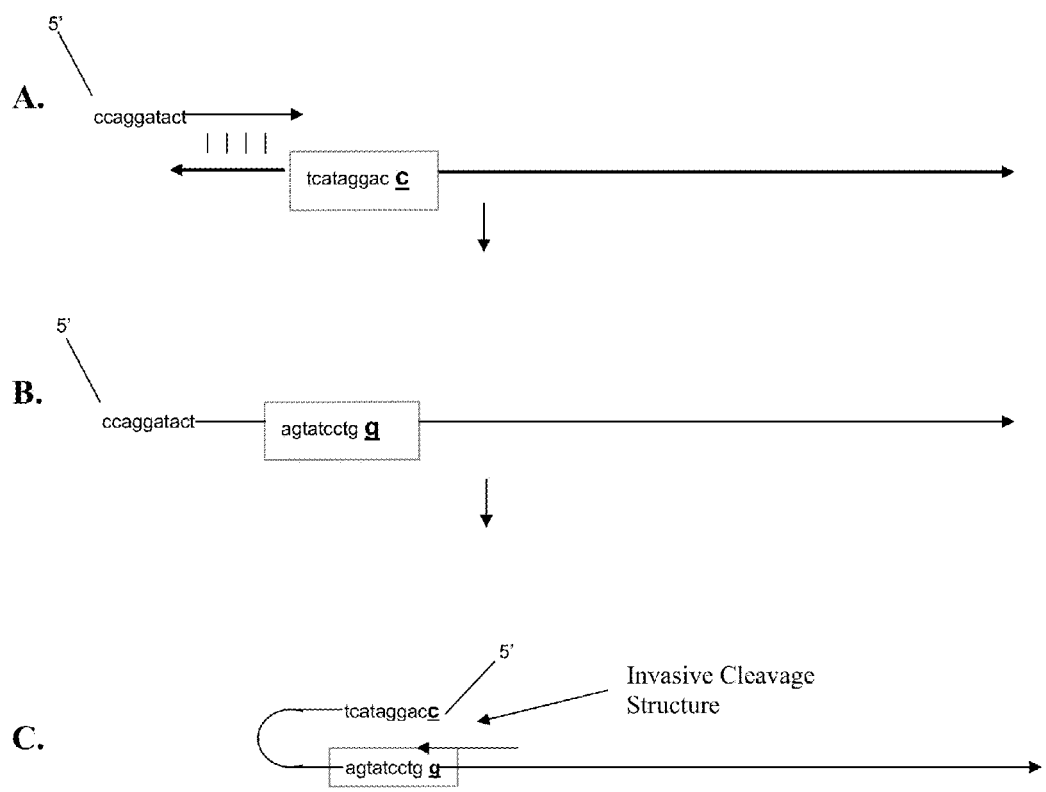
FIGS. 3A-C show an exemplary method for using a snap-back primer to generate a 5' hairpin structure, which may be combined with an upstream oligonucleotide to generate a cleavable invasive cleavage structure.

I. Snap-Back Primers for Generating Hairpin Structures and Detecting Target Sequences The snap-back primers of the present invention can be used to generate various hairpin structures. For example, certain snap-back primers, in conjunction with a reverse primer, can generate 3' hairpin structures (e.g., FIG. 1). Other snap-back primers can be use to generate 5' hairpin structures (e.g., FIG. 3). The use two snap-back primers can be used to generate double hairpin structures (e.g., FIG. 5).

FIGS. 1A-D show an exemplary method for using a snap-back primer and a reverse primer to generate a 3' hairpin structure, which may be combined with a downstream probe to generate a cleavable invasive cleavage structure. FIG. 1A shows a snap-back primer hybridized to a target nucleic acid. The snap-back primer is shown with an exemplary 3' region hybridized to the target nucleic acid and an exemplary 5' region ("gatact") that is not hybridized to the target nucleic acid. FIG. 1B shows the result of extending the snap-back primer along the target nucleic acid (e.g., with a polymerase) to generate a first amplification product. FIG. 1B also shows a reverse primer hybridized to the first amplification product. FIG. 1C shows the result of extending the reverse primer along the first amplification product in order to generate a second amplification product. FIG. 1C shows various regions of the second amplification product, including an exemplary 3' snap-back portion ("tatga"), which is complementary to a non-adjacent portion ("tcata") of the second amplification product. FIG. 1D shows the second amplification product formed into a 3' hairpin structure, with the 3' snap-back portion hybridized to the non-adjacent portion. FIG. 1D also shows a 3' terminal portion ("c") which is not hybridized to the second amplification product. FIG. 1D also shows a down stream probe, which is configured to hybridize to the 3' hairpin structure immediately upstream of the non-adjacent portion in order to form an invasive cleavage structure. FIGS. 1A-D also show a target nucleotide "A" in the target sequence, which is then replicated in the 3' hairpin structure. This target nucleotide can be detected, for example, when the downstream probe in 1D hybridizes to the 3' hairpin structure. In FIG. 1D, the 3' snap-back portion is shown hybridized to the non-adjacent portion with complete complementarity as all five bases are matched. In certain embodiments, however, there is only partial complementarity between the 3' snap-back portion and the non-adjacent portion (e.g., 1, 2, 3, or 4 of the five bases shown in FIG. 1D are mis-matched).

Figure 2:
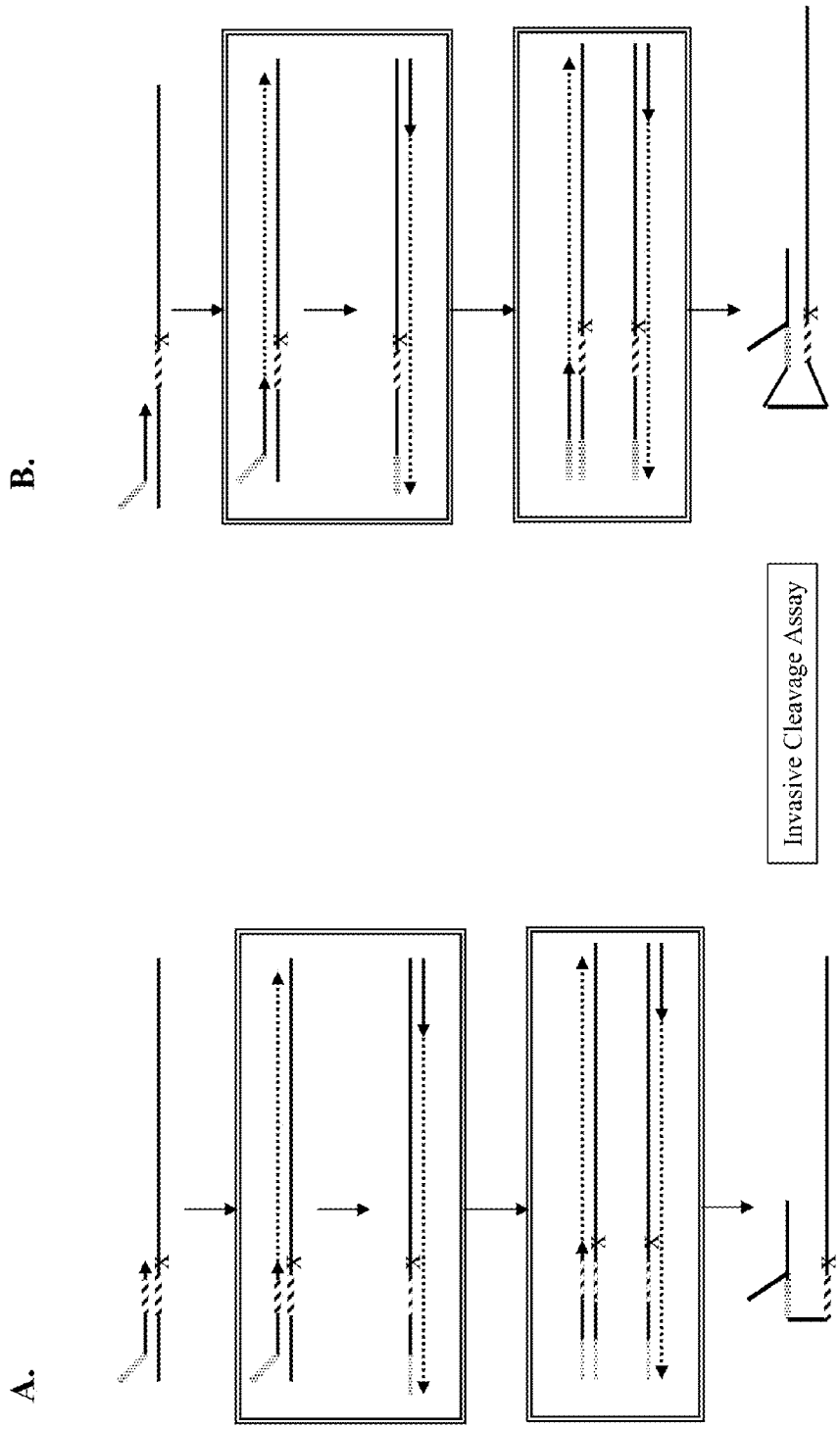
FIGS. 2A and 2B show exemplary methods for using a snap-back primer and a reverse primer to generate a 3' hairpin structure, which is combined with a downstream probe to generate a cleavable invasive cleavage structure.

FIGS. 2A and 2B show exemplary methods for using a snap-back primer and a reverse primer to amplify a target with PCR and to generate a 3' hairpin structure. As shown in these figures, the 3' hairpin structures can be combined with downstream probes to generate cleavable invasive cleavage structures. In FIG. 2A, the snap-back primer is hybridized immediately downstream of a polymorphic base ("X") to be detected. As such, the snap-back primer in FIG. 2A is able to hybridize to itself as the 5' region configured to not hybridize to the target nucleic acid is able to hybridize to a portion of the 3' region of the snap-back primer. FIG. 2A also shows the use of both low annealing and high annealing PCR to amplify the target sequence. In contrast, the snap-back primer in FIG. 2B hybridizes to the target sequence such that there is a gap between the polymorphic base to be detected ("X") and where the snap-back primer hybridizes. Thus, the snap-back primers in FIG. 2B are still able to generate a 3' hairpin structure in conjunction with a reverse primer, but primers are not lost due to internal hybridization. FIG. 2B also shows the use of both low annealing and high annealing PCR to amplify the target sequence.

FIGS. 3A-C show an exemplary method for using a snap-back primer to generate a 5' hairpin structure, which may be combined with an upstream oligonucleotide (which may be provided or generated in the sample with a polymerase and nucleotides) to generate a cleavable invasive cleavage structure. FIG. 3A shows a snap-back primer hybridized to a target nucleic acid. The snap-back primer is shown with an exemplary 3' region hybridized to the target nucleic acid and is also shown with an exemplary 5' region ("5'-ccaggatact") that is not hybridized to the target nucleic acid. FIG. 3A also shows the following sequence in the target sequence "tcataggacc," where the 3' terminal "c" (shown in bold and underline) may be a target nucleotide desired to be detected. FIG. 3B shows the result of extending the snap-back primer along the target nucleic acid (e.g., with a polymerase) to generate an amplification product. FIG. 3B shows various regions of the amplification product, including an exemplary 5' snap-back portion ("ccaggatact"), which is complementary to a non-adjacent portion ("agtatcctgg") of the amplification product. FIG. 3C shows the amplification product formed into a 5' hairpin structure, with the 5' snap-back portion hybridized to the non-adjacent portion. FIG. 3C also shows a 5' terminal portion ("5'-") which is not hybridized to the amplification product. FIG. 3C also shows an upstream oligonucleotide, which is configured to hybridize to the 5' hairpin structure immediately downstream of the non-adjacent portion (with a one base overlap) in order to form an invasive cleavage structure. The invasive cleavage structure, in certain embodiments, may be cleaved with a cleavage agent (e.g., a FEN-1 enzyme) in order to detect the formation of the 5' cleavage structure, or to specifically detect the 3' terminal base in the non-adjacent portion (i.e. the "g" at the 3' end of the non-adjacent portion). The "g" in the non-adjacent portion corresponds to the "c" shown in bold and underline above in the target sequence, such that detecting "g" in the 5' hairpin structure indicates the presence of a "c" in the target sequence at the recited position. It is noted that, had the target nucleic acid had an "a" "t" or "g"

at the bold and underlined position in the target nucleic acid (rather than a "c") the 5' hairpin structure in combination with the upstream oligonucleotide would not be cleavable by a structure specific enzyme as no "g" would be present at the corresponding position in the 5' hairpin structure. The lack of cleavage would indicate that the target nucleic acid does not contain a "c" at the bold and underlined position.

In FIG. 3C, the 5' snap-back portion is shown hybridized to the non-adjacent portion with complete complementarity as all ten bases are matched. In certain embodiments, however, there is only partial complementarity between the 5' snap-back portion and the non-adjacent portion (e.g., 1, 2, 3, 4, 5, 6, 7, 8, or 9 of the ten bases shown in FIG. 3C are mismatched).

Figure 4:
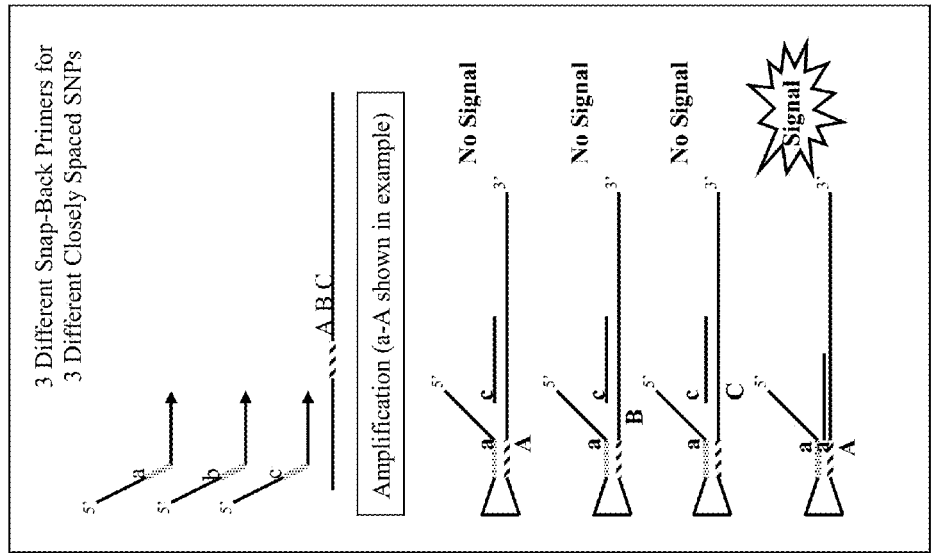
FIG. 4A shows an exemplary method for using a snap-back primer to generate a 5' hairpin structure, which may be combined with an upstream oligonucleotide to generate a cleavable invasive cleavage structure.
FIG. 4B shows the use of three different snap-back primers for detecting three closely spaced single nucleotide polymorphisms (SNPs).
Figure 4:
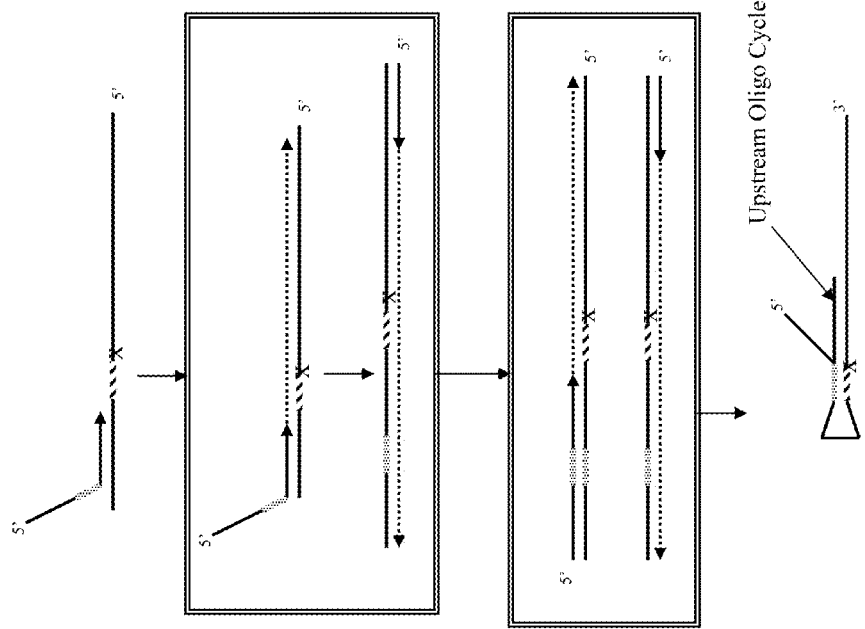

FIG. 4A shows an exemplary method for using a snap-back primer to generate a 5' hairpin structure, which may be combined with an upstream oligonucleotide to generate a cleavable invasive cleavage structure. FIG. 4A also shows the use of both low annealing and high annealing PCR to amplify the target sequence. FIG. 4B shows the use of three different snap-back primers for detecting three closely spaced single nucleotide polymorphisms (SNPs). The top panel in FIG. 4B shows the three snap-back primers, each configured for detecting a different SNP (A, B, or C) as well as the target sequences showing the three SNPS (A, B, and C) in close proximity. The bottom panel in FIG. 4B shows the detection of SNP "A," where only the combination of the proper 5' hairpin structure and proper upstream oligonucleotide (specific for SNP "A") forms an invasive cleavage structure that is cleaved to generate a detectable signal.

Figure 5:
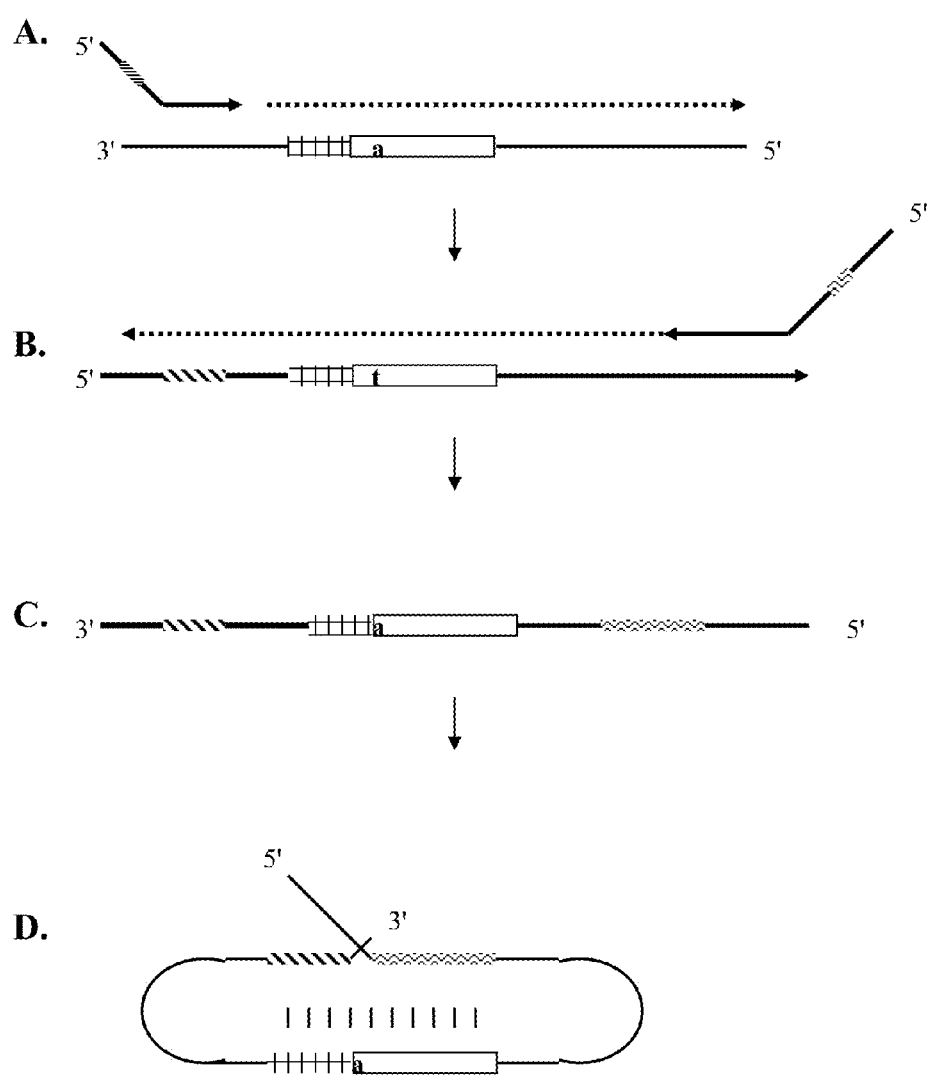
FIGS. 5 A-D show an exemplary method for using a forward snap-back primer and a reverse snap-back primer to generate a double hairpin structure which is also an invasive cleavage structure.

FIGS. 5 A-D show an exemplary method for using a forward snap-back primer and a reverse snap-back primer to generate a double hairpin structure which is also an invasive cleavage structure. It is noted that, in other embodiments, the double hairpin structure that is formed does not form an invasive cleavage structure. FIG. 5A shows a forward snap-back primer hybridized to a target nucleic acid. The forward snap-back primer is shown with an exemplary 3' region hybridized to the target nucleic acid and an exemplary 5' region that is not hybridized to the target nucleic acid. FIG. 5B shows the result of extending the forward snap-back primer along the target nucleic acid (e.g., with a polymerase) to generate a first amplification product. FIG. 5B also shows a reverse snap-back primer hybridized to the first amplification product. The reverse snap-back primer is shown with an exemplary 3' region hybridized to the first amplification product and an exemplary 5' region not hybridized to the first amplification product. FIG. 5C shows the result of extending the reverse snap-back primer along the first amplification product in order to generate a second amplification product. FIG. 5C shows various regions of the second amplification product, including an exemplary 3' snap-back portion, which is complementary to a first non-adjacent portion (shown in broad striped lines) of the second amplification product, and a 5' snap-back portion, which is complementary to a second non-adjacent portion (shown in closely spaced striped lines, immediately 5' of the first non-adjacent portion). FIG. 5D shows the second amplification product formed into a double hairpin structure, with the 3' snap-back portion hybridized to the first non-adjacent portion and the 5' snap-back portion hybridized to the second non-adjacent portion. FIG. 5D also shows a 3' terminal portion and a 5' terminal portion, both of which are not hybridized to the second amplification product such than an invasive cleavage structure is formed.

In some embodiments, the region between the snap-back portion and the non-adjacent portion contains a base or stretch of bases that would interfere with hybridization of a nucleic acid sequence (e.g., upstream oligonucleotide or downstream probe) if no hairpin were formed. Indeed, one of the advantages of the present invention is the ability to avoid certain stretches of a target nucleic acid by making them part of the "loop" of the hairpin. In this regard, assays can be designed that avoid having to use probes, primers, or invader type sequences that hybridize, or attempt to hybridize, to troublesome areas of the target that may, for example, be close to a polymorphism that is to be detected.

As detailed above, in certain embodiments, the hairpin structures of the present invention form invasive cleavage structures (e.g., that can be cleaved to detect a nucleotide corresponding to a nucleotide in a target sequence). As detailed below, in general, invasive cleavage assays are formed and cleaved at a temperature which is optimally around 63 degrees Celsius. However, the hairpin structures of the present invention allow higher temperatures to be employed as the hairpins provide the required structures and are more stable at higher temperatures. As a result, higher specificity can be achieved when the hairpin containing invasive cleavage structures of the present invention are cleaved with a cleavage agent. In certain embodiments, the hairpin containing invasive cleavage structures are formed (and cleaved) at about 70 degrees Celsius . . . 80 degrees Celsius . . . 90 degrees Celsius . . . 95 degrees Celsius or higher.

The snap-back primers may be used to determine if a certain target nucleic is present or absent in a sample. For example, if no hairpin structure is formed (e.g., 3' or 5' or double hairpin structure) the target sequence is not present, or not present at detectable levels, in the sample. The present invention is not limited to detection methods used to determine if a hairpin structure has been formed or not. Methods for detecting the formation of such hairpin structures are described below. In other embodiments, the snap-back primers are used to determine the identity (or the presence or absence) of a particular nucleotide in a target sequence (e.g., a nucleotide at a polymorphic position that may be associated with a disease condition). For example, any type of suitable detection method may be employed to detect a nucleotide in the 3' or 5' or double hairpin structure that corresponds to the nucleotide in the target sequence. Exemplary detection methods are described below. In certain embodiments, the hairpin structures form invasive cleavage structures, or are combined with probe and/or upstream oligonucleotides such that invasive cleavage structures are formed, such that the identity of the nucleotide of interest in the hairpin structure can be detected.

II. Detection Assays

The present invention is not limited to a particular detection assay for detecting the formation of hairpin structures (e.g., 3' or 5' or double hairpin structures) or for detecting a nucleotide in a hairpin structure corresponding to a nucleotide of interest in a target sequence. Exemplary assays that find use with the methods of the present invention are described below.

A. INVADER Assays

In certain embodiments, an INVADER assay is employed to detect the formation of a hairpin structure or detect the identity of a nucleotide in a hairpin structure corresponding to a nucleotide of interest in an original target sequence. Various aspects of the INVADER assay are described below. It should be understood that, in this discussion, the "upstream/INVADER" oligonucleotide, or the "downstream probe" or both, may be provided by the hairpin structures of the present invention (i.e., not as separate oligonucleotides as they are generally discussed below). For example, a 3' hairpin structure (see, e.g., FIG. 1) may provide the upstream/INVADER oligonucleotide and "target," such that all that is needed to form an invasive cleavage structure is the addition of a probe oligonucleotide. Also for example, a 5' hairpin structure (see, FIG. 3) may provide the downstream probe and "target," such that all that is needed to form an invasive cleavage structure is the addition of an upstream oligonucleotide. Likewise, for double hairpin structures (see, e.g., FIG. 5), no additional oligonucleotides need to be added if the double hairpin structure forms an overlap.

The INVADER assay provides means for forming a nucleic acid cleavage structure that is dependent upon the presence of a target nucleic acid and cleaving the nucleic acid cleavage structure so as to release distinctive cleavage products. 5' nuclease activity, for example, is used to cleave the target-dependent cleavage structure and the resulting cleavage products are indicative of the presence of specific target nucleic acid sequences in the sample. When two strands of nucleic acid, or oligonucleotides, both hybridize to a target nucleic acid strand such that they form an overlapping invasive cleavage structure, as described below, invasive cleavage can occur. Through the interaction of a cleavage agent (e.g., a 5' nuclease) and the upstream oligonucleotide, the cleavage agent can be made to cleave the downstream oligonucleotide at an internal site in such a way that a distinctive fragment is produced. Such embodiments have been termed the INVADER assay (Third Wave Technologies, Madison, Wis.) and are described in U.S. Pat. Nos. 5,846,717, 5,985,557, 5,994,069, 6,001,567, and 6,090,543, WO 97/27214, WO 98/42873, Lyamichev et al., Nat. Biotech., 17:292 (1999), Hall et al., PNAS, USA, 97:8272 (2000), each of which is herein incorporated by reference in their entirety for all purposes.

The INVADER assay detects hybridization of probes to a target by enzymatic cleavage of specific structures by structure specific enzymes. INVADER type assays are described in U.S. Pat. Nos. 5,846,717; 6,090,543; 6,001,567; 5,985, 557; 6,090,543; 5,994,069; Lyamichev et al., Nat. Biotech., 17:292 (1999), Hall et al., PNAS, USA, 97:8272 (2000), WO97/27214 and WO98/42873, each of which is herein incorporated by reference in their entirety for all purposes).

The INVADER assay detects specific DNA and RNA sequences by using structure-specific enzymes (e.g. FEN endonucleases) to cleave a complex formed by the hybridization of overlapping oligonucleotide probes. In certain embodiments, elevated temperature and an excess of one of the probes enable multiple probes to be cleaved for each target sequence present without temperature cycling. In some embodiments, these cleaved probes then direct cleavage of a second labeled probe. The secondary probe oligonucleotide can be 5'-end labeled with fluorescent that is quenched by an internal dye. Upon cleavage, the de-quenched fluorescent labeled product may be detected using a standard fluorescence plate reader.

The INVADER assay detects specific target sequences in unamplified, as well as amplified, RNA and DNA including genomic DNA. In the embodiments, the INVADER assay uses two cascading steps (a primary and a secondary reaction) both to generate and then to amplify the target-specific signal. For convenience, the alleles in the following discussion are described as wild-type (WT) and mutant (MT), even though this terminology does not apply to all genetic variations or target sequences. In the primary reaction, the WT primary probe and the INVADER oligonucleotide hybridize in tandem to the target nucleic acid to form an overlapping structure. An unpaired "flap" is included on the 5' end of the WT primary probe. A structure-specific enzyme (e.g. the CLEAVASE enzyme, Third Wave Technologies) recognizes the overlap and cleaves off the unpaired flap, releasing it as a target-specific product. In the secondary reaction, this cleaved product serves as an INVADER oligonucleotide on the WT fluorescence resonance energy transfer (WT-FRET) probe to again create the structure recognized by the structure specific enzyme. When the two dyes on a single FRET probe are separated by cleavage, a detectable fluorescent signal above background fluorescence is produced. Consequently, cleavage of this second structure results in an increase in fluorescence, indicating the presence of the WT allele (or mutant allele if the assay is configured for the mutant allele to generate the detectable signal). In some embodiments, FRET probes having different labels (e.g. resolvable by difference in emission or excitation wavelengths, or resolvable by time-resolved fluorescence detection) are provided for each allele or locus to be detected, such that the different alleles or loci can be detected in a single reaction. In such embodiments, the primary probe sets and the different FRET probes may be combined in a single assay, allowing comparison of the signals from each allele or locus in the same sample.

If the primary probe oligonucleotide and the target nucleotide sequence do not match perfectly at the cleavage site, the overlapped structure does not form and cleavage is suppressed. The structure specific enzyme (e.g., CLEAVASE VIII enzyme, Third Wave Technologies) used cleaves the overlapped structure more efficiently (e.g. at least 340-fold) than the non-overlapping structure, allowing excellent discrimination of the alleles.

The probes turn over without temperature cycling to produce many signals per target (i.e., linear signal amplification). Similarly, each target-specific product can enable the cleavage of many FRET probes.

The primary INVADER assay reaction is directed against the target DNA or RNA being detected. The target DNA is the limiting component in the first invasive cleavage, since the INVADER and primary probe are supplied in molar excess. In the second invasive cleavage, it is the released flap that is limiting. When these two cleavage reactions are performed sequentially, the fluorescence signal from the composite reaction accumulates linearly with respect to the target DNA amount.

In certain embodiments, the INVADER assay, or other nucleotide detection assays, are performed with accessible site designed oligonucleotides and/or bridging oligonucleotides. Such methods, procedures and compositions are described in U.S. Pat. No. 6,194,149, WO9850403, and WO0198537, all of which are specifically incorporated by reference in their entireties.

In certain embodiments, the target nucleic acid sequence is amplified prior to detection (e.g. such that synthetic nucleic acid is generated). In some embodiments, the target nucleic acid comprises genomic DNA. In other embodiments, the target nucleic acid comprises synthetic DNA or RNA. In some embodiments, synthetic DNA within a sample is created using a purified polymerase. In some embodiments, creation of synthetic DNA using a purified polymerase comprises the use of PCR. In other embodiments, creation of synthetic DNA using a purified DNA polymerase, suitable for use with the methods of the present invention, comprises use of rolling circle amplification, (e.g., as in U.S. Pat. Nos. 6,210,884, 6,183,960 and 6,235,502, herein incorporated by reference in their entireties). In other embodiments, creation of synthetic DNA comprises copying genomic DNA by priming from a plurality of sites on a genomic DNA sample. In some embodiments, priming from a plurality of sites on a genomic DNA sample comprises using short (e.g., fewer than about 8 nucleotides, such as 7 or 6 nucleotides) oligonucleotide primers. In other embodiments, priming from a plurality of sites on a genomic DNA comprises extension of 3' ends in nicked, double-stranded genomic DNA (i.e., where a 3' hydroxyl group has been made available for extension by breakage or cleavage of one strand of a double stranded region of DNA). Some examples of making synthetic DNA using a purified polymerase on nicked genomic DNAs, suitable for use with the methods and compositions of the present invention, are provided in U.S. Pat. No. 6,117,634, issued Sep. 12, 2000, and U.S. Pat. No. 6,197,557, issued Mar. 6, 2001, and in PCT application WO 98/39485, each incorporated by reference herein in their entireties for all purposes.

In some embodiments, synthetic DNA suitable for use with the methods and compositions of the present invention is made using a purified polymerase on multiply-primed genomic or other DNA, as provided, e.g., in U.S. Pat. Nos. 6,291,187, and 6,323,009, and in PCT applications WO 01/88190 and WO 02/00934, each herein incorporated by reference in their entireties for all purposes. In these embodiments, amplification of DNA such as genomic DNA is accomplished using a DNA polymerase, such as the highly processive Φ 29 polymerase (as described, e.g., in U.S. Pat. Nos. 5,198,543 and 5,001,050, each herein incorporated by reference in their entireties for all purposes) in combination with exonuclease-resistant random primers, such as hexamers. In certain embodiments, LAMP amplification, LOOP amplification (e.g., U.S. Pat. No. 6,410,278 herein incorporated by reference), helicase-dependent amplification (e.g., from NEB or BIOHELIX), NASBA, MDA, TMA, or whole genome amplification (e.g., from Rubicon Genomics) are employed for generating synthetic DNA.

Oligonucleotide Design for the INVADER Assay

In some embodiments where an oligonucleotide is designed for use in the INVADER assay to detect a target nucleic acid the sequence(s) of interest are entered into the INVADERCREATOR program (Third Wave Technologies, Madison, Wis.). This same type of software program finds use to design snap-back primer capable of generating the hairpin structures of the present invention.

Sequences may be input for analysis from any number of sources, either directly into the computer hosting the INVADERCREATOR program, or via a remote computer linked through a communication network (e.g., a LAN, Intranet or Internet network). The program designs probes for both the sense and antisense strand. Strand selection is generally based upon the ease of synthesis, minimization of secondary structure formation, and manufacturability. In some embodiments, the user chooses the strand for sequences to be designed for. In other embodiments, the software automatically selects the strand. By incorporating thermodynamic parameters for optimum probe cycling and signal generation (Allawi and SantaLucia, Biochemistry, 36:10581 [1997]), oligonucleotide probes may be designed to operate at a pre-selected assay temperature (e.g., 63° C.). Based on these criteria, a final probe set (e.g., match and mismatch probes and an INVADER oligonucleotide) is selected.

In some embodiments, the INVADERCREATOR system is a web-based program with secure site access that contains a link to BLAST (available at the National Center for Biotechnology Information, National Library of Medicine, National Institutes of Health website) and that can be linked to RNAstructure (Mathews et al., RNA 5:1458 [1999]), a software program that incorporates mfold (Zuker, Science, 244:48 [1989]). RNAstructure tests the proposed oligonucleotide designs generated by INVADERCREATOR for potential uni- and bimolecular complex formation. INVADERCREATOR is open database connectivity (ODBC)-compliant and uses the Oracle database for export/integration. The INVADERCREATOR system was configured with Oracle to work well with UNIX systems, as most genome centers are UNIX-based.

In some embodiments, the INVADERCREATOR analysis is provided on a separate server (e.g., a Sun server) so it can handle analysis of large batch jobs. For example, a customer can submit up to 2,000 SNP sequences in one email. The server passes the batch of sequences on to the INVADERCREATOR software, and, when initiated, the program designs detection assay oligonucleotide sets. In some embodiments, probe set designs are returned to the user within 24 hours of receipt of the sequences.

Each INVADER reaction includes at least two target sequence-specific, unlabeled oligonucleotides for the primary reaction: an upstream INVADER oligonucleotide and a downstream Probe oligonucleotide. The INVADER oligonucleotide is generally designed to bind stably at the reaction temperature, while the probe is designed to freely associate and disassociate with the target strand, with cleavage occurring only when an uncut probe hybridizes adjacent to an overlapping INVADER oligonucleotide. In some embodiments, the probe includes a 5' flap or "arm" that is not complementary to the target, and this flap is released from the probe when cleavage occurs. In some embodiments, the released flap participates as an INVADER oligonucleotide in a secondary reaction.

The following discussion provides one example of how a user interface for an INVADERCREATOR program may be configured.

The user opens a work screen, e.g., by clicking on an icon on a desktop display of a computer (e.g., a Windows desktop). The user enters information related to the target sequence for which an assay is to be designed. In some embodiments, the user enters a target sequence. In other embodiments, the user enters a code or number that causes retrieval of a sequence from a database. In still other embodiments, additional information may be provided, such as the user's name, an identifying number associated with a target sequence, and/or an order number. In preferred embodiments, the user indicates (e.g. via a check box or drop down menu) that the target nucleic acid is DNA or RNA. In other preferred embodiments, the user indicates the species from which the nucleic acid is derived. In particularly preferred embodiments, the user indicates whether the design is for monoplex (i.e., one target sequence or allele per reaction) or multiplex (i.e., multiple target sequences or alleles per reaction) detection. When the requisite choices and entries are complete, the user starts the analysis process. In one embodiment, the user clicks a "G0 Design It" button to continue.

In some embodiments, the software validates the field entries before proceeding. In some embodiments, the software verifies that any required fields are completed with the appropriate type of information. In other embodiments, the software verifies that the input sequence meets selected requirements (e.g., minimum or maximum length, DNA or RNA content). If entries in any field are not found to be valid, an error message or dialog box may appear. In preferred embodiments, the error message indicates which field is incomplete and/or incorrect. Once a sequence entry is verified, the software proceeds with the assay design.

In some embodiments, the information supplied in the order entry fields specifies what type of design will be created. In preferred embodiments, the target sequence and multiplex check box specify which type of design to create. Design options include but are not limited to SNP assay, Multiplexed SNP assay (e.g., wherein probe sets for different alleles are to be combined in a single reaction), Multiple SNP assay (e.g., wherein an input sequence has multiple sites of variation for which probe sets are to be designed), and Multiple Probe Arm assays.

In some embodiments, the INVADERCREATOR software is started via a Web Order Entry (WebOE) process (i.e., through an Intra/Internet browser interface) and these parameters are transferred from the WebOE via applet <param> tags, rather than entered through menus or check boxes.

In the case of Multiple SNP Designs, the user chooses two or more designs to work with. In some embodiments, this selection opens a new screen view (e.g., a Multiple SNP Design Selection view). In some embodiments, the software creates designs for each locus in the target sequence, scoring each, and presents them to the user in this screen view. The user can then choose any two designs to work with. In some embodiments, the user chooses a first and second design (e.g., via a menu or buttons) and clicks a "G0 Design It" button to continue.

To select a probe sequence that will perform optimally at a pre-selected reaction temperature, the melting temperature ($T_m$) of the SNP to be detected is calculated using the nearest-neighbor model and published parameters for DNA duplex formation (Allawi and SantaLucia, Biochemistry, 36:10581 [1997]). In embodiments wherein the target strand is RNA, parameters appropriate for RNA/DNA heteroduplex formation may be used. Because the assay's salt concentrations are often different than the solution conditions in which the nearest-neighbor parameters were obtained (1M NaCl and no divalent metals), and because the presence and concentration of the enzyme influence optimal reaction temperature, an adjustment should be made to the calculated $T_m$ to determine the optimal temperature at which to perform a reaction. One way of compensating for these factors is to vary the value provided for the salt concentration within the melting temperature calculations. This adjustment is termed a 'salt correction'. As used herein, the term "salt correction" refers to a variation made in the value provided for a salt concentration for the purpose of reflecting the effect on a $T_m$ calculation for a nucleic acid duplex of a non-salt parameter or condition affecting said duplex. Variation of the values provided for the strand concentrations will also affect the outcome of these calculations. By using a value of 0.5 M NaCl (SantaLucia, Proc Natl Acad Sci USA, 95:1460 [1998]) and strand concentrations of about 1 mM of the probe and 1 fM target, the algorithm for used for calculating probe-target melting temperature has been adapted for use in predicting optimal INVADER assay reaction temperature. For a set of 30 probes, the average deviation between optimal assay temperatures calculated by this method and those experimentally determined is about 1.5° C.

The length of the downstream probe to a given target sequence is defined by the temperature selected for running the reaction (e.g., 63° C.). Starting from the position of the variant nucleotide on the target DNA (the target base that is paired to the probe nucleotide 5' of the intended cleavage site), and adding on the 3' end, an iterative procedure is used by which the length of the target-binding region of the probe is increased by one base pair at a time until a calculated optimal reaction temperature ($T_m$ plus salt correction to compensate for enzyme effect) matching the desired reaction temperature is reached. The non-complementary arm of the probe is preferably selected to allow the secondary reaction to cycle at the same reaction temperature. The entire probe oligonucleotide is screened using programs such as mfold (Zuker, Science, 244: 48 [1989]) or Oligo 5.0 (Rychlik and Rhoads, Nucleic Acids Res, 17: 8543 [1989]) for the possible formation of dimer complexes or secondary structures that could interfere with the reaction. The same principles are also followed for INVADER oligonucleotide design. Briefly, starting from the position N on the target DNA, the 3' end of the INVADER oligonucleotide is designed to have a nucleotide not complementary to either allele suspected of being contained in the sample to be tested. The mismatch does not adversely affect cleavage (Lyamichev et al., Nature Biotechnology, 17: 292 [1999]), and it can enhance probe cycling, presumably by minimizing coaxial stabilization effects between the two probes. Additional residues complementary to the target DNA starting from residue N-1 are then added in the 5' direction until the stability of the INVADER oligonucleotide-target hybrid exceeds that of the probe (and therefore the planned assay reaction temperature), generally by 15-20° C.

It is one aspect of the assay design that the all of the probe sequences may be selected to allow the primary and secondary reactions to occur at the same optimal temperature, so that the reaction steps can run simultaneously. In an alternative embodiment, the probes may be designed to operate at different optimal temperatures, so that the reaction steps are not simultaneously at their temperature optima.

In some embodiments, the software provides the user an opportunity to change various aspects of the design including but not limited to: probe, target and INVADER oligonucleotide temperature optima and concentrations; blocking groups; probe arms; dyes, capping groups and other adducts; individual bases of the probes and targets (e.g., adding or deleting bases from the end of targets and/or probes, or changing internal bases in the INVADER and/or probe and/or target oligonucleotides). In some embodiments, changes are made by selection from a menu. In other embodiments, changes are entered into text or dialog boxes. In preferred embodiments, this option opens a new screen (e.g., a Designer Worksheet view).

In some embodiments, the software provides a scoring system to indicate the quality (e.g., the likelihood of performance) of the assay designs. In one embodiment, the scoring system includes a starting score of points (e.g., 100 points) wherein the starting score is indicative of an ideal design, and wherein design features known or suspected to have an adverse affect on assay performance are assigned penalty values. Penalty values may vary depending on assay parameters other than the sequences, including but not limited to the type of assay for which the design is intended (e.g., monoplex, multiplex) and the temperature at which the assay reaction will be performed. The following example provides an illustrative scoring criteria for use with some embodiments of the INVADER assay based on an intelligence defined by experimentation. Examples of design features that may incur score penalties include but are not limited to the following [penalty values are indicated in brackets, first number is for lower temperature assays (e.g., 62-64° C.), second is for higher temperature assays (e.g., 65-66° C.)]:

1. [100:100] 3' end of INVADER oligonucleotide resembles the probe arm:

| ARM SEQUENCE: | PENALTY AWARDED IF INVADER ENDS IN: |
|---|---|
| Arm 1 (SEQ ID NO: 36): CGCGCCGAGG | 5' . . . GAGGX or 5' . . . GAGGXX |

-continued

| ARM SEQUENCE: | PENALTY AWARDED IF INVADER ENDS IN: | |
|---|---|---|
| Arm 2 (SEQ ID NO: 37): ATGACGTGGCAGAC | 5' ... CAGACX or | 5' ... CAGACXX |
| Arm 3 (SEQ ID NO: 38): ACGGACGCGGAG | 5' ... GGAGX or | 5' ... GGAGXX |
| Arm 4 (SEQ ID NO: 39): TCCGCGCGTCC | 5' ... GTCCX or | 5' ... GTCCXX |

2. [70:70] a probe has 5-base stretch (i.e., 5 of the same base in a row) containing the polymorphism;
3. [60:60] a probe has 5-base stretch adjacent to the polymorphism;
4. [50:50] a probe has 5-base stretch one base from the polymorphism;
5. [40:40] a probe has 5-base stretch two bases from the polymorphism;
6. [50:50] probe 5-base stretch is of Gs—additional penalty;
7. [100:100] a probe has 6-base stretch anywhere;
8. [90:90] a two or three base sequence repeats at least four times;
9. [100:100] a degenerate base occurs in a probe;
10. [60:90] probe hybridizing region is short (13 bases or less for designs 65-67° C.; 12 bases or less for designs 62-64° C.)
11. [40:90] probe hybridizing region is long (29 bases or more for designs 65-67° C., 28 bases or more for designs 62-64° C., longer sequences for higher temperatures, although intramolecular interactions may be considered)
12. [5:5] probe hybridizing region length—per base additional penalty
13. [80:80] Ins/Del design with poor discrimination in first 3 bases after probe arm
14. [100:100] calculated INVADER oligonucleotide Tm within 7.5° C. of probe target Tm (designs 65-67° C. with INVADER oligonucleotide less than ≤70.5° C., designs 62-64° C. with INVADER oligonucleotide ≤69.5° C.
15. [20:20] calculated probes Tms differ by more than 2.0° C.
16. [100:100] a probe has calculated Tm 2° C. less than its target Tm
17. [10:10] target of one strand 8 bases longer than that of other strand
18. [30:30] INVADER oligonucleotide has 6-base stretch anywhere—initial penalty
19. [70:70] INVADER oligonucleotide 6-base stretch is of Gs—additional penalty
20. [15:15] probe hybridizing region is 14, 15 or 24-28 bases long (65-67° C.) or 13,14 or 26,27 bases long (62-64° C.), or longer for higher temperatures, although intramolecular interactions may be considered
21. [15:15] a probe has a 4-base stretch of Gs containing the polymorphism In particularly preferred embodiments, temperatures for each of the oligonucleotides in the designs are recomputed and scores are recomputed as changes are made. In some embodiments, score descriptions can be seen by clicking a "descriptions" button. In some embodiments, a BLAST search option is provided. In preferred embodiments, a BLAST search is done by clicking a "BLAST Design" button. In some embodiments, this action brings up a dialog box describing the BLAST process. In preferred embodiments, the BLAST search results are displayed as a highlighted design on a Designer Worksheet.

In some embodiments, a user accepts a design by clicking an "Accept" button. In other embodiments, the program approves a design without user intervention. In preferred embodiments, the program sends the approved design to a next process step (e.g., into production; into a file or database). In some embodiments, the program provides a screen view (e.g., an Output Page), allowing review of the final designs created and allowing notes to be attached to the design. In preferred embodiments, the user can return to the Designer Worksheet (e.g., by clicking a "G0 Back" button) or can save the design (e.g., by clicking a "Save It" button) and continue (e.g., to submit the designed oligonucleotides for production).

In some embodiments, the program provides an option to create a screen view of a design optimized for printing (e.g., a text-only view) or other export (e.g., an Output view). In preferred embodiments, the Output view provides a description of the design particularly suitable for printing, or for exporting into another application (e.g., by copying and pasting into another application). In particularly preferred embodiments, the Output view opens in a separate window.

The present invention is not limited to the use of the INVADERCREATOR software. Indeed, a variety of software programs are contemplated and are commercially available, including, but not limited to GCG Wisconsin Package (Genetics computer Group, Madison, Wis.) and Vector NTI (Informax, Rockville, Md.). Other detection assays may be used in the present invention.

Multiplex Reactions

Since its introduction in 1988 (Chamberlain, et al. Nucleic Acids Res., 16:11141 (1988)), multiplex PCR has become a routine means of amplifying multiple genetic loci in a single reaction. This approach has found utility in a number of research, as well as clinical, applications. Multiplex PCR has been described for use in diagnostic virology (Elnifro, et al. Clinical Microbiology Reviews, 13: 559 (2000)), paternity testing (Hidding and Schmitt, Forensic Sci. Int., 113: 47 (2000); Bauer et al., Int. J. Legal Med. 116: 39 (2002)), preimplantation genetic diagnosis (Ouhibi, et al., Curr Womens Health Rep. 1: 138 (2001)), microbial analysis in environmental and food samples (Rudi et al., Int J Food Microbiology, 78: 171 (2002)), and veterinary medicine (Zarlenga and Higgins, Vet Parasitol. 101: 215 (2001)), among others. Most recently, expansion of genetic analysis to whole genome levels, particularly for single nucleotide polymorphisms, or SNPs, has created a need for highly multiplexed PCR capabilities. Comparative genome-wide association and candidate gene studies require the ability to genotype between 100,000-500,000 SNPs per individual (Kwok, Molecular Medicine Today, 5: 538-5435 (1999); Kwok, Pharmacogenomics, 1: 231 (2000); Risch and Merikangas, Science, 273: 1516 (1996)). Moreover, SNPs in coding or regulatory regions alter gene function in important ways (Cargill et al. Nature Genetics, 22: 231 (1999); Halushka et al., Nature Genetics, 22: 239 (1999)), making these SNPs useful diagnostic tools in personalized medicine (Hagmann, Science, 285: 21 (1999); Cargill et al. Nature Genetics, 22: 231 (1999); Halushka et al., Nature Genetics, 22: 239 (1999)). Likewise, validating the medical association of a set of SNPs previously identified for their potential clinical relevance as part of a diagnostic panel will mean testing thousands of individuals for thousands of markers at a time.

Despite its broad appeal and utility, several factors complicate multiplex PCR amplification. Chief among these is the phenomenon of PCR or amplification bias, in which certain loci are amplified to a greater extent than others. Two classes of amplification bias have been described. One, referred to as PCR drift, is ascribed to stochastic variation in such steps as primer annealing during the early stages of the reaction (Polz and Cavanaugh, Applied and Environmental Microbiology, 64: 3724 (1998)), is not reproducible, and may be more prevalent when very small amounts of target molecules are being amplified (Walsh et al., PCR Methods and Applications, 1: 241 (1992)). The other, referred to as PCR selection, pertains to the preferential amplification of some loci based on primer characteristics, amplicon length, G-C content, and other properties of the genome (Polz, supra).

Another factor affecting the extent to which PCR reactions can be multiplexed is the inherent tendency of PCR reactions to reach a plateau phase. The plateau phase is seen in later PCR cycles and reflects the observation that amplicon generation moves from exponential to pseudo-linear accumulation and then eventually stops increasing. This effect appears to be due to non-specific interactions between the DNA polymerase and the double stranded products themselves. The molar ratio of product to enzyme in the plateau phase is typically consistent for several DNA polymerases, even when different amounts of enzyme are included in the reaction, and is approximately 30:1 product:enzyme. This effect thus limits the total amount of double-stranded product that can be generated in a PCR reaction such that the number of different loci amplified must be balanced against the total amount of each amplicon desired for subsequent analysis, e.g. by gel electrophoresis, primer extension, etc.

Because of these and other considerations, although multiplexed PCR including 50 loci has been reported (Lindblad-Toh et al., Nature Genet. 4: 381 (2000)), multiplexing is typically limited to fewer than ten distinct products. However, given the need to analyze as many as 100,000 to 450,000 SNPs from a single genomic DNA sample there is a clear need for a means of expanding the multiplexing capabilities of PCR reactions.

The present invention provides methods for substantial multiplexing of PCR reactions by, for example, combining the INVADER assay with multiplex PCR amplification. The INVADER assay provides a detection step and signal amplification that allows very large numbers of targets to be detected in a multiplex reaction. As desired, hundreds to thousands to hundreds of thousands of targets may be detected in a multiplex reaction.

Direct genotyping by the INVADER assay typically uses from 5 to 100 ng of human genomic DNA per SNP, depending on detection platform. For a small number of assays, the reactions can be performed directly with genomic DNA without target pre-amplification, however, for highly multiplex reactions, the amount of sample DNA may become a limiting factor.

Because the INVADER assay provides from $10^6$ to $10^7$ fold amplification of signal, multiplexed PCR in combination with the INVADER assay would use only limited target amplification as compared to a typical PCR. Consequently, low target amplification level alleviates interference between individual reactions in the mixture and reduces the inhibition of PCR by it's the accumulation of its products, thus providing for more extensive multiplexing. Additionally, it is contemplated that low amplification levels decrease a probability of target cross-contamination and decrease the number of PCR-induced mutations.

Uneven amplification of different loci presents one of the biggest challenges in the development of multiplexed PCR. Differences in amplification factors between two loci may result in a situation where the signal generated by an INVADER reaction with a slow-amplifying locus is below the limit of detection of the assay, while the signal from a fast-amplifying locus is beyond the saturation level of the assay. This problem can be addressed in several ways. In some embodiments, the INVADER reactions can be read at different time points, e.g., in real-time, thus significantly extending the dynamic range of the detection. In other embodiments, multiplex PCR can be performed under conditions that allow different loci to reach more similar levels of amplification. For example, primer concentrations can be limited, thereby allowing each locus to reach a more uniform level of amplification. In yet other embodiments, concentrations of PCR primers can be adjusted to balance amplification factors of different loci.

The present invention provides for the design and characteristics of highly multiplex PCR including hundreds to thousands of products in a single reaction. For example, the target pre-amplification provided by hundred-plex PCR reduces the amount of human genomic DNA required for INVADER-based SNP genotyping to less than 0.1 ng per assay. The specifics of highly multiplex PCR optimization and a computer program for the primer design are described in U.S. patent application Ser. Nos. 10/967,711 and 10/321,039 herein incorporated by reference in their entireties.

In addition to providing methods for highly multiplex PCR, the present invention further provides methods of conducting reverse transcription and target and signal amplification reactions in a single reaction vessel with no subsequent manipulations or reagent additions beyond initial reaction set-up. Such combined reactions are suitable for quantitative analysis of limiting target quantities in very short reaction times. Methods for conducting such reactions are described in U.S. patent application Ser. No. 11/266,723, herein incorporated by reference in its entirety.

B. Other Detection Assays

A variety of additional detection assays using a variety of technologies for hybridization and detection are available that can be used to detect the successful formation of a 3' or 5' or double hairpin structure, or a particular nucleotide in a hairpin structure corresponding to a target nucleotide in a target nucleic acid. In some embodiments, direct detection of the hairpin structures is performed with a probe. In certain embodiments, a stacker oligonucleotide is employed (e.g., that allows other sequences, such as upstream oligonucleotides or downstream probes to hybridize more efficiently). In certain embodiments, ligation assays are employed that add additional sequence to the 3' or 5' ends of the hairpin structures, wherein this added sequence is then detected by any suitable method (e.g., PCR, probe hybridization, etc.). In some embodiments, hybridization of a bound probe to a hairpin structure is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of DNA polymerases such as AMPLITAQ DNA polymerase. Generally, a probe, specific for a given allele or mutation, is included in the PCR reaction. This type of "probe" can be provided, for example, by the 5' hairpin structures of the present invention. Generally, the probe is an oligonucleotide with a 5'-reporter dye (e.g., a fluorescent dye) and a 3'-quencher dye. During PCR, if the probe is bound to its target, the 5'-3' nucleolytic activity of the AMPLITAQ polymerase cleaves the probe between the reporter and the quencher dye. The separation of the reporter dye from the quencher dye results in an increase of fluorescence. The signal accumulates with each cycle of PCR and can be monitored with a fluorimeter.

C. Formats for Assays on a Solid Support

In some embodiments, the hairpin structures are generated on, or attached to, a solid support, or the hairpin structures (or target bases therein) are detected on a solid support. The below discussion describes detection assays on a solid support in the context of the INVADER assay. However, one skilled in the relevant arts recognizes that the methods described herein can be adapted for use with any nucleic acid detection assay (e.g., the detection assays described herein).

The present invention is not limited to a particular configuration of the INVADER assay for detecting hairpin structures or bases therein. Any number of suitable configurations of the component oligonucleotides may be utilized. For example, in some embodiments of the present invention, the probe oligonucleotide is bound to a solid support and the 3' hairpin (or double hairpin) structure are provided in solution. In other embodiments of the present invention, the upstream (e.g., INVADER) oligonucleotide is bound to the support and the 5' hairpin (or double hairpin) structure is in solution. In yet other embodiments, the hairpin structures of the present invention are bound to a solid support. In further embodiments, the target nucleic acid is bound directly or indirectly to a solid support, and either or both of the probe and INVADER oligonucleotides are provided either in solution, or bound to a support. In still further embodiments, a primary INVADER assay reaction is carried out in solution with one of the hairpin structures of the present invention and one or more components of a secondary reaction are bound to a solid support (e.g., FRET cassette is bound to a solid support). In yet other embodiments, all of the components necessary for an INVADER assay reaction, including cleavage agents, are bound to a solid support.

The present invention is not limited to the configurations described herein. Indeed, one skilled in the art recognizes that any number of additional configurations may be utilized. Any configuration that supports a detectable invasive cleavage reaction may be utilized. Additional configurations are identified using any suitable method, including, but not limited to, those disclosed herein.

1. Probe Oligonucleotide Bound

In some embodiments, the probe oligonucleotide is bound to a solid support. In some embodiments, the probe is a labeled Signal Probe oligonucleotide. The signal probe is cleaved to release a signal molecule indicative of the presence of a given target molecule (e.g., a hairpin structure of the present invention). In some embodiments, the signal molecule is a fluorescence donor in an energy transfer reaction (e.g., FRET), whose emission increases in response to separation from a quenching fluorescence acceptor. In other embodiments, the signal molecule is a fluorescent moiety that is detected only upon its release into solution. It yet other embodiments, the signal molecule is a fluorescently labeled small molecule that is separated from the full length Signal Probe by carrying a distinct charge.

In some embodiments, a system is designed in which no separation steps are required to visualize the signal generated by the reaction. In some embodiments, this is accomplished in the FRET system in which the fluorescence donor remains affixed to the solid support following cleavage of the signal probe. This design has several complexities that stem from the nature of the FRET reaction. The quenching in the FRET signal molecule is only 97-99% efficient (i.e. not all of the energy emitted by the donor will be absorbed by the quencher). To detect the fluorescence of the unquenched donor above the background of the uncleaved probes, it is necessary to cleave 1-3% of the probe molecules. Assuming that in a 100 μm×100 μm area, there are ~$10^8$ probes bound, then ~$10^6$ should be cleaved to generate a signal detectable above the inherent background generated by those probes. Probe cycling in an INVADER assay reaction on a single target molecule can generate approximately 1000-2000 cleaved probe molecules per hour (assuming a turnover rate of 15-30 events/target/min). Roughly 1000 target molecules are required to generate this level of cleaved Signal Probes. Assuming a reaction volume of 1 nL, the necessary target concentration becomes 1 pM, well within the range of the maximum that can be manipulated (e.g., 0.5-2.5 pM). At less than maximal probe densities, it would nonetheless be necessary to deliver at least 10-20 target molecules (i.e. a 10-20 fM solution) to each reaction area to ensure a statistical likelihood that each will contain target. The same target concentration considerations apply to other, non-FRET alternatives, for example, release of a single fluorescent group into solution, with or without a quenching fluorophore and release of a positively charged signal molecule even though <1% cleavage would be detectable with these other methods. Accordingly, in some embodiments, dilute solutions are used in conjunction with longer reaction times (e.g. a 100 fM solution could be applied and the reactions run for 10-24 hours).

2. INVADER Oligonucleotide Bound

In some embodiment of the present invention, the INVADER oligonucleotide is bound to the solid support and the 5' hairpin structure is free in solution. In this embodiment, there are no restrictions on the length of the INVADER oligonucleotide-target duplex, since the INVADER oligonucleotide does not need to cycle on and off the target, as does the signal probe. Thus, in some embodiments where the INVADER oligonucleotide is bound to a solid support, the INVADER oligonucleotide is used as a "capture" oligonucleotide to concentrate target molecules (e.g., 5' hairpin structures) from solution onto the solid phase through continuous application of sample to the solid support. For example, by applying 1 ml of a 1 mg/ml target solution, it is possible to bind $10^6$-$10^8$ target molecules in a 100 μM×100 μM area. Moreover, because the INVADER oligonucleotide-target interaction is designed to be stable, in some embodiments, the support is washed to remove unbound target and unwanted sample impurities prior to applying the signal probes, enzyme, etc., to ensure even lower background levels. In other embodiments, a capture oligonucleotide complementary to a distinct region in the proximity of the locus being investigated is utilized.

Numerous possibilities exist for separation of cleaved from uncleaved signal probe reactions where INVADER oligonucleotides are bound the solid support and 5' hairpin (or double hairpin) structures are free in solution. In certain embodiments, a labeling strategy is utilized that makes it possible to chemically differentiate cleaved from uncleaved 5' hairpin structures since both full length 5' hairpin structures and cleaved 5' hairpin structures are in solution.

3. Both Hairpin Structure and INVADER or Probe Oligonucleotide Bound

In some embodiments of the present invention, both the hairpin structure and the probe or INVADER oligonucleotide are bound to a solid support. In preferred embodiments, the hairpin structure and the probe or INVADER oligonucleotides are placed in close proximity on the same solid support such that they may interact. In some embodiments, the sequences are attached via spacer molecules in order to improve their accessibility.

In some preferred embodiments, a single INVADER oligonucleotide is configured to allow it to contact and initiate multiple cleavage reactions with multiple 5' hairpin structures. For example, in some embodiments, one INVADER oligonucleotide is surrounded on a solid support by multiple 5' hairpin structures.

4. Secondary Reaction Bound

In some embodiments, a primary INVADER assay reaction is performed in solution and a secondary reaction is performed on a solid support. Cleaved off portion from a 5' hairpin structure from the primary INVADER assay reaction are contacted with a solid support containing one or more components of a cleavage structure, including but not limited to a secondary target nucleic acid, a secondary probe or a secondary INVADER oligonucleotide. In a preferred embodiment, the component is a one-piece secondary oligonucleotide, or cassette, comprising both a secondary target portion and a secondary probe portion. In a particularly preferred embodiment, the cassette is labeled to allow detection of cleavage of the cassette by a FRET. The secondary signal oligonucleotide may be labeled using any suitable method including, but not limited to, those disclosed herein. It will be appreciated that any of the embodiments described above for configuring an INVADER assay reaction on a support may be used in configuring a secondary or subsequent INVADER assay reaction on a support.

5. Hairpin Structure Bound

In some embodiments of the present invention, the hairpin structure (e.g., 3', 5', or double hairpin structure) is bound to the solid support. In some embodiments, the INVADER or Probe oligonucleotides are free in solution. In yet other embodiments, a secondary oligonucleotide (e.g., a FRET oligonucleotide) is included in the reaction. In some embodiments, the FRET oligonucleotide is free in solution. In other embodiments, the FRET oligonucleotide is bound to the solid support.

6. Enzyme Bound

In some embodiments, the cleavage agent (e.g., enzyme) is bound to a solid support. Any suitable method may be used for the attachment of a cleavage enzyme to a solid support, including, but not limited to, covalent attachment to a support (See e.g., Chemukhin and Klenova, Anal. Biochem., 280:178 [2000]), biotinylation of the enzyme and attachment via avidin (See e.g., Suter et al., Immunol. Lett. 13:313 [1986]), and attachment via antibodies (See e.g., Bilkova et al., J. Chromatogr. A, 852:141 [1999]).

7. Spacers

In some embodiments of the present invention, oligonucleotides are attached to a solid support via a spacer or linker molecule. The present invention is not limited to any one mechanism. Indeed, an understanding of the mechanism is not necessary to practice the present invention. Nonetheless, it is contemplated that spacer molecules enhance INVADER assay reactions by improving the accessibility of oligonucleotides and decreasing interactions between oligonucleotides. The use of linkers, which can be incorporated during oligonucleotide synthesis, has been shown to increase hybridization efficiency relative to capture oligonucleotides that contain no linkers (Guo et al., Nucleic Acids Res., 22:5456 [1994]; Maskos and Southern, Nucleic Acids Res., 20:1679 [1992]; Shchepinov et al., Nucleic Acids Research 25:1155 [1997]).

Spacer molecules may be comprised of any suitable material. Preferred materials are those that are stable under reaction conditions utilized and non-reactive with the components of the INVADER assay. Suitable materials include, but are not limited to, carbon chains (e.g., including but not limited to $C_{18}$), polynucleotides (e.g., including, but not limited to, polyI, polyT, polyG, polyC, and polyA), and polyglycols (e.g., hexaethylene glycol).

Spacer molecules may be of any length. Accordingly in some embodiments, multiple spacer molecules are attached end to end to achieve the desired length spacer. For example, in some embodiments, multiple $C_{18}$ or hexaethylene glycol spacers (e.g., including, but not limited to, 5, 10, or 20 spacer molecules) are combined. The optimum spacer length is dependent on the particular application and solid support used. To determine the appropriate length, different lengths are selected (e.g., 5, 10, or 20 $C_{18}$ or hexaethylene glycol spacers molecules) and reactions are performed as described herein to determine which spacer gives the most efficient reaction.

8. Solid Supports

The present invention is not limited to any one solid support. In some embodiments, reactions are performed on microtiter plates (e.g., polystyrene plates containing either containing 96 or 384 wells). For example, in some embodiments, streptavidin (SA) coated 96-well or 384-well microtiter plates (Boehringer Mannheim Biochemicals, Indianapolis, Ind.) are used as solid supports. In such embodiments, signal can be measured using standard fluorescent, chemiluminescent or colorimetric microtiter plate readers.

In some embodiments, INVADER assay reactions are carried out on particles or beads. The particles can be made of any suitable material, including, but not limited to, latex. In some embodiments, columns containing a particle matrix suitable for attachment of oligonucleotides are used. In a some embodiments, reactions are performed in minicolumns (e.g. DARAS, Tepnel, Cheshire, England). The columns contain microbeads to which oligonucleotides are covalently bound and subsequently used as capture probes or in enzymatic reactions. The use of minicolumns allows approximation of the bound oligonucleotide concentrations that will be attainable in a miniaturized chip format. Oligonucleotide binding is limited by the capacity of the support (i.e. $\sim 10^{12}/cm^2$). Thus, bound oligonucleotide concentration can only be increased by increasing the surface area to volume ratio of the reaction vessel. For example, one well of a 96-well microtiter plate, with a surface area of $\sim 1$ $cm^2$ and a volume of 400 µl has a maximal bound oligonucleotide concentration of $\sim 25$ nM. On the other hand, a 100 µm×100 µm×100 µM volume in a microchip has a surface area of $10^4$ µm$^2$ and a volume of 1 nL, resulting in a bound oligonucleotide concentration of 0.2 µM. Similar increased surface area: volume ratios can be obtained by using microbeads. Given a binding capacity of $\geq 10^{14}$ oligonucleotides in a 30 µl volume, these beads allow bound oligonucleotide concentrations of 0.2-10 µM, i.e. comparable to those anticipated for microchips.

In some embodiments, INVADER reactions are carried out on a HydroGel (Packard Instrument Company, Meriden, Conn.) support. HydroGel is porous 3D hydrophilic polymer matrix. The matrix consists of a film of polyacrylamide polymerized onto a microscope slide. A coupling moiety is co-polymerized into the matrix that permits the immobilization of aminated oligonucleotide molecules by reductive amination. Covalent attachment by amine groups permits the immobilization of nucleic acid probes at specific attachment points (usually their ends), and the hydrogel provides a 3D matrix approximating a bulk solution phase, avoiding a solid/solution phase interface.

In other embodiments, INVADER reactions are conducted on a solid support using a BEADARRAY (Illumina, San Diego, Calif.) technology. The technology combines fiber optic bundles and beads that self-assemble into an array. Each fiber optic bundle contains thousands to millions of individual fibers depending on the diameter of the bundle. Sensors are affixed to each bead in a given batch. The particular molecules on a bead define that bead's function as a sensor. To form an array, fiber optic bundles are dipped into pools of coated beads. The coated beads are drawn into the wells, one bead per well, on the end of each fiber in the bundle. The present invention is not limited to the solid supports described above. Indeed, a variety of other solid supports are contemplated including, but not limited to, glass microscope slides, glass wafers, gold, silicon, microchips, and other plastic, metal, ceramic, or biological surfaces.

9. Surface Coating and Attachment Chemistries

In some embodiments of the present invention, solid supports are coated with a material to aid in the attachment of oligonucleotides. The present invention is not limited to any one surface coating. Indeed, a variety of coatings are contemplated including, but not limited to, those described below.

In some embodiments, solid support INVADER assay reactions are carried out on solid supports coated with gold. The gold can be attached to any suitable solid support including, but not limited to, microparticles, microbeads, microscope slides, and microtiter plates. In some embodiments, the gold is functionalized with thiol-reactive maleimide moieties that can be reacted with thiol modified DNA (See e.g., Frutos et al., Nuc. Acid. Res., 25:4748 [1997]; Frey and Corn, Analytical Chem, 68:3187 [1996]; Jordan et al., Analytical Chem, 694939 [1997]; and U.S. Pat. No. 5,472,881; herein incorporated by reference).

In other embodiments, solid support INVADER assay reactions are carried out on supports coated with silicon. The silicon can be attached to any suitable support, including, but not limited to, those described above and in the illustrative examples provided below.

Additionally, in some embodiments, solid supports are coated with a molecule (e.g., a protein) to aid in the attachment of nucleic acids. The present invention is not limited to any particular surface coating. Any suitable material may be utilized including, but not limited to, proteins such as streptavidin. Thus, in some embodiments, oligonucleotides are attached to solid supports via terminal biotin or $NH_2$-mediated linkages included during oligonucleotide synthesis. INVADER oligonucleotides are attached to the support at their 5' ends and Signal Probes are attached at their 3' ends. In some embodiment, oligonucleotides are attached via a linker proximal to the attachment point. In a preferred embodiment, attachment is via a 40 atom linker with a low negative charge density as described in (Shchepinov et al., Nucleic Acids Research 25: 1155 [1997]).

In other embodiments, oligonucleotides are attached to solid support via antigen:antibody interaction. For Example, in some embodiments, an antigen (e.g., protein A or Protein G) is attached to a solid support and IgG is attached to oligonucleotides. In other embodiments, IgG is attached to a solid support and an antigen (e.g., Protein A or Protein G) is attached to oligonucleotides.

10. Addressing of Oligonucleotides

In some embodiments, oligonucleotides are targeted to specific sites on the solid support. As noted above, when multiple oligonucleotides are bound to the solid support, the oligonucleotides may be synthesized directly on the surface using any number of methods known in the art (e.g., including but not limited to methods described in PCT publications WO 95/11995, WO 99/42813 and WO 02/04597, and U.S. Pat. Nos. 5,424,186; 5,744,305; and 6,375,903, each incorporated by reference herein).

Any number of techniques for the addressing of oligonucleotides may be utilized. For example, in some embodiments, solid support surfaces are electrically polarized at one given site in order to attract a particular DNA molecule (e.g., Nanogen, CA). In other embodiments, a pin tool may be used to load the array mechanically (Shalon, Genome Methods, 6:639 [1996]. In other embodiments, ink jet technology is used to print oligonucleotides onto an active surface (e.g., O'Donnelly-Maloney et al., Genetic Analysis:Biomolecular Engineering, 13:151 [1996]).

In some preferred embodiments utilizing gold surfaces, the gold surfaces are further modified to create addressable DNA arrays by photopatterning self-assembled monolayers to form hydrophilic and hydrophobic regions. Alkanethiol chemistry is utilized to create self-assembled monolayers (Nuzzo et al., JACS, 105:4481 [1983]). DNA is placed on the hydrophilic regions by using an automated robotic device (e.g., a pin-loading tool).

D. Reaction Vessels

The methods of the present invention may be performed using any suitable reaction vessel. As used herein, the term "reaction vessel" refers to a system in which a reaction may be conducted, including but not limited to test tubes, wells, microwells (e.g., wells in microtitre assay plates such as, 96-well, 384-well and 1536-well assay plates), capillary tubes, ends of fibers such as optical fibers, microfluidic devices such as fluidic chips, cartridges and cards (including but not limited to those described, e.g., in U.S. Pat. No. 6,126,899, to Woudenberg, et al., U.S. Pat. Nos. 6,627,159, 6,720,187, and 6,734,401 to Bedingham, et al., U.S. Pat. Nos. 6,319,469 and 6,709,869 to Mian, et al., U.S. Pat. Nos. 5,587, 128 and 6,660,517 to Wilding, et al.), or a test site on any surface (including but not limited to a glass, plastic or silicon surface, a bead, a microchip, or an non-solid surface, such as a gel or a dendrimer).

In some preferred embodiments, reactions are conducted using a 3M microfluidic card (3M, St. Paul, Minn.). The 3M card has 8 loading ports, each of which is configured to supply liquid reagent to 48 individual reaction chambers upon centrifugation of the card. The reaction chambers contain pre-dispensed and dried assay reaction components for detection of target nucleic acids. These reagents are dissolved when they come in contact with the liquid reagents upon centrifugation of the card.

EXPERIMENTAL

In the disclosure that follows, the following abbreviations apply: Ex. (Example); Fig. (Figure); ° C. (degrees Centigrade); g (gravitational field); hr (hour); min (minute); olio (oligonucleotide); rxn (reaction); vol (volume); w/v (weight to volume); v/v (volume to volume); BSA (bovine serum albumin); CTAB (cetyltrimethylammonium bromide); HPLC (high pressure liquid chromatography); DNA (deoxyribonucleic acid); p (plasmid); μl (microliters); ml (milliliters); ng (nanograms); μg (micrograms); mg (milligrams); M (molar); mM (milliMolar); μM (microMolar); pmoles (picomoles); amoles (attomoles); zmoles (zeptomoles); nm (nanometers); kdal (kilodaltons); OD (optical density); EDTA (ethylene diamine tetra-acetic acid); FITC (fluorescein isothiocyanate) FAM (fluorescein); SDS (sodium dodecyl sulfate); NaPO4 (sodium phosphate); NP-40 (Nonidet P-40); Tris (tris(hydroxymethyl)-aminomethane); PMSF (phenylmethylsulfonylfluoride); TBE (Tris-Borate-EDTA, i.e., Tris buffer titrated with boric acid rather than HCl and containing EDTA); PBS (phosphate buffered saline); PPBS (phosphate buffered saline containing 1 mM PMSF); PAGE (polyacrylamide gel electrophoresis); Tween (polyoxyethylene-sorbitan); Red or RED (REDMOND RED Dye, Epoch Biosciences, Bothell Wash.) Z28 (ECLIPSE Quencher, Epoch Biosciences, Bothell, Wash.); Promega (Promega, Corp., Madison, Wis.); Glen Research (Glen Research, Sterling, Va.); Coriell (Coriell Cell Repositories, Camden, N.J.); Third Wave Technologies (Third Wave Technologies, Madison, Wis.); Microsoft (Microsoft, Redmond, Wash.); Qiagen (Qiagen, Valencia, Calif.);

The following examples are provided in order to demonstrate and further illustrate certain preferred embodiments and aspects of the present invention and are not to be construed as limiting the scope thereof.

Example 1

CFTR Allele Detection with Snap-Back Primers

This Examples describes the use of snap-back primers to detect various CFTR alleles using genomic DNA and artificial samples. The samples tested were as follows: Coriell 28 gDNA (CFTR 1717-1G>A HET sample); Pooled Amplicon Control 2 (CFTR G542X HET); Coriell 15 gDNA (CFTR G551D HET sample); Coriell 9 gDNA (CFTR R560T HET sample); Coriell 39 gDNA (Wild type for all CFTR mutations tested). The reagents employed are listed in Tables 1 and 2:

TABLE 1

3.33x Invader-plus Buffer

| Component | 1x Final Reaction | | 3.33x Formulation | |
|---|---|---|---|---|
| | Conc. | Units | Conc. | Units |
| MOPS | 10 | mM | 33.300 | mM |
| MgCl2 | 7.5 | mM | 24.975 | mM |
| dATP | 0.025 | mM | 0.083 | mM |
| dUTP | 0.025 | mM | 0.083 | mM |
| dGTP | 0.025 | mM | 0.083 | mM |
| dCTP | 0.025 | mM | 0.083 | mM |

TABLE 2

10x Invader-plus Enzyme Mix

| Component | 1x Final Reaction | | 10x Formulation | |
|---|---|---|---|---|
| | Conc. | Units | Conc. | Units |
| Cleavase VIII | 6.67 | ng/ul | 66.70 | ng/ul |
| Taq Polymerase | 0.066 | U/ul | 0.66 | U/ul |
| M Tris | 0.983 | mM | 8.93 | mM |
| M KCl | 2.23 | mM | 22.33 | mM |
| Tween 20 | 0.02 | % | 0.22 | % |
| Nonidet P40 | 0.02 | % | 0.22 | % |
| Glycerol | 2.23 | % | 22.33 | % |
| mg/ml BSA | 4.65 | ug/ml | 44.65 | ug/ml |

Figure 6:
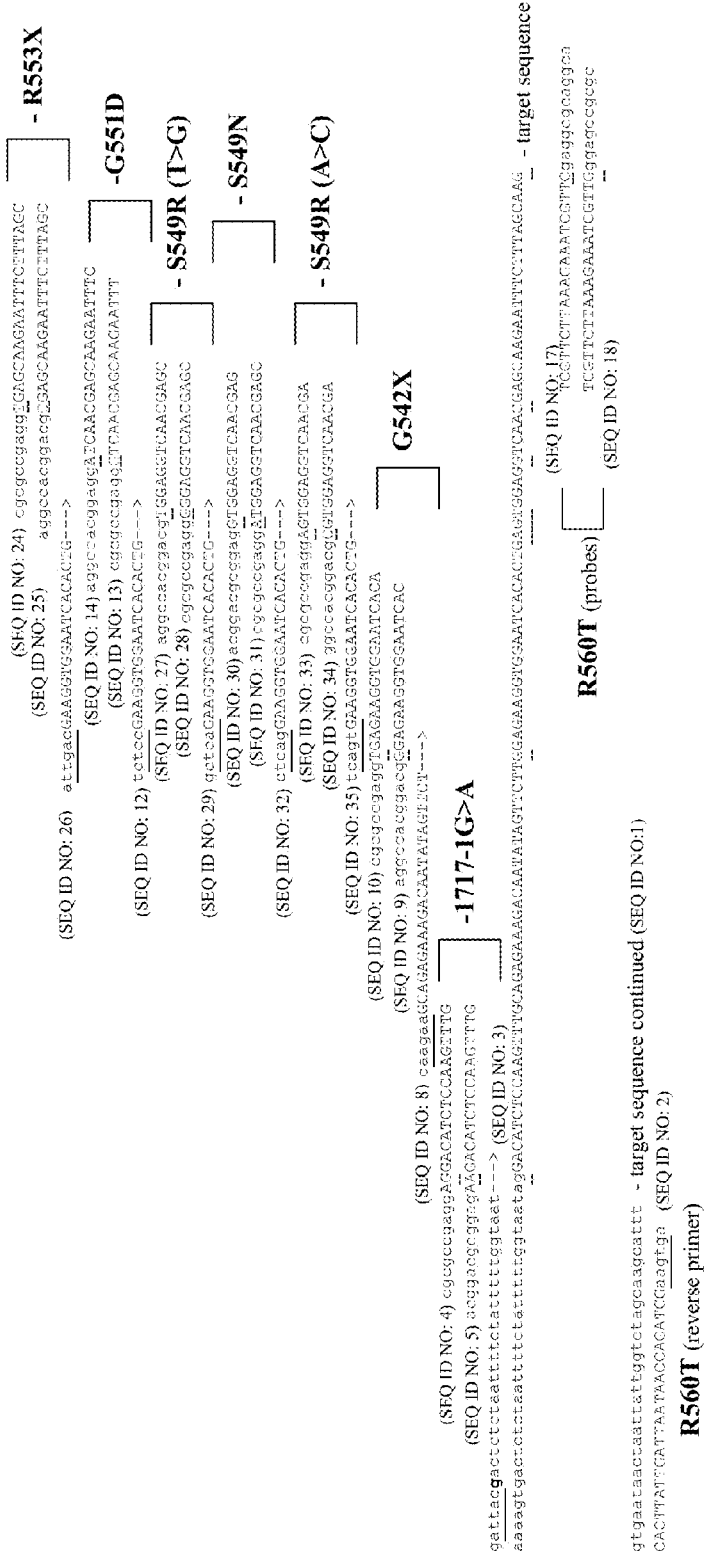
FIG. 6 shows various snap-back assay designs configured to detect various CFTR alleles, including: R553X, G551D, S549R (T>G), S549N, S549R (A>C), G542X, 1717-1G>A, and R560T. For each allele, a snap-back primer is shown, as well as two downstream probes (one for detecting the mutant allele and one for detecting wild type). Each of the snap-back primers is configured to generate a 3' hairpin structure in combination with the reverse primer (SEQ ID NO:2) and the target nucleic acid (SEQ ID NO:1). For each assay, the polymorphic base in the target nucleic acid is shown underlined, with the corresponding position in the probes also underlined. Also, for each snap-back primer, a portion of the 3' region is underlined. This portion of the snap-back primer is configured, once amplified, to generate the 3' snap-back portion (that hybridizes immediately before the nucleotide to be detected) that can hybridize to a non-adjacent portion to generate the 3' hairpin structure.

The oligonucleotide mixes and oligonucleotide sequences employed are shown in Table 3 below, and are also shown in FIG. 6.

TABLE 3

| SEQ ID NO | Final Conc. | Oligo Type | Sequence (5'>3') |
|---|---|---|---|
| CFTR 1717-1G > A Mix | | | |
| SEQ ID NO: 3 | 0.5 uM | snap-back primer | 5' GATTACGACTCTCTAATTTTCTATTTTTGGTAAT |
| SEQ ID NO: 2 | 0.5 uM | reverse primer | 5' AGTGAAGCTAGACCAATAATTAGTTCTTCAC |
| SEQ ID NO: 4 | 0.67 uM | probe oligo | 5' CGCGCCGAGGAGGACATCTCCAAGTTTG-hex |
| SEQ ID NO: 5 | 0.67 uM | probe oligo | 5' ACGGACGCGGAGAAGACATCTCCAAGTTTG-hex |
| SEQ ID NO: 6 | 0.25 uM | FRET cassette | 5' 1TCTXAAGCCGGTTTTCCGGCTGAGACCTCGGCGCG-hex |
| SEQ ID NO: 7 | 0.25 uM | FRET cassette | 5' 2TCTXTTCGGCCTTTTGGCCGAGAGACTCCGCGTCCGT-hex |
| CFTR G542X Oligo Mix | | | |
| SEQ ID NO: 8 | 0.5 uM | snap-back primer | 5' CAAGAAGCAGAGAAAGACAATATAGTTCT |
| SEQ ID NO: 2 | 0.5 uM | reverse primer | 5' AGTGAAGCTAGACCAATAATTAGTTCTTCAC |
| SEQ ID NO: 9 | 0.67 uM | probe oligo | 5' AGGCCACGGACGGGAGAAGGTGGAATCAC-hex |
| SEQ ID NO: 10 | 0.67 uM | probe oligo | 5' CGCGCCGAGGTGAGAAGGTGGAATCACA-hex |
| SEQ ID NO: 11 | 0.25 uM | FRET cassette | 5' 2TCTXTTCGGCCTTTTGGCCGAGAGACGTCCGTGGCCT-hex |
| SEQ ID NO: 6 | 0.25 uM | FRET cassette | 5' 1TCTXAAGCCGGTTTTCCGGCTGAGACCTCGGCGCG-hex |
| CFTR G551D Oligo Mix | | | |
| SEQ ID NO: 12 | 0.5 uM | snap-back primer | 5' TCTCCGAAGGTGGAATCACACTG |
| SEQ ID NO: 2 | 0.5 uM | reverse primer | 5' AGTGAAGCTAGACCAATAATTAGTTCTTCAC |
| SEQ ID NO: 13 | 0.67 uM | probe oligo | 5' CGCGCCGAGGGTCAACGAGCAAGAATTT-hex |
| SEQ ID NO: 14 | 0.67 uM | probe oligo | 5' AGGCCACGGACGATCAACGAGCAAGAATTTC-hex |
| SEQ ID NO: 15 | 0.25 uM | FRET cassette | 5' 2TCTXTTCGGCCTTTTGGCCGAGAGACCTCGGCGCG-hex |
| SEQ ID NO: 16 | 0.25 uM | FRET cassette | 5' 1TCTXAAGCCGGTTTTCCGGCTGAGACGTCCGTGGCCT-hex |
| CFTR R560T Oligo Mix | | | |
| SEQ ID NO: 12 | 0.5 uM | snap-back primer | 5' TCTCCGAAGGTGGAATCACACTG |
| SEQ ID NO: 2 | 0.5 uM | reverse primer | 5' AGTGAAGCTAGACCAATAATTAGTTCTTCAC |
| SEQ ID NO: 17 | 0.67 uM | probe oligo | 5' ACGGACGCGGAGCTTGCTAAAGAAATTCTTGCT-hex |

TABLE 3-continued

| SEQ ID NO | Final Conc. | Oligo Type | Sequence (5'>3') |
|---|---|---|---|
| SEQ ID NO: 18 | 0.67 uM | probe oligo | 5' CGCGCCGAGGGTTGCTAAAGAAATTCTTGCT-hex |
| SEQ ID NO: 19 | 0.25 uM | FRET cassette | 5' 1TCTXAAGCCGGTTTTCCGGCTGAGACTCCGCGTCCGT-hex |
| SEQ ID NO: 15 | 0.25 uM | FRET cassette | 5' 2TCTXTTCGGCCTTTTGGCCGAGAGACCTCGGCGCG-hex |

X = Z28 Phosphoramidite
1 = 6 FAM Amidite
2 = Z35 (Red Dye) Phosphoramidite
hex = hexanediol The method employed for each oligo mix was as follows. First, a signal mix for each oligo mix was made as follows:

| | |
|---|---|
| 3.33x Oligo Mix | 82.5 ul |
| 3.33x Invader-plus Buffer | 82.5 ul |
| 10x Invader-plus Enzyme Mix | 27.5 ul |
| RNase Free Water | 27.5 ul |
| | 220 ul |

Next 5 ul of sample was added to wells as shown below:

| | 1 | 2 | 3 | 4 | 5 | 6 | 7 | 8 | 9 | 10 | 11 | 12 |
|---|---|---|---|---|---|---|---|---|---|---|---|---|
| A | tRNA | tRNA | tRNA | c 28 | c 28 | c 28 | C 39 | C 39 | C 39 | | | |
| B | | | | | | | | | | | | |
| C | tRNA | tRNA | tRNA | PAC 2 | PAC 2 | PAC 2 | C 39 | C 39 | C 39 | | | |
| D | | | | | | | | | | | | |
| E | tRNA | tRNA | tRNA | c 15 | c 15 | c 15 | C 39 | C 39 | C 39 | | | |
| F | | | | | | | | | | | | |
| G | tRNA | tRNA | tRNA | c 9 | c 9 | c 9 | C 39 | C 39 | C 39 | | | |
| H | | | | | | | | | | | | | c = Coriell gDNA at 5 ng/ul
C = Coriell gDNA at 35 ng/ul

Then, 20 ul of the appropriate signal mix was added to the wells as shown below, with mixing accomplished by pipetting.

| | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | | CFTR 1717-1G > A Signal Mix | | | | | | | | | | |
| C | | CFTR G542X Signal Mix | | | | | | | | | | |
| D | | | | | | | | | | | | |
| E | | CFTR G551D Signal Mix | | | | | | | | | | |
| F | | | | | | | | | | | | |
| G | | CFTR R560T Signal Mix | | | | | | | | | | |
| H | | | | | | | | | | | | |

The plate was then sealed with ABI optical plate sealer. The plate was then spun for one minute at 1200 rpm to bring down any liquid on the wall and get rid of bubbles. The plate was then run in a HYBAID PCR express thermocylcer using the following profile:

| Step | Temp ° C. | Time | Cycles |
|---|---|---|---|
| Denature | 95 | 2 min. | 2 |
| Anneal | 55 | 1 min. | |
| Extend | 63 | 2 min. | |
| Denature | 95 | 30 sec. | 18 |
| Anneal | 55 | 30 sec. | |
| Extend | 68 | 1 min. | |
| Taq Heat Kill | 99 | 10 min. | 1 |
| INVADER Reaction | 63 | 30 min. | |
| Hold | 10 | | |

The plate was then spun briefly at 1200 rpm to bring down any condensation. The plate was then read on a GENIOS plate reader using the following setting:

| | Read 1 | Read 2 |
|---|---|---|
| Measurement mode: | Fluorescence Top | Fluorescence Top |
| Excitation wavelength (nm): | 485 | 560 |
| Emission wavelength (nm): | 535 | 612 |
| Gain: | 45 | 65 |
| Number of flashes: | 10 | 10 |
| Lag time (μs): | 0 | 0 |
| Integration time (μs): | 20 | 20 |
| Plate definition file: | MJ-Skirted Plate.pdf | MJ-Skirted Plate.pdf |

The results of the assay are shown in Tables 4a (average raw signal), and Table 4b (Fold Over Zero and Ratio).

TABLE 4

A. Average Raw Signal

| | NTC | | Sample 1 (HET) | | Sample 2 (WT) | |
|---|---|---|---|---|---|---|
| | FAM | Red | FAM | Red | FAM | Red |
| 1717-1 G > A | 1865 | 1307 | 6897 | 1054 | 9414 | 707 |
| G542X | 2433 | 908 | 2793 | 1540 | 1302 | 2356 |
| G551D | 4078 | 426 | 5154 | 1250 | 2087 | 4038 |
| R560T | 4226 | 448 | 4225 | 2560 | 6639 | 434 |

TABLE 4-continued

B. FOZ and Ratio

|  | FAM | Red | Ratio |
|---|---|---|---|
| Sample 1 (HET) | | | |
| 1717-1 G > A | 3.70 | 0.81 | 269.88 |
| G542X | 1.15 | 1.70 | 4.70 |
| G551D | 1.26 | 2.93 | 7.32 |
| R560T | 1.00 | 5.71 | 470.93 |

TABLE 4-continued

Sample 2 (WT)

| 1717-1 G > A | 5.05 | 0.54 | 404.88 |
|---|---|---|---|
| G542X | 0.54 | 2.60 | 159.57 |
| G551D | 0.51 | 9.47 | 847.03 |
| R560T | 1.57 | 0.97 | −0.06 |

These results show that there is target specific signal generation, indicating that the snap-back primers are forming structures that provide the upstream (INVADER) oligonucleotide as part of a 3' hairpin structure. These results also indicate that more cycles of amplification may be useful for generating a stronger signal.

Example 2

Separate Analysis of PCR and Invasive Cleavage Assays Components

This Examples describes the separate analysis of the PCR and INVADER assay components of the INVADER-plus reaction described in Example 1 in order to determine the source of the FAM background of Example 1. The buffer mix, enzyme mix, and oligo mixes were all the same as in Example 1. The samples employed were as follows:
Coriell 28 gDNA (CFTR 1717-1G>A HET sample)
Coriell 18 gDNA (CFTR G542X HET)
Coriell 15 gDNA (CFTR G551D HET sample)
Coriell 9 gDNA (CFTR R560T HET sample)
Coriell 39 gDNA (Wild type for all CFTR mutations tested)
A signal mix for each oligo mix was made as follows:

| 3.33x Oligo Mix | 75 ul |
|---|---|
| 3.33x Invader-plus Buffer | 75 ul |
| 10x Invader-plus Enzyme Mix | 25 ul |
| RNase Free Water | 25 ul |
| | 200 ul |

Amplification mixes for PCR INVADER reactions were made as follows:

| 10x Primer Mix | 20 ul |
|---|---|
| 3.33x Invader-plus Buffer | 75 ul |
| 10x Invader-plus Enzyme Mix | 25 ul |
| RNase Free Water | 30 ul |
| | 200 ul |

Five ul of sample was added to wells as shown below:

| | 1 | 2 | 3 | 4 | 5 | 6 | 7 | 8 | 9 | 10 | 11 | 12 |
|---|---|---|---|---|---|---|---|---|---|---|---|---|
| A | C 39 | C 39 | C 39 | C 39 | | | | | C 39 | C 39 | C 39 | C 39 |
| B | C 39 | C 39 | C 39 | C 39 | | | | | C 39 | C 39 | C 39 | C 39 |
| C | C 39 | C 39 | C 39 | C 39 | | | | | C 39 | C 39 | C 39 | C 39 |
| D | c 28 | c 18 | c 15 | c 9 | | | | | c 28 | c 18 | c 15 | c 9 |
| E | c 28 | c 18 | c 15 | c 9 | | | | | c 28 | c 18 | c 15 | c 9 |
| F | c 28 | c 18 | c 15 | c 9 | | | | | c 28 | c 18 | c 15 | c 9 |
| G | tRNA | tRNA | tRNA | tRNA | | | | | tRNA | tRNA | tRNA | tRNA |
| H | tRNA | tRNA | tRNA | tRNA | | | | | tRNA | tRNA | tRNA | tRNA | c = Coriell gDNA at 5 ng/ul
C = Coriell gDNA at 35 ng/ul

Twenty ul or INVADER-plus signal mix or 15 ul of PCR INVADER amplification mix was added to the wells as shown below, using pipetting for mixing.

| | 1 | 2 | 3 | 4 | 5 | 6 | 7 | 8 | 9 | 10 | 11 | 12 |
|---|---|---|---|---|---|---|---|---|---|---|---|---|
| A | 1 | 2 | 3 | 4 | | | | | 5 | 6 | 7 | 7 |
| B | 1 | 2 | 3 | 4 | | | | | 5 | 6 | 7 | 7 |
| C | 1 | 2 | 3 | 4 | | | | | 5 | 6 | 7 | 7 |
| D | 1 | 2 | 3 | 4 | | | | | 5 | 6 | 7 | 7 |
| E | 1 | 2 | 3 | 4 | | | | | 5 | 6 | 7 | 7 |
| F | 1 | 2 | 3 | 4 | | | | | 5 | 6 | 7 | 7 |
| G | 1 | 2 | 3 | 4 | | | | | 5 | 6 | 7 | 7 |
| H | 1 | 2 | 3 | 4 | | | | | 5 | 6 | 7 | 7 |

1 = CFTR 1717-1G > A Signal Mix
2 = CFTR G542X Signal Mix
3 = CFTR G551D Signal Mix
4 = CFTR R560T Signal Mix
5 = CFTR 1717-1G > A Amplification Mix
6 = CFTR G542X Amplification Mix
7 = CFTR G551D/R560T Amplification Mix The plate was then sealed with ABI optical plate sealer. The plate was spun for one minute at 1200 rpm bring down any liquid on the wall and to get rid of bubbles. The plate was then run in a HYBAID PCR express thermocycler using the following profile.

| Step | Temp ° C. | Time | Cycles |
|---|---|---|---|
| Denature | 95 | 2 min. | 2 |
| Anneal | 55 | 1 min. | |
| Extend | 63 | 2 min. | |
| Denature | 95 | 30 sec. | 38 |
| Anneal | 55 | 30 sec. | |
| Extend | 68 | 1 min. | |
| Hold 1 | 10 | | |
| Taq Heat Kill | 99 | 10 min. | 1 |
| INVADER Reaction | 63 | 30 min. | |
| Hold 2 | 10 | | |

At hold step 1, using a razor blade, the ABI optical sealer was cut between columns 6 and 7 and the sealer from columns 7 through 12 was carefully removed. Five ul of the probe mix was then added to the wells (mixing by pipetting, being careful not to splash or generate bubbles) as shown below:

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   | A | B  | C  | D  |
| B |   |   |   |   |   |   |   |   | A | B  | C  | D  |
| C |   |   |   |   |   |   |   |   | A | B  | C  | D  |
| D |   |   |   |   |   |   |   |   | A | B  | C  | D  |
| E |   |   |   |   |   |   |   |   | A | B  | C  | D  |
| F |   |   |   |   |   |   |   |   | A | B  | C  | D  |
| G |   |   |   |   |   |   |   |   | A | B  | C  | D  |
| H |   |   |   |   |   |   |   |   | A | B  | C  | D  |

A = CFTR 1717-1G > A Probe Mix
B = CFTR G542X Probe Mix
C = CFTR G551D Probe Mix
D = CFTR R560T Probe Mix Columns 7 through 12 were then resealed with ABI optical plate sealer. The continue button on the thermocycler was pushed to continue cycling profile. The plate was then spun briefly at 1200 rpm to bring down any condensation. The plate was then read on a GENIOS plate reader with the following settings:

|                          | Read 1           | Read 2           |
|--------------------------|------------------|------------------|
| Measurement mode:        | Fluorescence Top | Fluorescence Top |
| Excitation wavelength (nm): | 485           | 560              |
| Emission wavelength (nm):   | 535           | 612              |
| Gain:                    | 40               | 65               |
| Number of flashes:       | 10               | 10               |
| Lag time (μs):           | 0                | 0                |
| Integration time (μs):   | 20               | 20               |

Figure 7A:
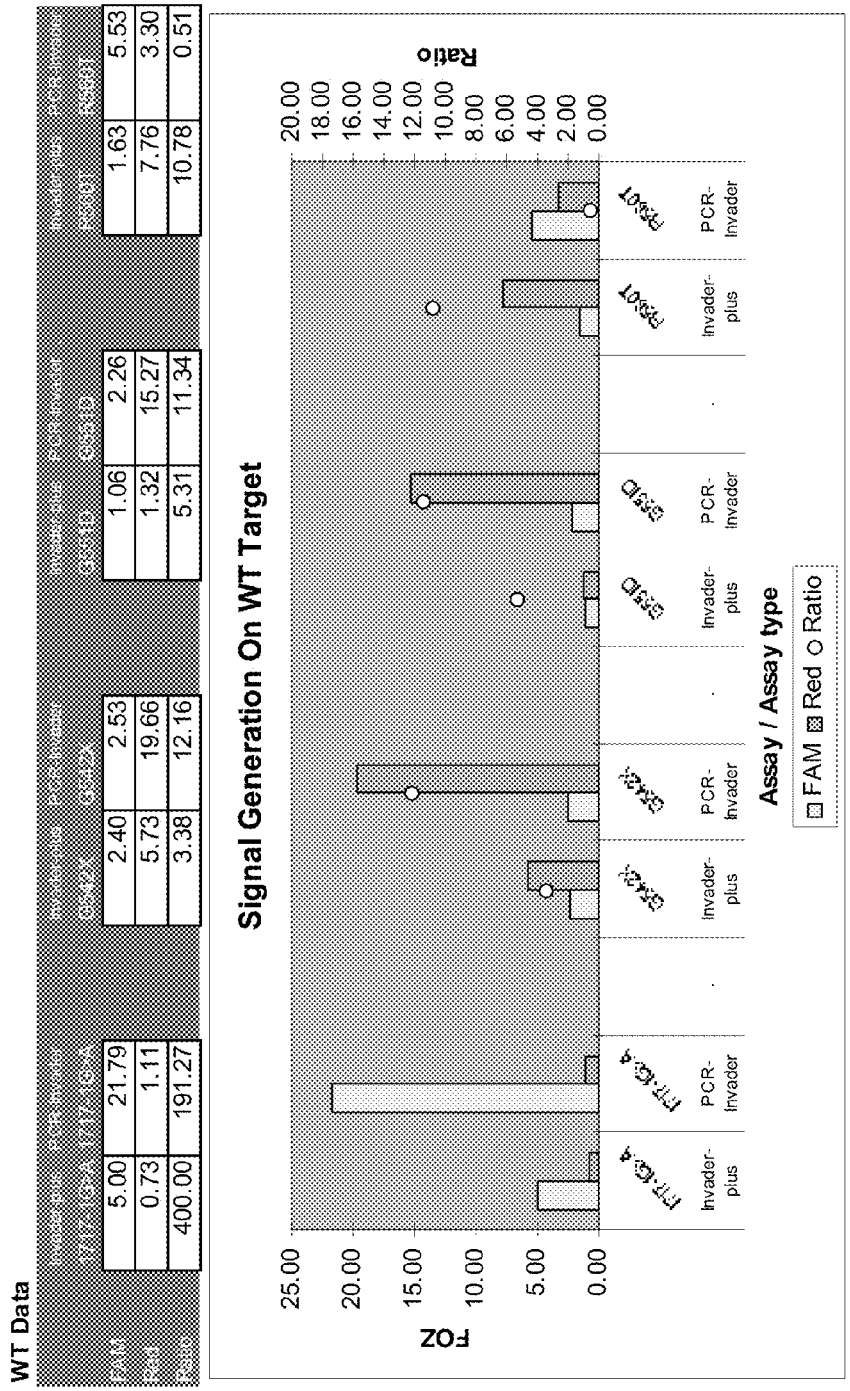
FIGS. 7A and 7B show the results, from Example 2, of detecting various CFTR alleles using snap-back primers to generate 3' hairpin structures that form invasive cleavage structure with upstream oligonucleotides.
Figure 7B:
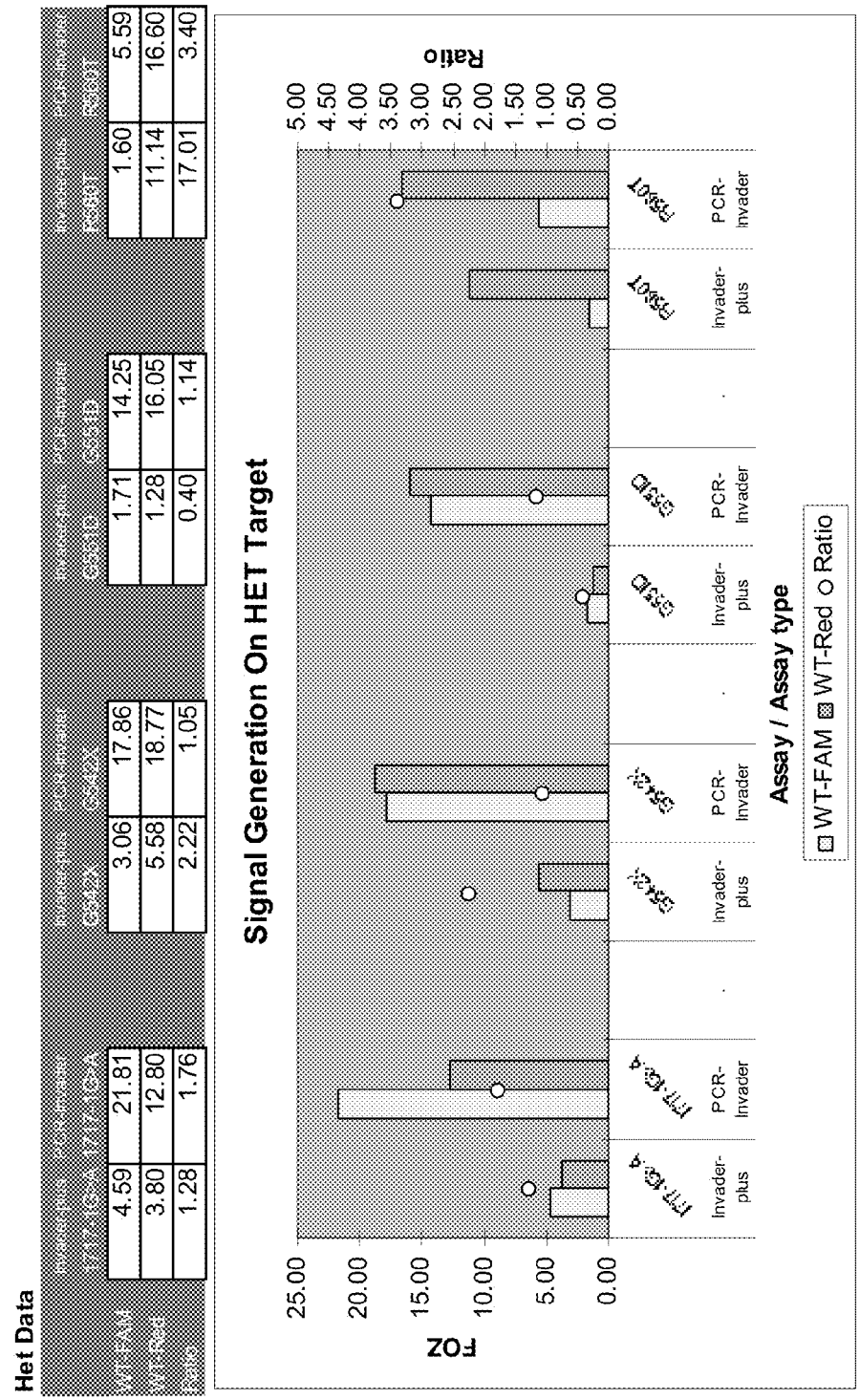

The results of the assay are shown in Tables 5a (FAM), Table 5b (Red), FIG. 7A (wild type data), and FIG. 7B (Heterozygous data).

TABLE 5

| | Invader-plus | | | | | PCR-Invader | | | |
|---|---|---|---|---|---|---|---|---|---|
| | 1717-1G > A | G542X | G551D | R560T | | 1717-1G > A | G542X | G551D | R560T |
| | | | | A. FAM | | | | | |
| WT-FAM  | 4875 | 3265 | 2437 | 3481 | WT-FAM  | 4402 | 531  | 636  | 2859 |
| HET-FAM | 4478 | 4161 | 3933 | 3415 | HET-FAM | 4406 | 3743 | 4012 | 2890 |
| NTC-FAM | 975  | 1360 | 2297 | 2140 | NTC-FAM | 202  | 210  | 282  | 517  |
| | | | | B. Red | | | | | |
| WT-Red  | 1120 | 6909 | 6424 | 4248 | WT-Red  | 357  | 5663 | 5381 | 1059 |
| HET-Red | 5827 | 6722 | 6229 | 6099 | HET-Red | 4121 | 5406 | 5656 | 5328 |
| NTC-Red | 1533 | 1206 | 4857 | 548  | NTC-Red | 322  | 288  | 353  | 321  |

These results show that additional cycles of PCR amplification generally assist in the generation of more signal over background. These results also shows that adding the probe mix after amplification generally helps reduce the level of signal generated in the background. CFTR 1717-1G>A, G542X, and G551D all give fair ratios for the HET samples but R560T still has problems with mutant signal generation. CFTR 1717-1G>A, G542X, and G551D have fair ratios for the wild type samples even though G542X is a little lower. R560T is generating a considerable amount mutant signal in the PCR INVADER reaction which was also observed in Example 1.

Example 3

Monoplex and Multiplex Detection with Snap-Back Primers

This Examples describes the use of snap-back primers in both monoplex and multiplex formats using the mixes described in Examples 1 and 2. Its is noted that, even though multiple amplicons are generated in reactions of this example, only probes for one mutation/polymorphism are used in the mix since these reactions are limited to two dyes (one for mutant and one for wild type). The samples, buffer mix, enzyme mix, and oligo mixes were all the same as in Example 2.

The monoplex oligo mixes for each allele (1717-1G>A, G542X, G551D, and R560T) were the same as shown in Example 1. The multiplex mixes were as follows. One mix, the "multiplex primer mix" contained all of the snap-back primers from Example 1, which includes SEQ ID NOs: 3, 8, and 12 (SEQ ID NO:12 is used for both G551D and R560T). Four other "probe/FRET" mixes were made, one for each allele, where each mix contained the probes and FRET cassettes described in Example 1 for each of the four CFTR alleles.

The signal mixes for monoplex INVADER-plus reactions were made as follows:

| 3.33x Oligo Mix          | 82.5 ul |
|--------------------------|---------|
| 3.33x Invader-plus Buffer | 82.5 ul |
| 10x Invader-plus Enzyme Mix | 27.5 ul |
| RNase Free Water         | 27.5 ul |
|                          | 220 ul  |

The signal mixes for multiplex INVADER-plus reaction were made as follows:

| 10x Primer Mix              | 27.5 ul |
| 5x Probe/FRET Mix           | 55 ul   |
| 3.33x Invader-plus Buffer   | 82.5 ul |
| 10x Invader-plus Enzyme Mix | 27.5 ul |
| RNase Free Water            | 27.5 ul |
|                             | 220 ul  |

Then, 5 ul of sample was added to the wells as indicated below:

|   | 1 | 2 | 3 | 4 | 5 | 6 | 7 | 8 | 9 | 10 | 11 | 12 |
|---|---|---|---|---|---|---|---|---|---|----|----|----|
| A | tRNA | tRNA | tRNA | c 28 | c 28 | c 28 | c 39 | c 39 | c 39 | | | |
| B | tRNA | tRNA | tRNA | c 18 | c 18 | c 18 | c 39 | c 39 | c 39 | | | |
| C | tRNA | tRNA | tRNA | c 15 | c 15 | c 15 | c 39 | c 39 | c 39 | | | |
| D | tRNA | tRNA | tRNA | c 9 | c 9 | c 9 | c 39 | c 39 | c 39 | | | |
| E | tRNA | tRNA | tRNA | c 28 | c 28 | c 28 | c 39 | c 39 | c 39 | | | |
| F | tRNA | tRNA | tRNA | c 18 | c 18 | c 18 | c 39 | c 39 | c 39 | | | |
| G | tRNA | tRNA | tRNA | c 15 | c 15 | c 15 | c 39 | c 39 | c 39 | | | |
| H | tRNA | tRNA | tRNA | c 9 | c 9 | c 9 | c 39 | c 39 | c 39 | | | | c = Coriell gDNA at 5 ng/ul

Twenty ul of signal mixes were added to wells as shown below, with mixing by pipetting:

|   | 1 | 2 | 3 | 4 | 5 | 6 | 7 | 8 | 9 | 10 | 11 | 12 |
|---|---|---|---|---|---|---|---|---|---|----|----|----|
| A | 1 | 1 | 1 | 1 | 1 | 1 | 1 | 1 | 1 | | | |
| B | 2 | 2 | 2 | 2 | 2 | 2 | 2 | 2 | 2 | | | |
| C | 3 | 3 | 3 | 3 | 3 | 3 | 3 | 3 | 3 | | | |
| D | 4 | 4 | 4 | 4 | 4 | 4 | 4 | 4 | 4 | | | |
| E | 5 | 5 | 5 | 5 | 5 | 5 | 5 | 5 | 5 | | | |
| F | 6 | 6 | 6 | 6 | 6 | 6 | 6 | 6 | 6 | | | |
| G | 7 | 7 | 7 | 7 | 7 | 7 | 7 | 7 | 7 | | | |
| H | 8 | 8 | 8 | 8 | 8 | 8 | 8 | 8 | 8 | | | |

1 = CFTR 1717-1G > A Monoplex Mix
2 = CFTR G542X Monoplex Mix
3 = CFTR G551D Monoplex Mix
4 = CFTR R560T Monoplex Mix
5 = CFTR 1717-1G > A Multiplex Mix
6 = CFTR G542X Multiplex Mix
7 = CFTR G551D Multiplex Mix
8 = CFTR R560T Multiplex Mix The plate was then sealed with ABI optical plate sealer and then spun for one minute at 1200 rpm to bring down any liquid on the walls and to get rid of bubbles. The plate was then run in a HYBAID PCR Express thermocycler using the following profile:

| Step | Temp ° C. | Time | Cycles |
|---|---|---|---|
| Denature | 95 | 2 min. | 2 |
| Anneal | 55 | 1 min. | |
| Extend | 66 | 2 min. | |

| Step | Temp ° C. | Time | Cycles |
|---|---|---|---|
| Denature | 95 | 30 sec. | 38 |
| Anneal | 55 | 30 sec. | |
| Extend | 68 | 1 min. | |
| Hold 1 | 10 | | |
| Taq Heat Kill | 99 | 10 min. | 1 |
| INVADER Reaction | 63 | 15 min. | |
| Hold 2 | 10 | | |

The plate was then read on a GENIOS plate reader using the following setting:

|   | Read 1 | Read 2 |
|---|---|---|
| Measurement mode: | Fluorescence Top | Fluorescence Top |
| Excitation wavelength (nm): | 485 | 560 |
| Emission wavelength (nm): | 535 | 612 |
| Gain: | 40 | 65 |
| Number of flashes: | 10 | 10 |
| Lag time (µs): | 0 | 0 |
| Integration time (µs): | 20 | 20 |

Figure 8A:
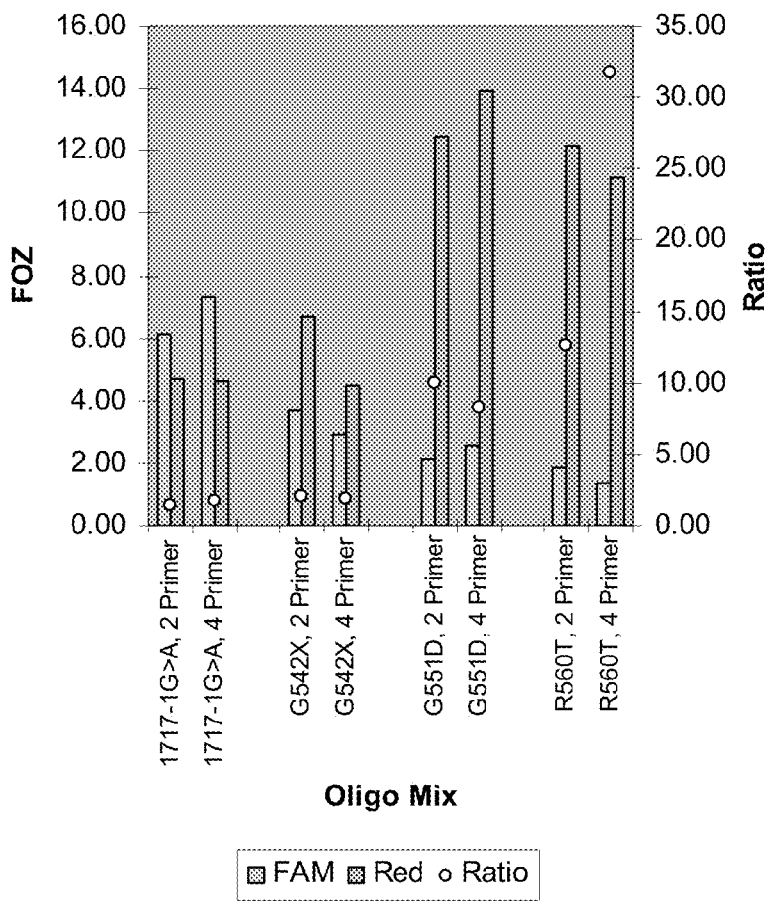
FIGS. 8A and 8B show the results, from Example 3, of detecting various CFTR alleles using snap-back primers to generate 3' hairpin structures that form invasive cleavage structure with upstream oligonucleotides.
Figure 8B:
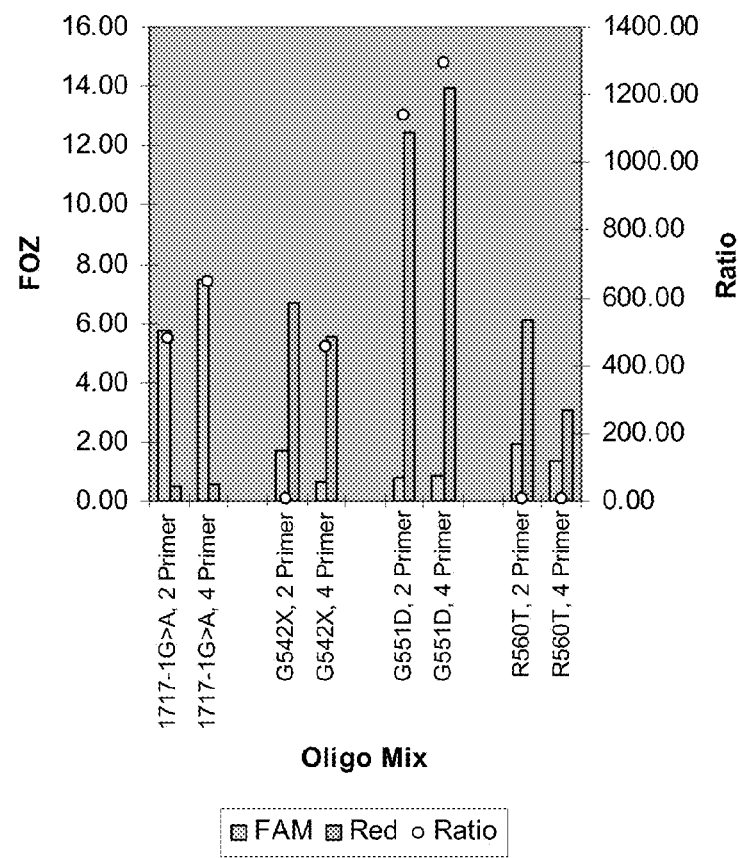

The results of the assay are shown in Table 7, Table 8, FIG. 8A (heterozygous data), and FIG. 8B (wild type data).

TABLE 6

| | FAM | | | | | | | | |
|---|---|---|---|---|---|---|---|---|---|
| | NTC-FAM | | | HET-FAM | | | WT-FAM | | |
| Signal | Avg. | SD | % CV | Avg. | SD | % CV | Avg. | SD | % CV |
| 1717-1G > A, 2 Primer | 755.00 | 40.71 | 5.39% | 4640.33 | 210.14 | 4.53% | 4371.67 | 102.57 | 2.35% |
| G542X, 2 Primer | 1023.00 | 143.16 | 13.99% | 3809.67 | 63.07 | 1.66% | 1772.67 | 63.07 | 3.56% |
| G551D, 2 Primer | 1720.67 | 191.65 | 11.14% | 3710.00 | 36.50 | 0.98% | 1365.67 | 61.50 | 4.50% |
| R560T, 2 Primer | 1706.33 | 198.10 | 11.61% | 3214.00 | 0.00 | 0.00% | 3305.33 | 47.25 | 1.43% |
| 1717-1G > A, 4 Primer | 576.33 | 59.18 | 10.27% | 4240.67 | 23.07 | 0.54% | 4317.67 | 78.53 | 1.82% |
| G542X, 4 Primer | 894.33 | 97.12 | 10.86% | 2579.33 | 149.13 | 5.78% | 587.00 | 31.24 | 5.32% |
| G551D, 4 Primer | 1647.67 | 135.06 | 8.20% | 4236.33 | 72.46 | 1.71% | 1428.67 | 57.00 | 3.99% |
| R560T, 4 Primer | 2767.67 | 1012.19 | 36.57% | 3656.00 | 73.73 | 2.02% | 3740.33 | 121.22 | 3.24% |

TABLE 6-continued

| | Red | | | | | | | | |
|---|---|---|---|---|---|---|---|---|---|
| | NTC-Red | | | HET-Red | | | WT-Red | | |
| | Avg. | SD | % CV | Avg. | SD | % CV | Avg. | SD | % CV |
| 1717-1G > A, 2 Primer | 1279.00 | 85.86 | 6.71% | 6012.67 | 308.28 | 5.13% | 674.00 | 18.33 | 2.72% |
| G542X, 2 Primer | 904.00 | 111.50 | 12.33% | 6032.67 | 68.79 | 1.14% | 6025.67 | 106.59 | 1.77% |
| G551D, 2 Primer | 465.00 | 30.05 | 6.46% | 5794.00 | 86.61 | 1.49% | 5771.00 | 142.38 | 2.47% |
| R560T, 2 Primer | 473.67 | 28.22 | 5.96% | 5760.67 | 38.68 | 0.67% | 2881.67 | 67.09 | 2.33% |
| 1717-1G > A, 4 Primer | 1116.33 | 126.98 | 11.37% | 5153.67 | 68.81 | 1.34% | 636.33 | 8.08 | 1.27% |
| G542X, 4 Primer | 894.33 | 83.67 | 9.36% | 3997.00 | 258.72 | 6.47% | 4970.00 | 315.13 | 6.34% |
| G551D, 4 Primer | 453.00 | 21.00 | 4.64% | 6312.67 | 131.46 | 2.08% | 6322.00 | 102.50 | 1.62% |
| R560T, 4 Primer | 640.33 | 145.71 | 22.75% | 7156.67 | 181.51 | 2.54% | 1975.00 | 84.86 | 4.30% |

TABLE 7

| | Signal | | | | | | |
|---|---|---|---|---|---|---|---|
| | FAM | | | | Red | | |
| | NTC-FAM | HET-FAM | WT-FAM | | NTC-Red | HET-Red | WT-Red |
| 1717-1G > A, 2 Primer | 755.00 | 4640.33 | 4371.67 | 1717-1G > A, 2 Primer | 1279.00 | 6012.67 | 674.00 |
| G542X, 2 Primer | 1023.00 | 3809.67 | 1772.67 | G542X, 2 Primer | 904.00 | 6032.67 | 6025.67 |
| G551D, 2 Primer | 1720.67 | 3710.00 | 1365.67 | G551D, 2 Primer | 465.00 | 5794.00 | 5771.00 |
| R560T, 2 Primer | 1706.33 | 3214.00 | 3305.33 | R560T, 2 Primer | 473.67 | 5760.67 | 2881.67 |
| 1717-1G > A, 4 Primer | 576.33 | 4240.67 | 4317.67 | 1717-1G > A, 4 Primer | 1116.33 | 5153.67 | 636.33 |
| G542X, 4 Primer | 894.33 | 2579.33 | 587.00 | G542X, 4 Primer | 894.33 | 3997.00 | 4970.00 |
| G551D, 4 Primer | 1647.67 | 4236.33 | 1428.67 | G551D, 4 Primer | 453.00 | 6312.67 | 6322.00 |
| R560T, 4 Primer | 2767.67 | 3656.00 | 3740.33 | R560T, 4 Primer | 640.33 | 7156.67 | 1975.00 |

These results show that the assay designs worked better multiplexed in this Example then monoplexed. The additional primers seem to reduce the level of background generated. These results also show robust detection of 1717-1G>A and G542X, with good detection of G551D (which may be improved with optimization of the HET ratio).

Example 4

Use of Forward and Reverse Snap-Back Primers to Form a Double Hairpin Structure for Genotyping This Examples describes the use of forward and reverse snap-back primers to form a double hairpin structure for genotyping. The sequence of the forward and reverse snap-back primers is as follows:

```
First Snap-Back Primer
                               (SEQ ID NO: 20)
ATGACGTGGCAGACCTGAGGCTTTCCTGATGACTATAAAAATAGACTTA CCTTCC;
and Second Snap-Back Primer
                               (SEQ ID NO: 21)
CGCGCCGAGGTTGAGGCTTTCCTGATGACTATAAAAATAGACTTACCTT

CC.

INVADER assay Primer:
                               (SEQ ID NO: 23)
TGTGTGCAATCGTGGGATAATTCTAAGAAA.
```

The assay with the forward and reverse snap-back primers was run against four genomic DNA samples. PCR amplification was carried out under the following conditions; 0.2 uM dNTPs, 1× AmpliTaq PCR Buffer, 1.25 uM of SEQ ID NO:20, SEQ ID NO:21, and SEQ ID NO:23, 1.25 U of AmpliTaq (+Hotstart Antibody), 20 ng of genomic DNA. Samples were subjected to the following incubation conditions (1×95 C for 10 min., 30× (95 C for 30 s, 52 C/30 s). The final amplification reactions were subjected to 5-fold dilutions and then run in an INVADER drydown plate (Cleavase VIII, Genomic Format) under the following conditions; 7 ul diluted PCR product, 3 ul dH20, 5 ul MgCl2 24 mM, +15 ul of Mineral Oil.

As shown in Table 8, all samples generated signal above background. Samples G1 and G2 (known heterozygote samples) showed more signal than G3 and G4 (known homozygote samples) in the RED channel suggesting that genotyping should be possible in that format.

TABLE 8

| | G1 | G2 | G3 | G4 | NTC | NTC | PCR no template |
|---|---|---|---|---|---|---|---|
| FAM_Raw Dilution Factor | | | | | | | |
| 0.2 | 171 | 153 | 375 | 380 | 76 | 73 | 70 |
| 0.04 | 90 | 85 | 108 | 102 | 69 | 69 | |
| 0.008 | 75 | 77 | 73 | 72 | 68 | 69 | |
| 0.0016 | 67 | 68 | 67 | 67 | 67 | 67 | |
| RED_Raw Dilution Factor | | | | | | | |
| 0.2 | 1909 | 1815 | 1445 | 1491 | 72 | 71 | 70 |
| 0.04 | 810 | 604 | 406 | 370 | 69 | 70 | |
| 0.008 | 199 | 163 | 109 | 110 | 69 | 71 | |
| 0.0016 | 89 | 75 | 71 | 74 | 67 | 68 | |

TABLE 8-continued

| | G1 | G2 | G3 | G4 | PCR no template NTC | NTC |
|---|---|---|---|---|---|---|
| FOZ Values | | | | | | |
| FAM | 0.2 | 2.5 | 2.2 | 5.4 | 5.4 | 1.1 | 1.0 |
| RED | 0.2 | 27.4 | 26.1 | 20.8 | 21.4 | 1.0 | 1.0 |
| RED | 0.04 | 11.6 | 8.7 | 5.8 | 5.3 | 1.0 | 1.0 |

Example 5

Comparing Snap-Back Primer Based Assays to Standard INVADER Assays

This Example examines the accuracy of genotype calls on 96 genomic DNA samples using the snap-back primer based assays in comparison to standard INVADER assays. The double snap-back primer assay design from Example 4 was employed, as wells as a standard INVADER assay composed of the following oligonucleotides:

```
INVADER assay Primer Number 1:
                                          (SEQ ID NO: 22)
TGTGTGCAAATKAGCCATCCTTCCAGAGGGTCGTGGGATAATTCTAAGA
AA;
and INVADER assay Primer Number 2:
                                          (SEQ ID NO: 23)
TGTGTGCAATCGTGGGATAATTCTAAGAAA.
```

Both assay designs were run against ninety-six (96) genomic DNA samples. For the snap-back primer assay reactions, PCR amplification was carried out under the following conditions; 0.2 uM dNTPs, 1× AmpliTaq PCR Buffer, 1.25 uM SEQ ID NO:20, SEQ ID NO:21, and SEQ ID NO:23, 0.5 U of AmpliTaq (+Hotstart Antibody), 25 ng of genomic DNA. Reaction mixes were subjected to the following incubation conditions (1×95 C for 10 minutes, 30× (95 C for 30 s, 52 C/30 s)). The final amplification reactions were subjected to a 5-fold dilution and then assembled in an INVADER drydown plate (Cleavase VIII, Genomic Format) as follows; 7 ul diluted PCR product, 3 ul dH20, 5 ul MgCl$_2$ 4 mM, +15 ul of Mineral Oil. The final mixes were incubated at 95 C for 5 minutes followed by 63 C for 20 minutes. For "Standard" Invader reactions (against genomic DNA), 70 ng of gDNA was used per reaction and incubated for 5 hours at 63 C.

Figure 9A:
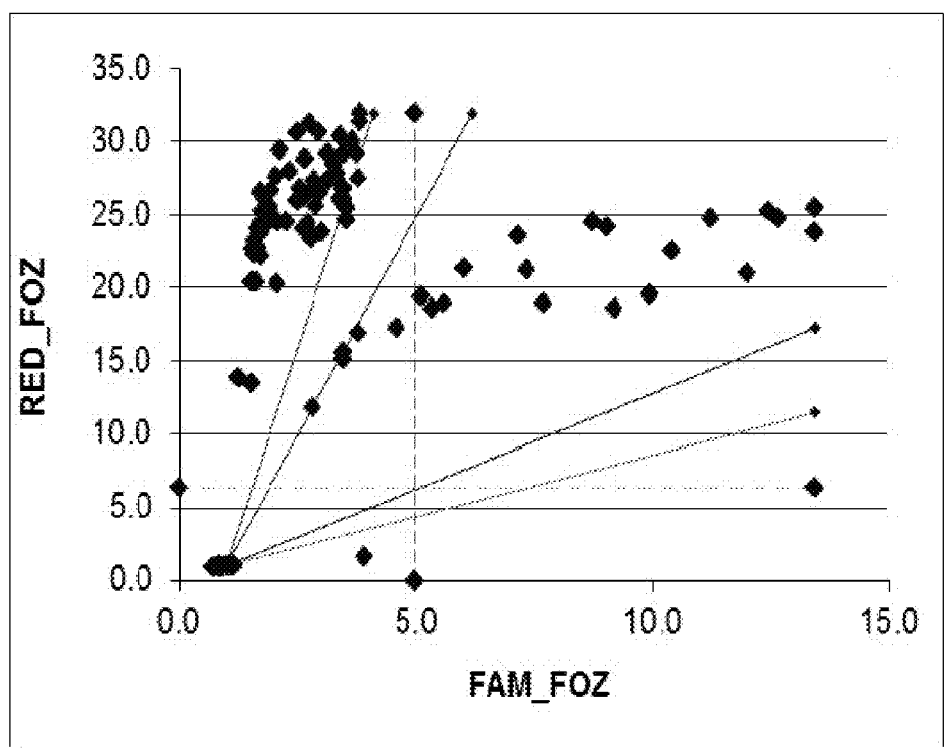
FIGS. 9A and 9B show the results, from Example 5, of detecting various CFTR alleles in 96 genomic DNA samples using snap-back primers to generate double hairpin structures that form invasive cleavage structures.
Figure 9B:
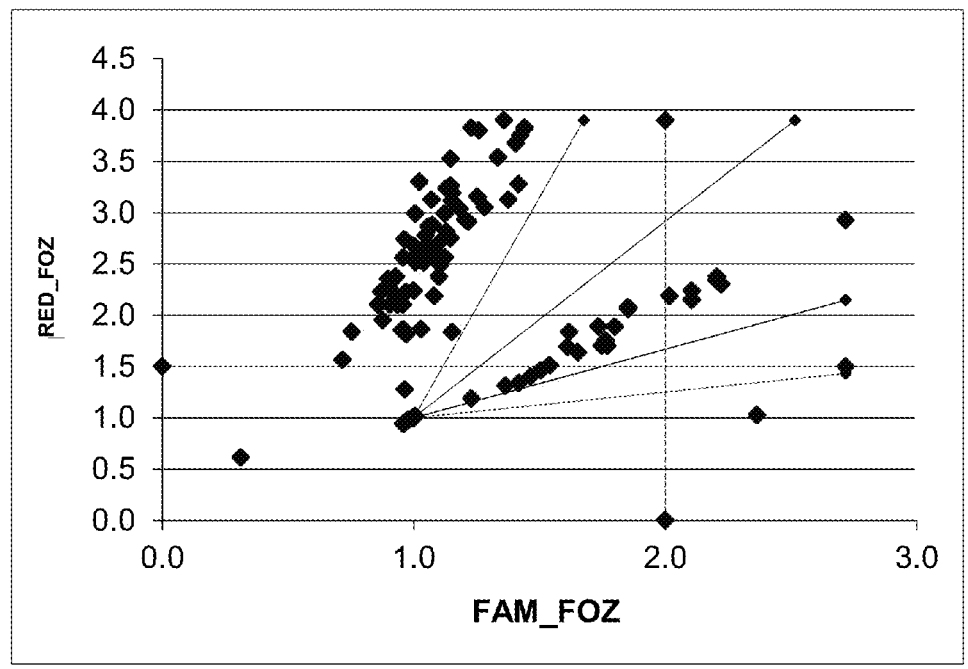

The results from these assays showed that, of the 96 samples, 82 samples could be genotyped by both the snap-back primer based assay and the standard INVADER methods. Applying scatter plot analysis using Excel based software, genotypes called by the snap-back primer based assays (FIG. 9A) were in 100% concordance (82/82) with the results from standard INVADER assay using genomic DNA (FIG. 9b).

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention should not be unduly limited to such specific embodiments. Indeed, various modifications of the described modes for carrying out the invention which are obvious to those skilled in the relevant arts are intended to be within the scope of the following claims.

We claim:

1. A composition, selected from the group consisting of:
   I) a first composition, configured for generating a 3' hairpin structure from a target nucleic acid, said first composition comprising a snap-back primer and a reverse primer,
      wherein said snap-back primer comprises:
         i) a 3' region configured to hybridize to said target nucleic acid such that it can be extended by a polymerase to generate a first amplification product, and
         ii) a 5' region configured to not hybridize to said target nucleic when said 3' region of said snap-back primer is hybridized to said target nucleic acid;
      wherein said reverse primer comprises a 3' region configured to hybridize to said first amplification product such that said reverse primer can be extended by a polymerase to generate a second amplification product comprising a 3' snap-back portion capable of hybridizing to a non-adjacent portion of said second amplification product to form a 3' hairpin structure, wherein said 3' hairpin structure comprises a 3' terminal portion configured to not hybridize to said second amplification product; and
   II) a second composition, configured for generating a 5' hairpin structure from a target nucleic acid, said second composition comprising a snap-back primer, wherein said snap-back primer comprises:
         i) a 3' region configured to hybridize to said target nucleic acid such that it can be extended by a polymerase to generate an amplification product, and
         ii) a 5' region configured to not hybridize to said target nucleic when said 3' region of said snap-back primer is hybridized to said target nucleic acid;
      wherein said amplification product comprises a 5' snap-back portion capable of hybridizing to a non-adjacent portion of said amplification product to form a 5' hairpin structure, wherein said 5' hairpin structure comprises a 5' terminal portion not hybridized to said amplification product.

2. The composition of claim 1, wherein in said first composition, said 3' hairpin structure comprises a first nucleotide located immediately 5' of said non-adjacent portion, wherein said first nucleotide corresponds to a second nucleotide at a polymorphic position in said target nucleic acid.

3. The composition of claim 1, wherein said first composition further comprises a downstream probe comprising a 3' region configured to hybridize to said 3' hairpin structure and a 5' region configured to not hybridize to said 3' hairpin structure.

4. The composition of claim 3, wherein said downstream probe is configured to hybridize to said 3' hairpin structure immediately 5' of said non-adjacent portion, thereby forming an invasive cleavage structure.

5. The composition of claim 1, wherein in said first composition, said 3' region of said snap-back primer comprises a sequence capable of hybridizing to said non-adjacent portion of said second amplification product.

6. The composition of claim 1, wherein in said first composition, said 3' region of said snap-back primer is not capable of hybridizing to said non-adjacent portion of said second amplification product.

7. The composition of claim 1, wherein in said first composition, said 3' terminal portion of said 3' hairpin structure is less than 10 nucleotides in length.

8. The composition of claim 1, wherein in said first composition, said 3' snap-back portion is partially complementary to said non-adjacent portion.

9. The composition of claim 1, wherein in said second composition, the 3' terminal nucleotide of said non-adjacent portion of said amplification product corresponds to, and is complementary to, a target nucleotide at a polymorphic position in said target nucleic acid.

10. The composition of claim 1, wherein said second composition further comprises an upstream probe comprising a 5' region configured to hybridize to said amplification product and a 3' region configured to not hybridize to said amplification product.

11. The composition of claim 10, wherein said upstream probe hybridizes to said amplification product immediately 3' of said non-adjacent portion thereby forming an invasive cleavage structure.

12. The composition of claim 1, wherein in said second composition, said 3' region of said snap-back primer comprises a sequence capable of hybridizing to the complement of said non-adjacent portion of said amplification product.

13. The composition of claim 1, wherein in said second composition, said 3' region of said snap-back primer is not capable of hybridizing to the complement of said non-adjacent portion of said amplification product.

14. The composition of claim 1, wherein in said second composition, said 5' terminal portion of said 5' hairpin structure is between 10 and 30 bases in length.

15. The composition of claim 1, further comprising a polymerase.

16. The composition of claim 1, further comprising a deoxynucleoside triphosphate.

17. The composition of claim 1, further comprising a FEN-1 flap endonuclease.

18. A kit for forming an invasive cleavage structure from a target nucleic acid, selected from the group consisting of:
   I) a first kit, comprising a snap-back primer and a reverse primer configured to amplify a target sequence, and a downstream probe,
      wherein said snap-back primer comprises:
         i) a 3' region configured to hybridize to said target nucleic acid such that it can be extended by a polymerase to generate a first amplification product, and
         ii) a 5' region configured to not hybridize to said target nucleic when said 3' region of said snap-back primer is hybridized to said target nucleic acid;
      wherein said reverse primer comprises a 3' region configured to hybridize to said first amplification product such that it can be extended by a polymerase to generate a second amplification product having a 3' hairpin structure; and
      wherein said downstream probe is configured to form an invasive cleavage structure with said 3' hairpin structure of said second amplification product, wherein said downstream probe comprises a 3' region configured to hybridize to second amplification product, and a 5' region configured to not hybridize to second amplification product;
   and
   II) a second kit, comprising a snap-back primer and an upstream probe, wherein said snap-back primer comprises:
         i) a 5' region configured to not hybridize to said target nucleic when said 3' region of said snap-back primer is hybridized to said target nucleic acid, and
         ii) a 3' region configured to hybridize to said target nucleic acid such that it can be extended by a polymerase to generate an amplification product comprising a 5' hairpin structure;
      wherein said upstream probe is configured to form an invasive cleavage structure with said 5' hairpin structure of said amplification product, wherein said upstream probe comprises a 5' region configured to hybridize to said amplification product and a 3' region configured to not hybridize to said amplification product.

19. The kit of claim 18, further comprising a polymerase.

20. The kit of claim 18, further comprising a deoxynucleoside triphosphate.

21. The kit of claim 18, further comprising a FEN-1 flap endonuclease.

* * * * *